(12) United States Patent
Kori et al.

(10) Patent No.: US 11,720,023 B2
(45) Date of Patent: Aug. 8, 2023

(54) MATERIAL FOR FORMING ORGANIC FILM, METHOD FOR FORMING ORGANIC FILM, PATTERNING PROCESS, AND COMPOUND

(71) Applicant: SHIN-ETSU CHEMICAL CO., LTD., Tokyo (JP)

(72) Inventors: Daisuke Kori, Joetsu (JP); Takayoshi Nakahara, Joetsu (JP); Yusuke Biyajima, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 470 days.

(21) Appl. No.: 17/089,259

(22) Filed: Nov. 4, 2020

(65) Prior Publication Data

US 2021/0181637 A1 Jun. 17, 2021

(30) Foreign Application Priority Data

Dec. 12, 2019 (JP) ................................ 2019-224907

(51) Int. Cl.
*G03F 7/11* (2006.01)
*C07D 209/48* (2006.01)
(Continued)

(52) U.S. Cl.
CPC .............. *G03F 7/11* (2013.01); *C07D 209/48* (2013.01); *C07D 403/14* (2013.01);
(Continued)

(58) Field of Classification Search
CPC ......... G03F 7/11; G03F 7/094; C07D 209/48; C07D 403/14; C07D 487/04; C08F 26/06;
(Continued)

(56) References Cited

U.S. PATENT DOCUMENTS

2002/0106909 A1 8/2002 Kato et al.
2004/0197709 A1 10/2004 Arase et al.
(Continued)

FOREIGN PATENT DOCUMENTS

JP 2002-334869 A 11/2002
JP 2004-205685 A 7/2004
(Continued)

OTHER PUBLICATIONS

May 17, 2021 Search Report issued in European Patent Application No. 20207298.9.

*Primary Examiner* — Caleen O Sullivan
(74) *Attorney, Agent, or Firm* — Oliff PLC

(57) ABSTRACT

The present invention provides a material for forming an organic film, containing a compound shown by the following general formula (1), and an organic solvent, where X represents an organic group having a valency of n1 and 2 to 50 carbon atoms, n1 represents an integer of 1 to 10, and $R_1$ represents at least one or more of the following general formulae (2) to (4). This aims to provide an organic film material for forming an organic film that has all of high filling property, high planarizing property, and excellent adhesive force to a substrate.

(Continued)

-continued

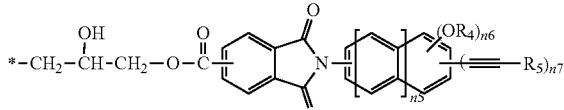
(3)

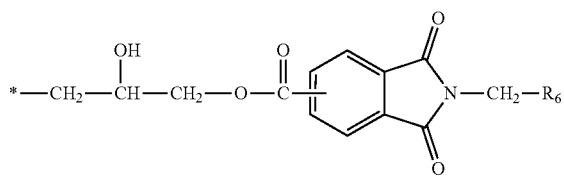

(4)

20 Claims, 3 Drawing Sheets

(51) Int. Cl.
| | |
|---|---|
| *C07D 403/14* | (2006.01) |
| *C07D 487/04* | (2006.01) |
| *C08F 26/06* | (2006.01) |
| *C09D 139/04* | (2006.01) |
| *G03F 7/09* | (2006.01) |
| *H01L 21/027* | (2006.01) |
| *H01L 21/033* | (2006.01) |
| *H01L 21/768* | (2006.01) |

(52) U.S. Cl.
CPC ............ *C07D 487/04* (2013.01); *C08F 26/06* (2013.01); *C09D 139/04* (2013.01); *G03F 7/094* (2013.01); *H01L 21/0273* (2013.01); *H01L 21/0337* (2013.01); *H01L 21/76819* (2013.01)

(58) Field of Classification Search
CPC .. C09D 139/04; C09D 171/00; C09D 171/12; H01L 21/0273; H01L 21/0337; H01L 21/76819; H01L 21/0271
USPC .......... 438/403; 430/311, 270.1, 271.1, 272.1
See application file for complete search history.

(56) References Cited

U.S. PATENT DOCUMENTS

| | | |
|---|---|---|
| 2005/0255712 A1 | 11/2005 | Kato et al. |
| 2006/0019195 A1 | 1/2006 | Hatakeyama et al. |
| 2006/0204891 A1 | 9/2006 | Hatakeyama |
| 2009/0274978 A1 | 11/2009 | Ohashi et al. |
| 2009/0311624 A1 | 12/2009 | Horiguchi et al. |
| 2010/0099044 A1 | 4/2010 | Hatakeyama et al. |
| 2012/0181251 A1 | 7/2012 | Minegishi et al. |
| 2013/0302990 A1 | 11/2013 | Watanabe et al. |
| 2015/0337164 A1 | 11/2015 | Ohashi et al. |
| 2017/0183531 A1* | 6/2017 | Kori ..................... G03F 7/0397 |
| 2017/0184968 A1* | 6/2017 | Kori ..................... C09D 5/008 |
| 2018/0086886 A1 | 3/2018 | Sakamoto et al. |
| 2020/0301278 A1 | 9/2020 | Tokunaga et al. |
| 2020/0333709 A1* | 10/2020 | Kori ..................... C07C 233/80 |
| 2021/0198472 A1* | 7/2021 | Kori ..................... C09D 171/00 |

FOREIGN PATENT DOCUMENTS

| | | |
|---|---|---|
| JP | 2005-128509 A | 5/2005 |
| JP | 2005-250434 A | 9/2005 |
| JP | 2006-227391 A | 8/2006 |
| JP | 2006-285095 A | 10/2006 |
| JP | 2006-293298 A | 10/2006 |
| JP | 2007-199653 A | 8/2007 |
| JP | 3985165 B2 | 10/2007 |
| JP | 2008-158002 A | 7/2008 |
| JP | 2009-269953 A | 11/2009 |
| JP | 2010-122656 A | 6/2010 |
| JP | 4784784 B2 | 10/2011 |
| JP | 2013-253227 A | 12/2013 |
| WO | 2004/066377 A1 | 8/2004 |
| WO | 2018/186310 A1 | 10/2018 |
| WO | 2019/146378 A1 | 8/2019 |

* cited by examiner

[FIG. 1]
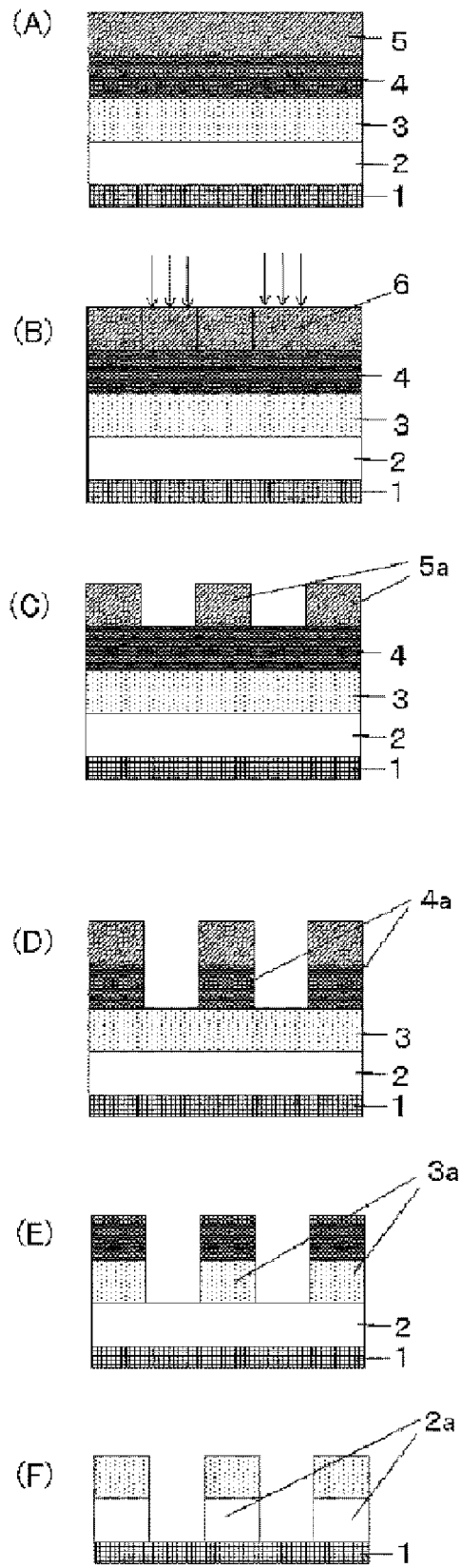

[FIG. 2]
(G)
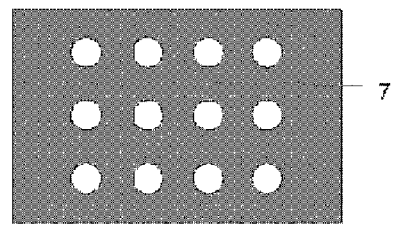
(H)
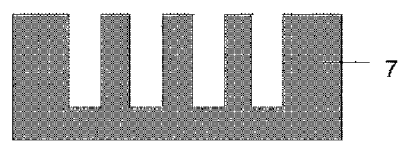
(I)
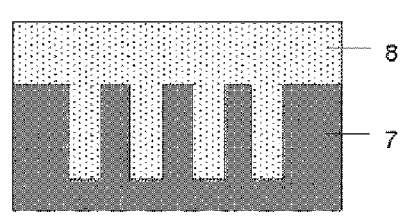
[FIG. 3]
(J)
(K)
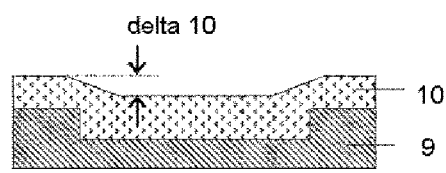

[FIG. 4]
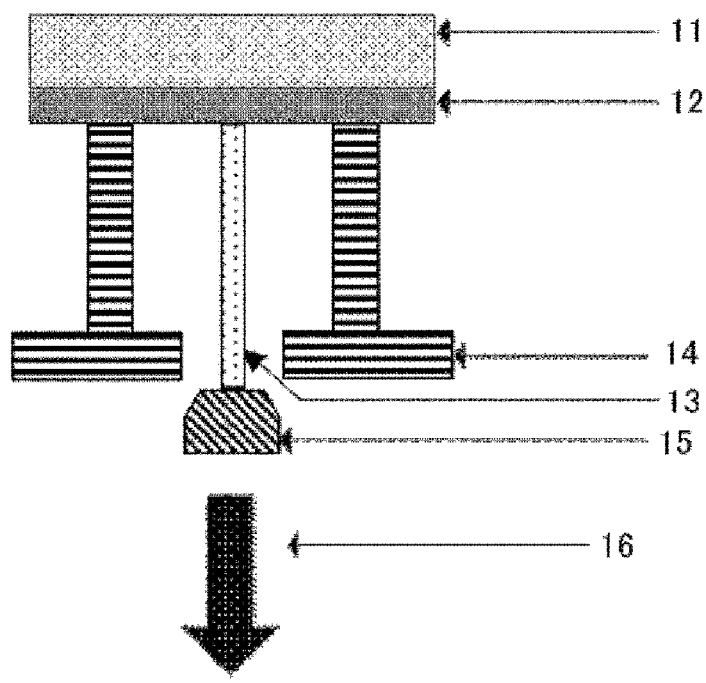

MATERIAL FOR FORMING ORGANIC FILM, METHOD FOR FORMING ORGANIC FILM, PATTERNING PROCESS, AND COMPOUND

TECHNICAL FIELD

The present invention relates to a material for forming an organic film, a method for forming an organic film, a patterning process, and a compound.

BACKGROUND ART

As LSIs advance toward higher integration and higher processing speed, miniaturization of pattern size is rapidly progressing. Along with this miniaturization, the lithography technology has achieved formation of fine patterns by shortening the wavelength of a light source and by selecting a proper resist composition corresponding to the shortened wavelength. The main factor of this achievement is a positive photoresist composition used as a monolayer. This monolayer positive photoresist composition allows a resist resin to have not only a skeleton that possesses etching resistance against dry etching with chlorine- or fluorine-based gas plasma, but also a resist mechanism that makes an exposed part soluble. Thereby, after a pattern is formed by dissolving the exposed part, a substrate to be processed on which the resist composition has been applied is dry-etched using the remaining resist pattern as an etching mask.

However, if the miniaturization is pursued, that is, if the pattern width is reduced, without changing the film thickness of a photoresist film to be used, the resolution of the photoresist film decreases. In addition, if the photoresist film is pattern-developed by using a developer, what is called an aspect ratio thereof becomes so large that pattern collapse occurs consequently. For these reasons, the thickness of the photoresist film has been reduced in accordance with the miniaturization.

On the other hand, a substrate to be processed has been generally processed by employing a method in which a substrate is processed by dry etching using a pattern-formed photoresist film as an etching mask. In practice, however, there is no dry etching method capable of providing an absolute etching selectivity between the photoresist film and the substrate to be processed. Thus, the resist film is also damaged and collapses during the substrate processing, and the resist pattern cannot be precisely transferred to the substrate to be processed. Accordingly, higher dry etching resistance has been required in a photoresist composition along with the pattern miniaturization. Meanwhile, a resin used for the photoresist composition has been required to have low light absorption at the shortened wavelength of the exposure light. The resin used for the photoresist composition thus has been shifted to a novolak resin, polyhydroxystyrene, and a resin having an aliphatic polycyclic skeleton as the exposure light is shifted to i-line, KrF, and ArF. This shift actually accelerates the etching rate under these dry etching conditions, and recent photoresist compositions having high resolution tend to have rather low etching resistance.

In such circumstances, a substrate to be processed has to be dry-etched with a thinner photoresist film having lower etching resistance. A material and a process reliably employed in this patterning process are urgently needed.

A multilayer resist method is one of solutions for these problems. In this method, a middle layer film having a different etching selectivity from that of a photoresist film (i.e., resist upper layer film) is placed between the resist upper layer film and a substrate to be processed; a pattern is formed in the resist upper layer film; then, the pattern is transferred to the middle layer film by dry etching by using the resist upper layer film pattern as a dry etching mask; and the pattern is further transferred to the substrate to be processed by dry etching by using the middle layer film as a dry etching mask.

One of the multilayer resist methods is a three-layer resist method which can be performed using a resist composition generally adopted in a monolayer resist method. In this three-layer resist method, for example, an organic film made of a novolak or the like is formed as a resist underlayer film on a substrate to be processed, a silicon-containing film is formed as a resist middle layer film on the resist underlayer film, and further a usual organic photoresist film is formed as a resist upper layer film on the resist middle layer film. When dry etching is performed with fluorine-based gas plasma, such an organic resist upper layer film can have a good etching selectivity ratio relative to the silicon-containing resist middle layer film, so that the resist upper layer film pattern is transferred to the silicon-containing resist middle layer film by dry etching with fluorine-based gas plasma. Further, the silicon-containing resist middle layer film can have a good etching selectivity ratio relative to the organic underlayer film in etching with an oxygen gas or a hydrogen gas, so that the silicon-containing middle layer film pattern is transferred to the underlayer film by etching with an oxygen gas or a hydrogen gas. According to this method, even if a resist composition to be used has difficulty in forming a pattern with a sufficient film thickness to directly process the substrate to be processed or does not have sufficient dry etching resistance to process the substrate, it is possible to obtain a pattern in the organic film (resist underlayer film) made of a novolak or the like having sufficient dry etching resistance for the processing, when the pattern can be transferred to the silicon-containing film (resist middle layer film).

As to the organic underlayer film as described above, numerous materials have been already known (for example, Patent Document 1). In recent years, there have been growing needs for an underlayer film excellent in filling property, planarizing property, or adhesiveness to a substrate, in addition to dry etching resistance. For example, when the substrate to be processed used as a base has a fine pattern structure such as hole and trench, the filling property is required to fill such pattern with a film completely without void. In addition, when the substrate to be processed used as a base has a step(s), or when one wafer includes both a pattern-dense region and a pattern-free region, the underlayer film to be formed on the substrate or the wafer needs to have a flat film surface. Planarizing the underlayer film surface can reduce fluctuation in film thickness of a middle layer film and a photoresist formed thereon, thus increasing a focus margin in lithography or a margin in a subsequent step of processing the substrate to be processed. Further, when an inorganic hard mask is formed on such an organic underlayer film, adhesive force is required with respect to the substrate. Improving the adhesive force makes it possible to form an organic film with excellent process margin, while preventing peeling off of the film, which might occur when the inorganic hard mask is formed directly on the organic film by employing a CVD method or an ALD method.

As means for improving the filling and planarizing properties of an underlayer film material, addition of a liquid additive such as polyether polyol has been proposed (Patent Document 2). However, an organic film formed by this method contains many polyether polyol units, which are inferior in etching resistance. Thus, this film has a markedly lowered etching resistance and is unsuitable for the three-layer resist underlayer film. Meanwhile, for a method of improving the adhesive force of an underlayer film material relative to a substrate, a resist underlayer film material having a lactone ring structure as a constituent moiety has been proposed (Patent Document 3). Nevertheless, this resist underlayer film material has a problem that the adhesiveness to a substrate is insufficient to meet the demands for cutting-edge devices. Meanwhile, Patent Document 4 has proposed an underlayer film which uses a compound having an imide group. Nevertheless, the adhesiveness to a substrate needs to be further improved. As described above, there are demands for: a resist underlayer film material achieving all of excellent filling property, planarizing property, and adhesive force to a substrate as well as sufficient etching resistance; and a patterning process using this resist underlayer film material.

Additionally, the usage of an organic film material excellent in filling property, planarizing property, and adhesive force to a substrate is not limited to an underlayer film for three-layer resist. Such an organic film material is widely applicable also as a planarizing material for manufacturing a semiconductor device, e.g., for planarizing a substrate prior to patterning by nanoimprinting. Furthermore, although a CMP process is now generally used for global planarization in the semiconductor device manufacturing process, the organic film material is also expected to be used for the global planarizing method in place of the CMP process because CMP is costly.

CITATION LIST

Patent Literature

Patent Document 1: JP 2004-205685 A
Patent Document 2: JP 4784784 B
Patent Document 3: JP 3985165 B
Patent Document 4: WO 2019/146378 A1

SUMMARY OF INVENTION

Technical Problem

The present invention has been made in view of the above-described circumstances. An object of the present invention is to provide an organic film material for forming an organic film that has all of high filling property, high planarizing property, and excellent adhesive force to a substrate.

Solution to Problem

To achieve the object, the present invention provides a material for forming an organic film, comprising: a compound shown by the following general formula (1); and an organic solvent,

wherein X represents an organic group having a valency of n1 and 2 to 50 carbon atoms; n1 represents an integer of 1 to 10; and $R_1$ represents at least one or more of the following general formulae (2) to (4),

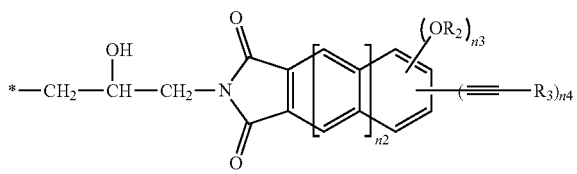

wherein an asterisk (*) represents a bonding site to the organic group X; n2 represents 0 or 1; n3 and n4 represent integers satisfying relations of $0 \leq n3 \leq 2$, $0 \leq n4 \leq 2$, and $1 \leq n3+n4 \leq 2$; $R_2$ represents any of a hydrogen atom, an allyl group, and a propargyl group; and $R_3$ represents any of a hydrogen atom, a methyl group, and a phenyl group,

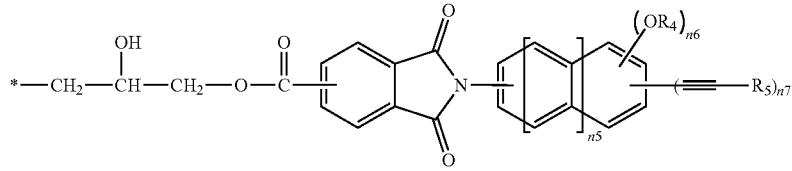

wherein an asterisk represents a bonding site to the organic group X; n5 represents 0 or 1; n6 and n7 represent integers satisfying relations of $0 \leq n6 \leq 2$, $0 \leq n7 \leq 2$, and $1 \leq n6+n7 \leq 2$; $R_4$ represents any of a hydrogen atom, an allyl group, and a propargyl group; and $R_5$ represents any of a hydrogen atom, a methyl group, and a phenyl group, and

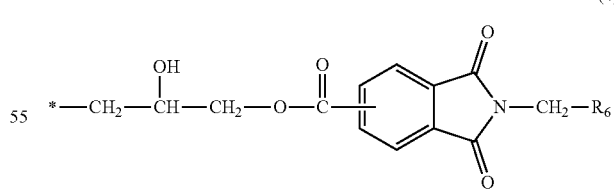

wherein an asterisk represents a bonding site to the organic group X; and $R_6$ represents a monovalent organic group having an unsaturated bond and 1 to 10 carbon atoms.

In such a material for forming an organic film, the imide group(s), each of which is linked with a flexible chain having a hydroxyl group at the terminal structure, enable the material for forming an organic film to form an organic film excellent in adhesive force to a substrate while achieving all of heat resistance and high filling property/high planarizing property. Moreover, such a material for forming an organic film is capable of exhibiting high dry etching resistance, too.

The present invention provides the material for forming an organic film, wherein the X in the general formula (1) is shown by any of the following general formulae (5), (7), (8), (9), (10), (11), (12), (13), (14), and (15),

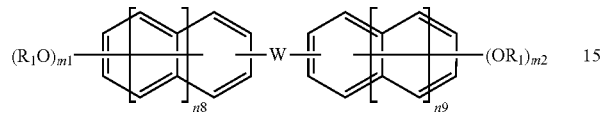
(5)

wherein n8 and n9 each independently represent 0 or 1; W represents a single bond or any of structures shown by (6) below; $R_1$ represents the $R_1$ group; and m1 and m2 each independently represent an integer of 0 to 4, and m1+m2 is 1 or more and 8 or less,

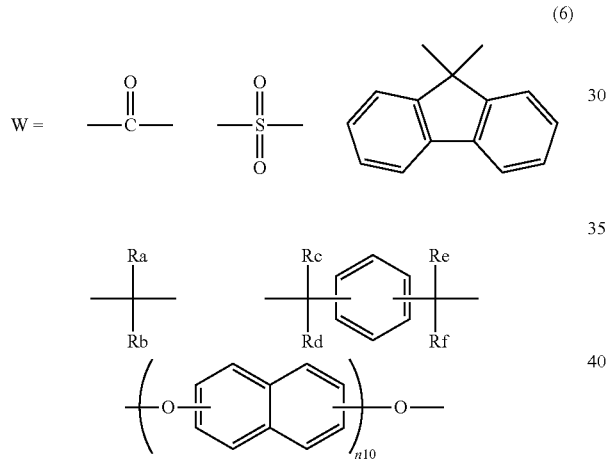
(6)

wherein n10 represents an integer of 0 to 3; and Ra, Rb, Rc, Rd, Re, and Rf each independently represent a hydrogen atom, an alkyl group having 1 to 10 carbon atoms optionally substituted with fluorine, or a phenyl group, and Ra and Rb are optionally bonded to each other to form a cyclic compound, (7)

wherein $R_1$ represents the $R_1$ group; and Rg represents a hydrogen atom, a methyl group, or a phenyl group, (8)

(9)

(10)

(11)

(12)

wherein $R_1$ represents the $R_1$ group; Rh, Ri, Rj, Rk, Rl, Rm, and Rn each represent a hydrogen atom, an alkyl group having 1 to 10 carbon atoms, an alkynyl group having 2 to 10 carbon atoms, an alkenyl group having 2 to 10 carbon atoms, a benzyl group optionally having a substituent on an aromatic ring thereof, or a phenyl group; and each Y represents the $R_1$ group, a hydrogen atom, an alkyl group having 1 to 10 carbon atoms, an alkynyl group having 2 to 10 carbon atoms, or an alkenyl group having 2 to 10 carbon atoms, and at least two of four Y's in the general formula (12) are the $R_1$ groups, and (13)

(14)

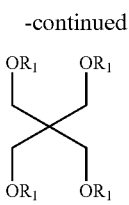

(15)

wherein $R_1$ represents the $R_1$ group; Ro represents a linear, branched, or cyclic, saturated or unsaturated hydrocarbon group having 1 to 20 carbon atoms; and Rp represents a hydrogen atom or an alkyl group having 1 to 10 carbon atoms.

Such a material for forming an organic film is a material for forming an organic film that has all of high filling property, high planarizing property, and favorable adhesiveness to a substrate. Further, it is also possible to control various properties such as etching resistance and optical properties by appropriately selecting the structure of the organic group X in accordance with the required performances.

Further, the present invention provides the material for forming an organic film, wherein the $R_1$ group comprises:
any one or more shown by the general formulae (2) to (4); and
any one or more shown by the following general formulae (16) and (17),

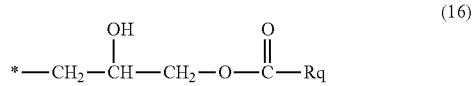

(16)

wherein Rq represents a linear, branched, or cyclic, saturated or unsaturated hydrocarbon group having 1 to 30 carbon atoms; and a methylene group constituting the Rq group is optionally substituted with an oxygen atom or a carbonyl group, and

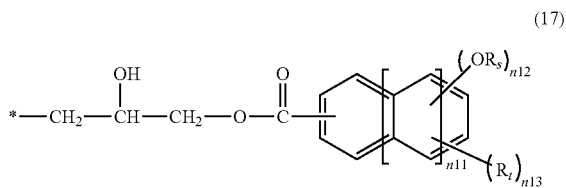

(17)

wherein Rs represents a hydrogen atom or a linear or branched hydrocarbon group having 1 to 10 carbon atoms; Rt represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n11 represents any of 0 to 2; and n12 and n13 each represent the number of substituents on an aromatic ring, n12 and n13 each represent an integer of 0 to 7, and n12+n13 is 0 or more and 7 or less.

When the material for forming an organic film contains such a compound, since a terminal group(s) each having the aromatic ring or the hydrocarbon structure are used in combination, various properties can be adjusted or improved in accordance with the required performances; for example, it is possible to control the heat resistance, etching resistance, filling and planarizing properties, adhesiveness to a substrate, and optical constant (n/k).

More preferably, the material for forming an organic film further comprises one or more of an acid generator, a surfactant, a crosslinking agent, and a plasticizer.

The inventive material for forming an organic film may contain at least one of these components, depending on the purpose.

Further, the present invention provides the material for forming an organic film, wherein the organic solvent is a mixture of one or more organic solvents each having a boiling point of lower than 180° C. and one or more organic solvents each having a boiling point of 180° C. or higher.

With such a material for forming an organic film, the addition of the high-boiling-point solvent(s) to the above-described polymer imparts thermal flowability to the resulting film. Thus, the material for forming an organic film has higher filling property and higher planarizing property.

As described above, when the inventive material for forming an organic film is used to form a multilayer resist film that is applied to fine processing in processes of manufacturing semiconductor devices and the like, it is possible to provide a resist underlayer film material for forming a resist underlayer film that has high dry etching resistance as well as high filling property, high planarizing property, and excellent adhesive force to a substrate. It is also possible to provide a planarizing material for manufacturing semiconductor devices, the planarizing material being excellent in filling property, planarizing property, and adhesive force to a substrate, and being applicable to planarization in semiconductor device manufacturing processes besides multilayer resist processes.

Moreover, the present invention provides a method for forming an organic film that serves as an organic flat film employed in a semiconductor device manufacturing process, the method comprising:
spin-coating a substrate to be processed with the inventive material for forming an organic film; and
heating the substrate at a temperature of 100° C. or higher and 600° C. or lower for 10 seconds to 600 seconds to form a cured film.

Heating the organic film material at the temperature of 100° C. or higher and 600° C. or lower for the period of 10 seconds to 600 seconds after coating with the organic film material as described above can promote the crosslinking reaction and prevent mixing with a film formed thereon.

Further, the present invention provides a method for forming an organic film that serves as an organic flat film employed in a semiconductor device manufacturing process, the method comprising:
spin-coating a substrate to be processed with the above-described material for forming an organic film; and
heating the substrate under an atmosphere with an oxygen concentration of 0.1% or more and 21% or less to form a cured film.

By baking the inventive material for forming an organic film in an atmosphere with such an oxygen concentration, a sufficiently-cured organic film can be obtained.

In this event, the substrate to be processed preferably has a structure or step with a height of 30 nm or more.

Because of the excellent filling property, planarizing property, and adhesive force to a substrate, the inventive organic film material is particularly useful for forming a flat organic film on a substrate having a structure or step with a height of 30 nm or more.

The present invention also provides a patterning process comprising:

forming a resist underlayer film by using the inventive material for forming an organic film on a body to be processed;

forming a resist middle layer film by using a silicon-containing resist middle layer film material on the resist underlayer film;

forming a resist upper layer film by using a resist upper layer film material including a photoresist composition on the resist middle layer film;

forming a circuit pattern in the resist upper layer film;

etching the resist middle layer film while using the resist upper layer film having the formed pattern as a mask to transfer the pattern to the resist middle layer film;

etching the resist underlayer film while using the resist middle layer film having the transferred pattern as a mask to transfer the pattern to the resist underlayer film; and further etching the body to be processed while using the resist underlayer film having the transferred pattern as a mask to form the pattern in the body to be processed.

In such a multilayer resist process, the patterning process using the inventive material for forming an organic film makes it possible to precisely form a fine pattern in a substrate to be processed.

In this event, when the resist underlayer film is etched by using the resulting resist middle layer film pattern as the etching mask, the etching is preferably performed with an etching gas mainly containing an oxygen gas or a hydrogen gas.

The silicon atom-containing resist middle layer film exhibits etching resistance to an oxygen gas or a hydrogen gas, so that the resist underlayer film can be etched with an etching gas mainly containing an oxygen gas or a hydrogen gas while the resist middle layer film is used as an etching mask.

Moreover, the present invention provides a patterning process comprising:

forming a resist underlayer film by using the inventive material for forming an organic film on a body to be processed;

forming a resist middle layer film by using a resist middle layer film material containing silicon atoms on the resist underlayer film;

forming an organic antireflective coating on the resist middle layer film;

forming a resist upper layer film on the organic antireflective coating by using a resist upper layer film material including a photoresist composition, so that a four-layered film structure is constructed;

forming a circuit pattern in the resist upper layer film;

etching the organic antireflective coating and the resist middle layer film while using the resist upper layer film having the formed pattern as a mask to transfer the pattern to the organic antireflective coating and the resist middle layer film;

etching the resist underlayer film while using the resist middle layer film having the transferred pattern as a mask to transfer the pattern to the resist underlayer film; and further etching the body to be processed while using the resist underlayer film having the transferred pattern as a mask to form the pattern in the body to be processed.

Further, the present invention provides a patterning process comprising:

forming a resist underlayer film by using the inventive material for forming an organic film on a body to be processed;

forming an inorganic hard mask middle layer film selected from a silicon oxide film, a silicon nitride film, and a silicon oxynitride film on the resist underlayer film;

forming a resist upper layer film by using a resist upper layer film material including a photoresist composition on the inorganic hard mask middle layer film;

forming a circuit pattern in the resist upper layer film;

etching the inorganic hard mask middle layer film while using the resist upper layer film having the formed pattern as a mask to transfer the pattern to the inorganic hard mask middle layer film;

etching the resist underlayer film while using the inorganic hard mask middle layer film having the formed pattern as a mask to transfer the pattern to the resist underlayer film; and further etching the body to be processed while using the resist underlayer film having the formed pattern as a mask to form the pattern in the body to be processed.

As described above, a resist middle layer film may be formed on a resist underlayer film, but any inorganic hard mask middle layer film selected from a silicon oxide film, a silicon nitride film, and a silicon oxynitride film can also be formed on the resist underlayer film. Further, a photoresist film may be formed as a resist upper layer film on the inorganic hard mask middle layer film, but it is also possible to form an organic antireflective coating (BARC) on the inorganic hard mask middle layer film by spin coating, and then form the photoresist film on the BARC. When a silicon oxynitride film (SiON film) is used as the inorganic hard mask middle layer film, two antireflective films including the SiON film and the BARC make it possible to suppress the reflection even in liquid immersion exposure at a high NA exceeding 1.0. Another merit of the BARC formation is having an effect of reducing trailing of the photoresist pattern immediately above the SiON film.

Specifically, the present invention provides a patterning process comprising:

forming a resist underlayer film by using the inventive material for forming an organic film on a body to be processed;

forming an inorganic hard mask middle layer film selected from a silicon oxide film, a silicon nitride film, and a silicon oxynitride film on the resist underlayer film;

forming an organic antireflective coating on the inorganic hard mask middle layer film;

forming a resist upper layer film on the organic antireflective coating by using a resist upper layer film material including a photoresist composition, so that a four-layered film structure is constructed;

forming a circuit pattern in the resist upper layer film;

etching the organic antireflective coating and the inorganic hard mask middle layer film while using the resist upper layer film having the formed pattern as a mask to transfer the pattern to the organic antireflective coating and the inorganic hard mask middle layer film;

etching the resist underlayer film while using the inorganic hard mask middle layer film having the formed pattern as a mask to transfer the pattern to the resist underlayer film; and further etching the body to be processed while using the resist underlayer film having the formed pattern as a mask to form the pattern in the body to be processed.

In addition, in the inventive patterning processes, the inorganic hard mask middle layer film can be formed by a CVD method or an ALD method.

In the inventive patterning processes, the inorganic hard mask middle layer film formed by a CVD method or an ALD method can be combined with the resist underlayer film formed by a spin-coating method.

Furthermore, the circuit pattern is preferably formed such that the circuit pattern is formed in the resist upper layer film by a photolithography using light with a wavelength of 10 nm or more and 300 nm or less, direct lithography with electron beam, nanoimprinting, or a combination thereof.

Furthermore, the circuit pattern is preferably formed such that the pattern is formed in the resist upper layer film by developing the circuit pattern with an alkali or organic solvent.

Furthermore, the body to be processed is preferably a semiconductor device substrate, a metal film, a metal carbide film, a metal oxide film, a metal nitride film, a metal oxycarbide film, or a metal oxynitride film (for example, the semiconductor device substrate coated with any of a metal film, a metal carbide film, a metal oxide film, a metal nitride film, a metal oxycarbide film, and a metal oxynitride film).

Furthermore, the body to be processed preferably comprises silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

The inventive patterning processes are capable of processing bodies to be processed as described above to form a pattern.

Further, the present invention provides a compound shown by the following general formula (1),

 (1)

wherein X represents an organic group having a valency of n1 and 2 to 50 carbon atoms; n1 represents an integer of 1 to 10; and $R_1$ represents at least one or more of the following general formulae (2) to (4),

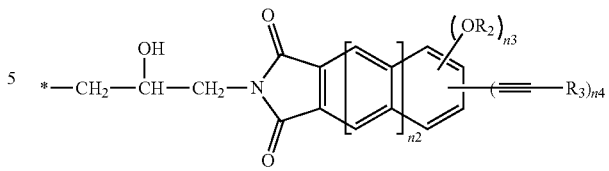

wherein an asterisk represents a bonding site to the organic group X; n2 represents 0 or 1; n3 and n4 represent integers satisfying relations of $0 \leq n3 \leq 2$, $0 \leq n4 \leq 2$, and $1 \leq n3+n4 \leq 2$; $R_2$ represents any of a hydrogen atom, an allyl group, and a propargyl group; and $R_3$ represents any of a hydrogen atom, a methyl group, and a phenyl group,

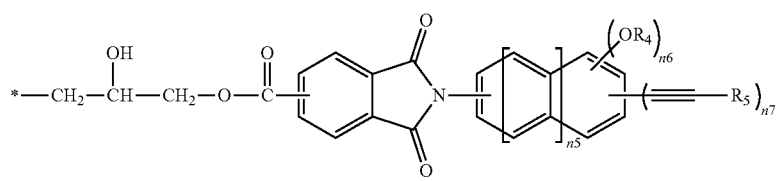

wherein an asterisk represents a bonding site to the organic group X; n5 represents 0 or 1; n6 and n7 represent integers satisfying relations of $0 \leq n6 \leq 2$, $0 \leq n7 \leq 2$, and $1 \leq n6+n7 \leq 2$; $R_4$ represents any of a hydrogen atom, an allyl group, and a propargyl group; and $R_5$ represents any of a hydrogen atom, a methyl group, and a phenyl group, and

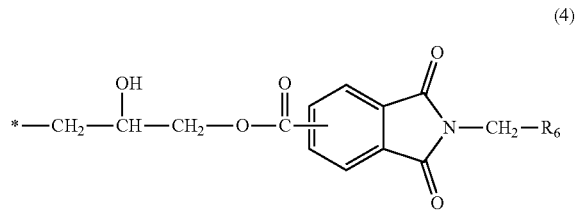

wherein an asterisk represents a bonding site to the organic group X; and $R_6$ represents a monovalent organic group having an unsaturated bond and 1 to 10 carbon atoms.

When used as a component of a material for forming an organic film, the inventive compound having an imide group as a terminal group enables the organic film material to form an organic film that is provided with high heat resistance, filling property, and planarizing property as well as excellent adhesive force to a substrate. Since thermosetting property can be imparted by appropriately selecting a substituent of the terminal group having the imide group, the thermosetting property is exhibited in combination with the effect of improving the heat resistance by the imide group introduction, so that the film shrinkage during baking is suppressed. This makes it possible to form an organic film excellent in planarizing property. Moreover, the terminal group having the imide group is linked with a flexible chain, so that the thermal flowability is improved and the filling and planarizing properties are improved. Additionally, the hydroxyl group introduced on the flexible chain has actions to improve the solubility into a solvent and improve the adhesiveness to a substrate. Thus, the inventive compound is quite useful in a material for forming an organic film with high filling property, high planarizing property, and excellent adhesiveness to a substrate.

The present invention provides the compound, wherein the organic group X in the general formula (1) is shown by any of the following general formulae (5), (7), (8), (9), (10), (11), (12), (13), (14), and (15), (5)

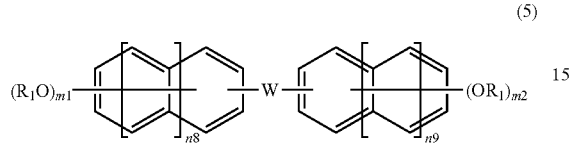

wherein n8 and n9 each independently represent 0 or 1; W represents a single bond or any of structures shown by (6) below; $R_1$ represents the $R_1$ group; and m1 and m2 each independently represent an integer of 0 to 4, and m1+m2 is 1 or more and 8 or less, (6)

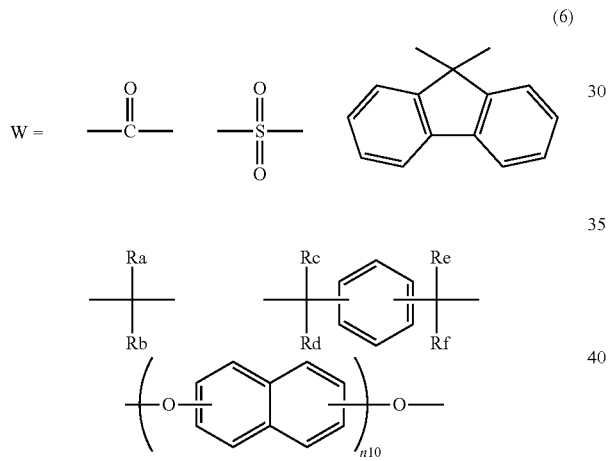

wherein n10 represents an integer of 0 to 3; and Ra, Rb, Rc, Rd, Re, and Rf each independently represent a hydrogen atom, an alkyl group having 1 to 10 carbon atoms optionally substituted with fluorine, or a phenyl group, and Ra and Rb are optionally bonded to each other to form a cyclic compound, (7)

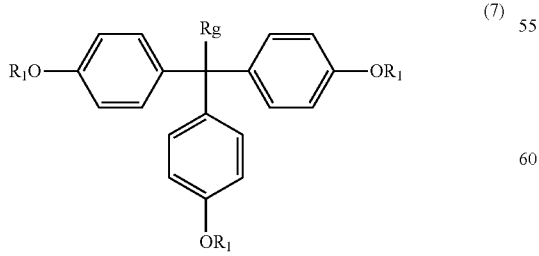

wherein $R_1$ represents the $R_1$ group; and Rg represents a hydrogen atom, a methyl group, or a phenyl group, (8)

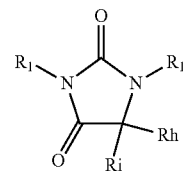

(9)

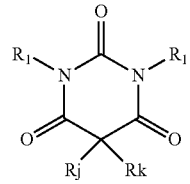

(10)

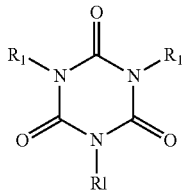

(11)

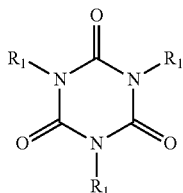

(12)

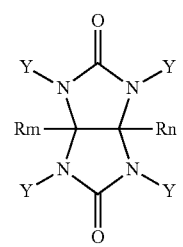

wherein $R_1$ represents the $R_1$ group; Rh, Ri, Rj, Rk, Rl, Rm, and Rn each represent a hydrogen atom, an alkyl group having 1 to 10 carbon atoms, an alkynyl group having 2 to 10 carbon atoms, an alkenyl group having 2 to 10 carbon atoms, a benzyl group optionally having a substituent on an aromatic ring thereof, or a phenyl group; and each Y represents the $R_1$ group, a hydrogen atom, an alkyl group having 1 to 10 carbon atoms, an alkynyl group having 2 to 10 carbon atoms, or an alkenyl group having 2 to 10 carbon atoms, and at least two of four Y's in the general formula (12) are the $R_1$ groups, and (13)

$R_1O$—Ro—$OR_1$ (14)

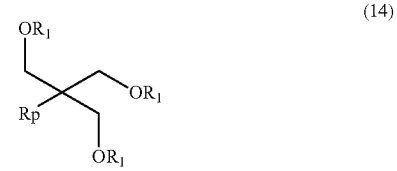

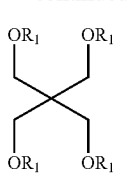
(15)

wherein $R_1$ represents the $R_1$ group; Ro represents a linear, branched, or cyclic, saturated or unsaturated hydrocarbon group having 1 to 20 carbon atoms; and Rp represents a hydrogen atom or an alkyl group having 1 to 10 carbon atoms.

When such a compound is used as a component of an organic film material, various properties can be adjusted in accordance with the required performances by appropriately selecting the structure of the organic group X; for example, the heat resistance, etching resistance, filling and planarizing properties, adhesiveness to a substrate, and optical constant (n/k) can be controlled.

Furthermore, the present invention provides the compound, wherein the $R_1$ group in the general formula (1) comprises:

any one or more shown by the general formulae (2) to (4); and any one or more shown by the following general formulae (16) and (17),

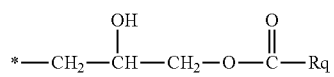
(16)

wherein Rq represents a linear, branched, or cyclic, saturated or unsaturated hydrocarbon group having 1 to 30 carbon atoms; and a methylene group constituting the Rq group is optionally substituted with an oxygen atom or a carbonyl group, and

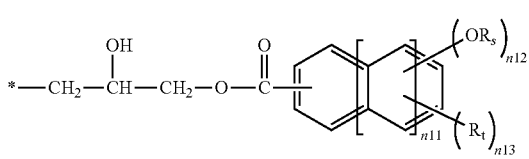
(17)

wherein Rs represents a hydrogen atom or a linear or branched hydrocarbon group having 1 to 10 carbon atoms; Rt represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n11 represents any of 0 to 2; and n12 and n13 each represent the number of substituents on an aromatic ring, n12 and n13 each represent an integer of 0 to 7, and n12+n13 is 0 or more and 7 or less.

Such a compound can be used in combination with the structure(s) of the aromatic ring structure and/or the hydrocarbon terminal group. When the compound is used as a component of a material for forming an organic film, various properties can be adjusted in accordance with the required performances; for example, it is possible to control the heat resistance, etching resistance, filling and planarizing properties, adhesiveness to a substrate, and optical constant (n/k).

Advantageous Effects of Invention

As described above, according to the present invention, there can be provided: a compound useful as a component of a material for forming an organic film that has all of high filling property, high planarizing property, and excellent adhesive force to a substrate; and a material for forming an organic film, the material containing this compound. Moreover, this organic film material has excellent filling property, planarizing property, and adhesive force to a substrate without impairing other properties such as heat resistance and etching resistance. Thus, the material for forming an organic film is quite useful as a planarizing material for manufacturing semiconductor devices or a resist underlayer film material in multilayer resist processes, for example, a two-layer resist process, a three-layer resist process using a silicon-containing middle layer film, or a four-layer resist process using a silicon-containing middle layer film and an organic antireflective coating.

Further, the inventive methods for forming an organic film make it possible to form a sufficiently cured flat organic film on a substrate to be processed. Furthermore, the inventive patterning processes are capable of precisely forming a fine pattern in a substrate to be processed according to multilayer resist processes.

BRIEF DESCRIPTION OF DRAWINGS

FIG. 1 shows explanatory views for illustrating an exemplary patterning process according to a three-layer resist process of the present invention.

FIG. 2 shows explanatory views for illustrating a method for evaluating the filling property in Examples and Comparative Examples.

FIG. 3 shows explanatory views for illustrating a method for evaluating the planarizing property in Examples and Comparative Examples.

FIG. 4 is an explanatory view for illustrating a method for measuring the adhesiveness in Examples and Comparative Examples.

DESCRIPTION OF EMBODIMENTS

The present invention relates to a resist underlayer film material used in multilayer resist processes and so forth employed in fine processing in processes of manufacturing semiconductor devices and the like; a material for forming an organic film, the material being effective as a planarizing material for manufacturing semiconductor devices, etc.; a method for forming a film using the materials; a patterning process using the material for forming an organic film and suitably performed by exposure with deep ultraviolet ray, KrF excimer laser beam (248 nm), ArF excimer laser beam (193 nm), $F_2$ laser beam (157 nm), $Kr_2$ laser beam (146 nm), $Ar_e$ laser beam (126 nm), soft X-ray (EUV), electron beam (EB), ion beam, X-ray, etc.; and a compound useful as a component of the material for forming an organic film.

As noted above, there have been demands for a material for forming an organic film that has all of high filling property, high planarizing property, and excellent adhesive force to a substrate.

The present inventors have earnestly studied the above-described object and consequently found that when a material for forming an organic film contains a compound shown by the following general formula (1), the organic film material can form an organic film having all of high filling property, high planarizing property, and excellent adhesive force to a substrate. This finding has led to the completion of the present invention.

Specifically, the present invention is a material for forming an organic film, containing:
a compound shown by the following general formula (1); and
an organic solvent,

  (1)

wherein X represents an organic group having a valency of n1 and 2 to 50 carbon atoms; n1 represents an integer of 1 to 10; and $R_1$ represents at least one or more of the following general formulae (2) to (4),

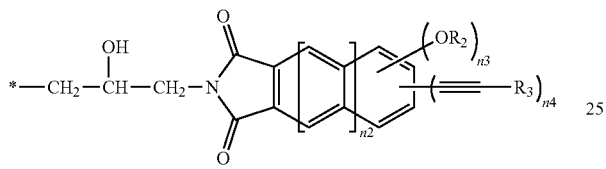  (2)

wherein an asterisk represents a bonding site to the organic group X; n2 represents 0 or 1; n3 and n4 represent integers satisfying relations of 0≤n3≤2, 0≤n4≤2, and 1≤n3+n4≤2; $R_2$ represents any of a hydrogen atom, an allyl group, and a propargyl group; and $R_3$ represents any of a hydrogen atom, a methyl group, and a phenyl group,

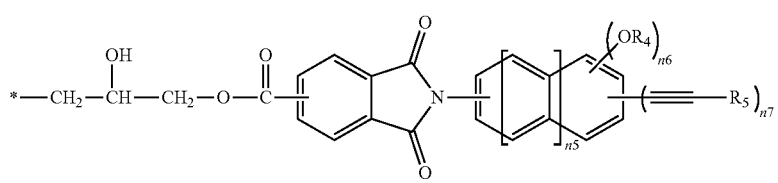  (3)

wherein an asterisk represents a bonding site to the organic group X; n5 represents 0 or 1; n6 and n7 represent integers satisfying relations of 0≤n6≤2, 0≤n7≤2, and 1≤n6+n7≤2; $R_4$ represents any of a hydrogen atom, an allyl group, and a propargyl group; and $R_5$ represents any of a hydrogen atom, a methyl group, and a phenyl group, and

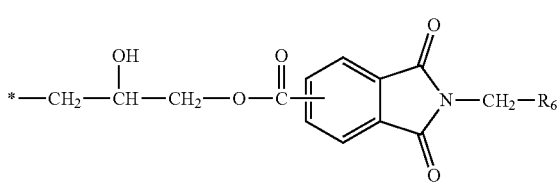  (4)

wherein an asterisk represents a bonding site to the organic group X; and $R_6$ represents a monovalent organic group having an unsaturated bond and 1 to 10 carbon atoms.

In such a material for forming an organic film, the terminal group structure(s), each of which contains an imide group linked with a flexible chain having a hydroxyl group, enable the material for forming an organic film to form an organic film excellent in adhesive force to a substrate while achieving all of heat resistance, high filling property, and high planarizing property. Moreover, such a material for forming an organic film is capable of exhibiting high dry etching resistance, too.

Hereinafter, embodiments of the present invention will be described, but the present invention is not limited thereto.

<Compound for Forming Organic Film>

A compound incorporated in the inventive material for forming an organic film is a compound for forming an organic film, and shown by the following general formula In the general formula (1), X is an organic group having a valency of n1 and 2 to 50 carbon atoms. n1 represents an integer of 1 to 10. $R_1$ is at least one or more of the following general formulae (2) to (4).

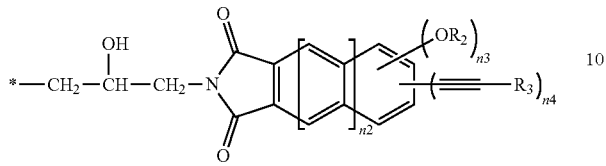
(2)

In the general formula (2), an asterisk (*) represents a bonding site to the organic group X. n2 represents 0 or 1. n3 and n4 are integers satisfying relations of $0 \le n3 \le 2$, $0 \le n4 \le 2$, and $1 \le n3+n4 \le 2$. $R_2$ is any of a hydrogen atom, an allyl group, and a propargyl group. $R_3$ is any of a hydrogen atom, a methyl group, and a phenyl group.

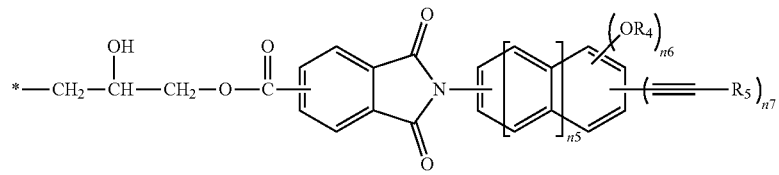
(3)

In the general formula (3), an asterisk represents a bonding site to the organic group X. n5 represents 0 or 1. n6 and n7 are integers satisfying relations of $0 \le n6 \le 2$, $0 \le n7 \le 2$, and $1 \le n6+n7 \le 2$. $R_4$ is any of a hydrogen atom, an allyl group, and a propargyl group. $R_5$ is any of a hydrogen atom, a methyl group, and a phenyl group.

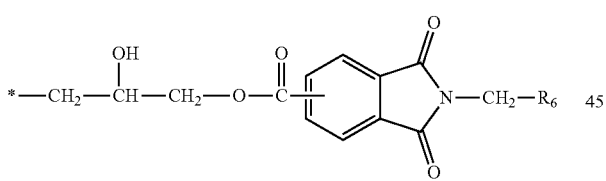
(4)

In the general formula (4), an asterisk represents a bonding site to the organic group X. $R_6$ is a monovalent organic group having an unsaturated bond and 1 to 10 carbon atoms.

Specific examples of the organic group X in the general formula (1) include the following groups and other similar groups. In the following formulae, $R_1$ is defined above, m1 and m2 each independently represent an integer of 0 to 4, and m1+m2 is 1 or more and 8 or less, and n10 represents an integer of 0 to 3.

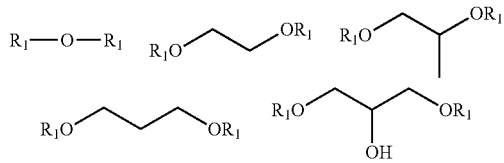

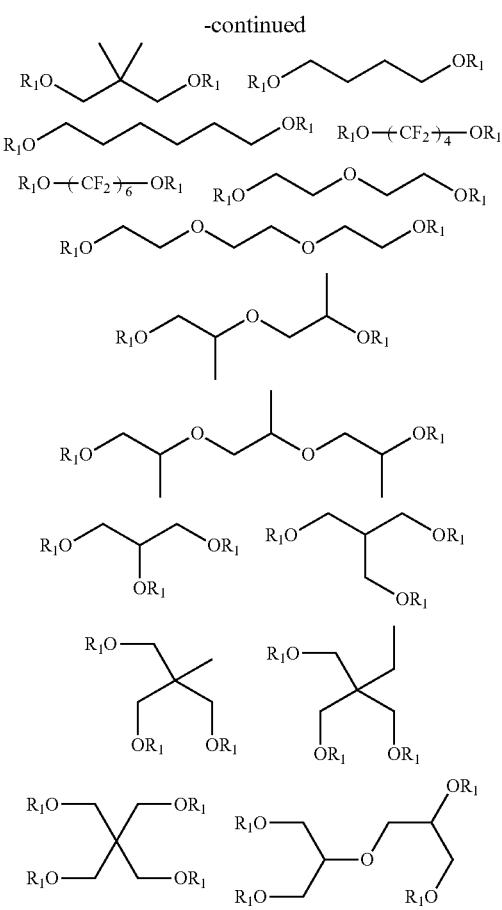

-continued
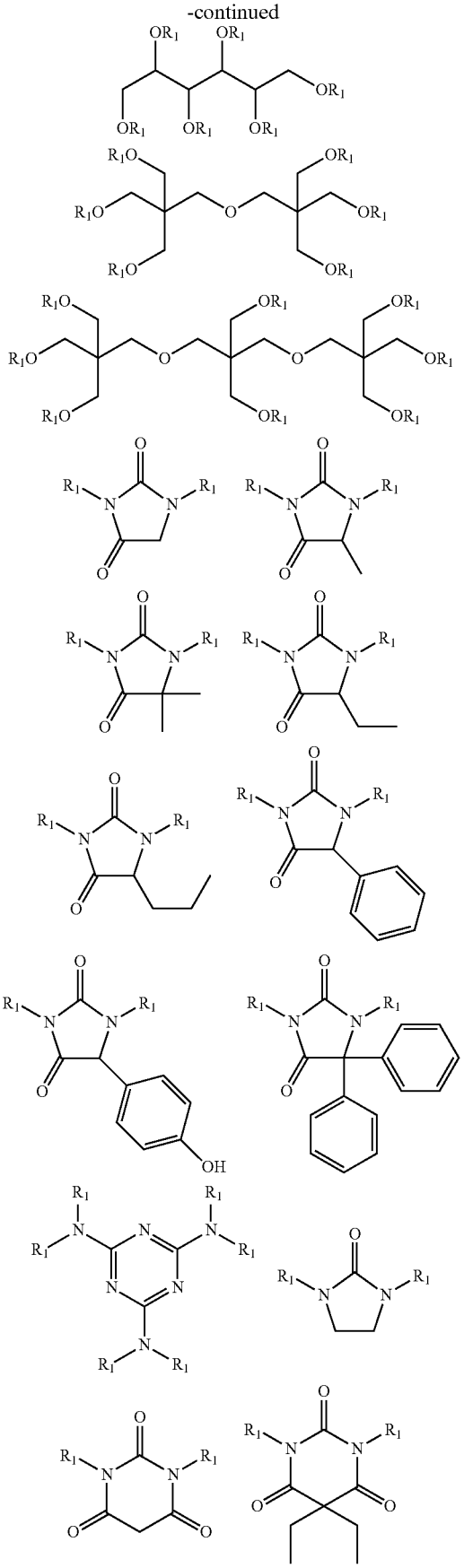
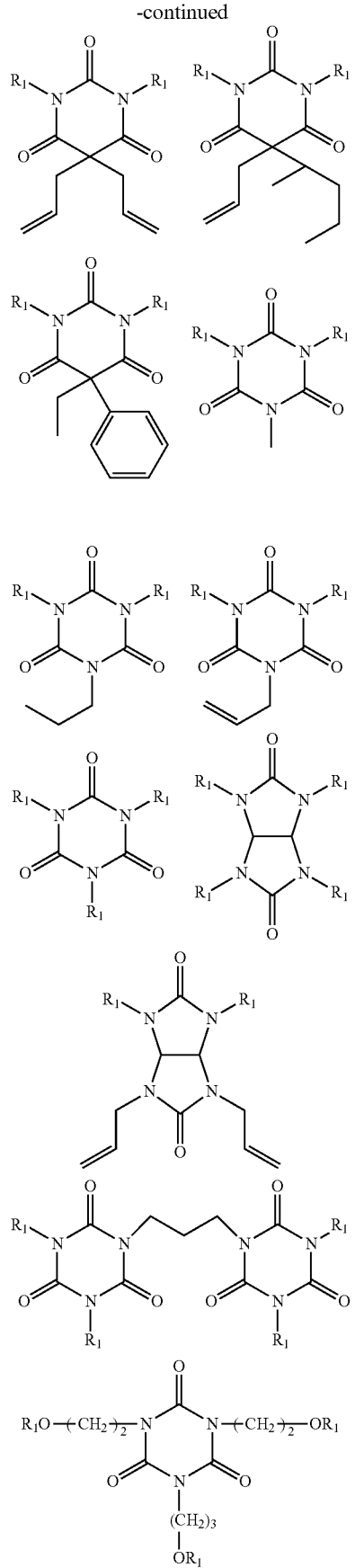

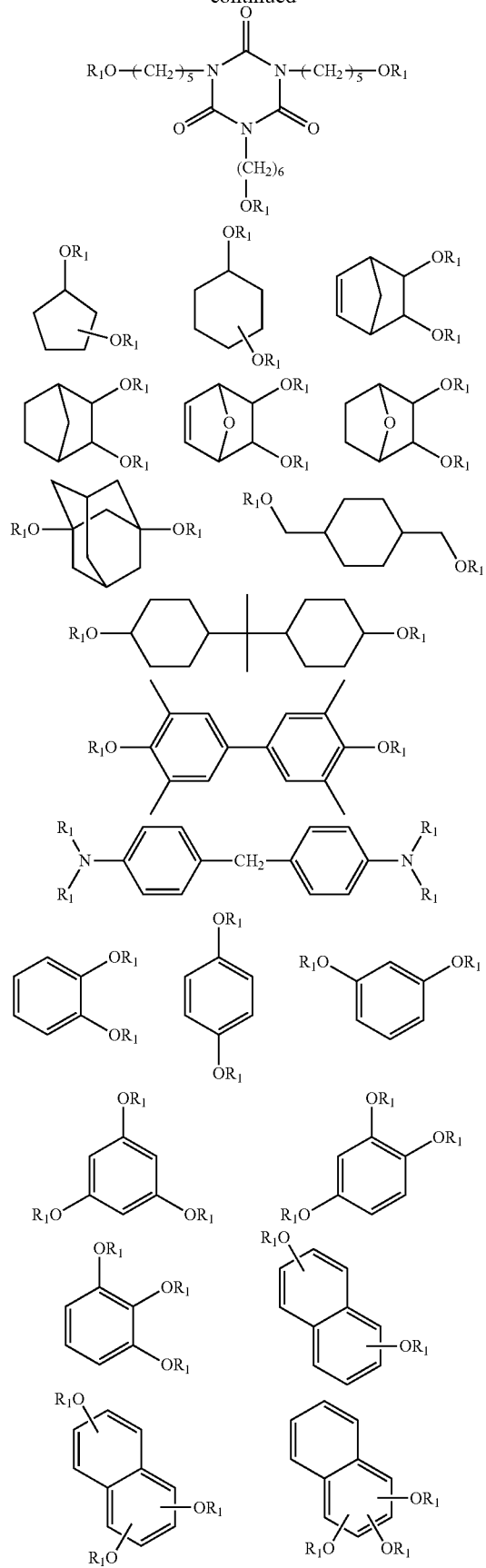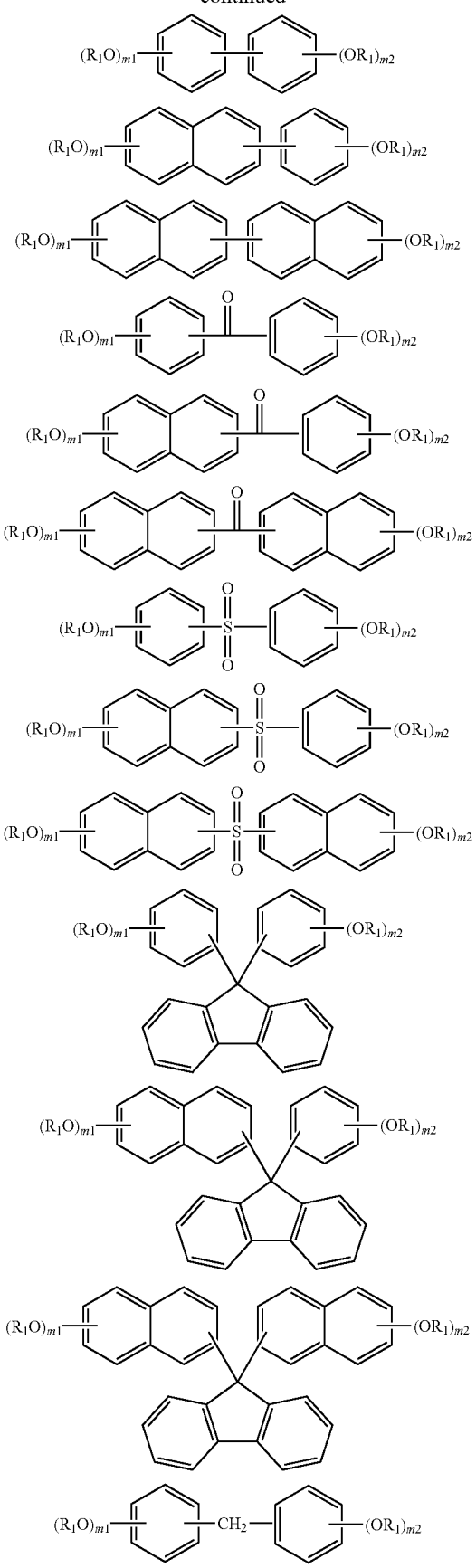

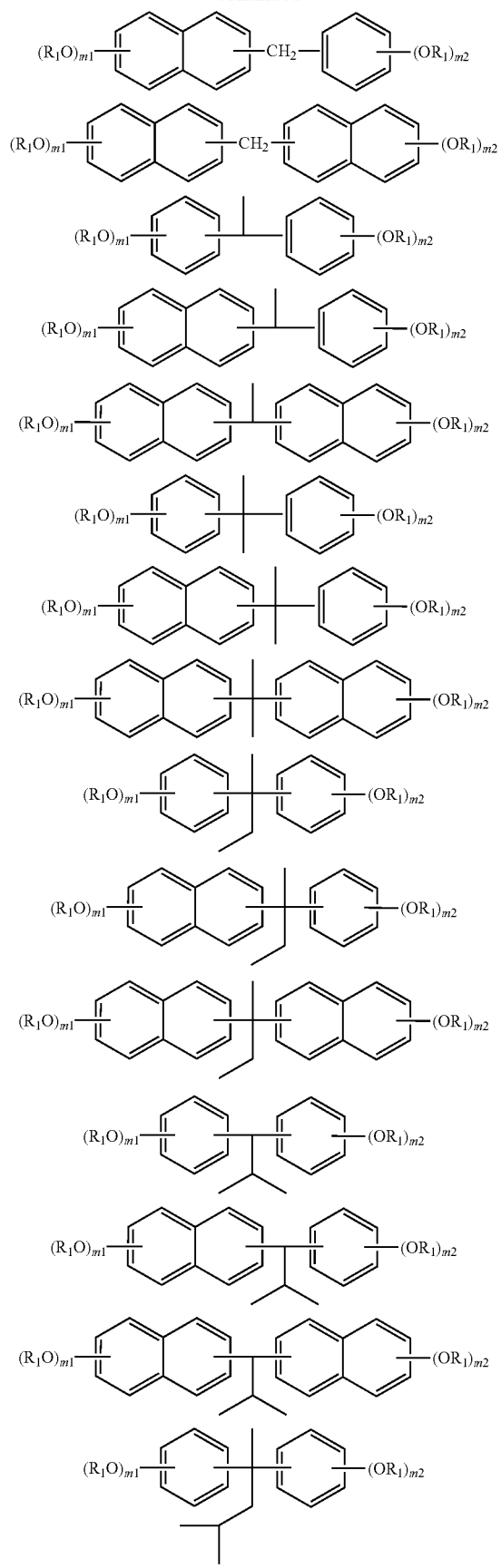
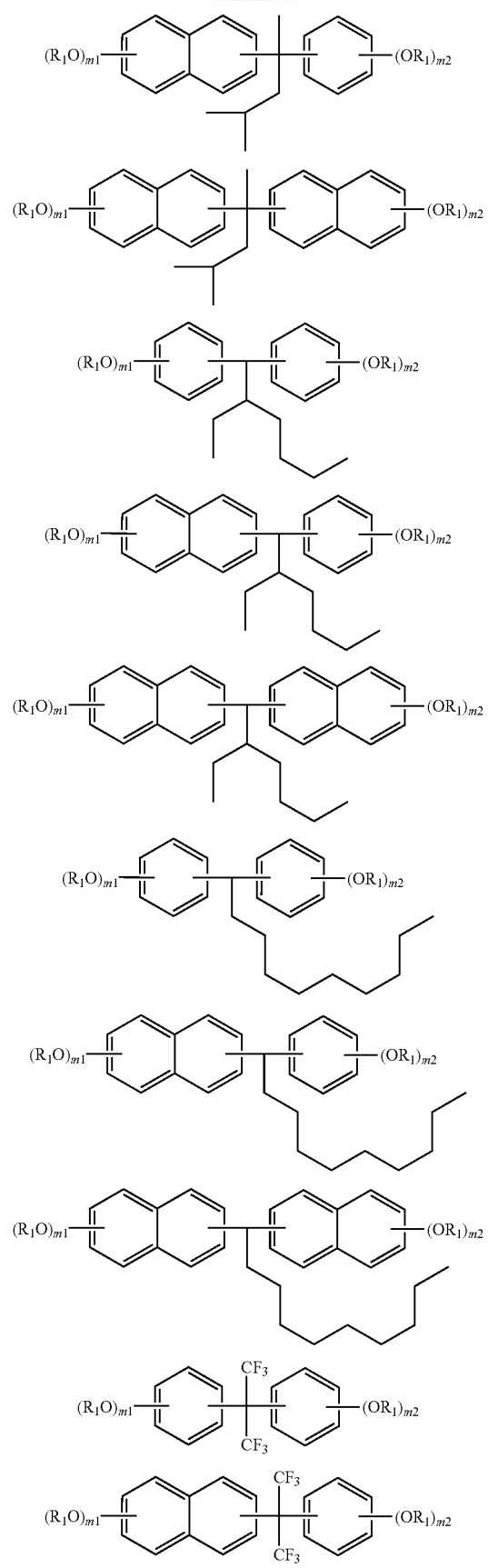

-continued
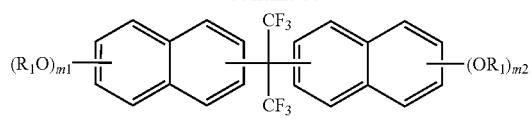
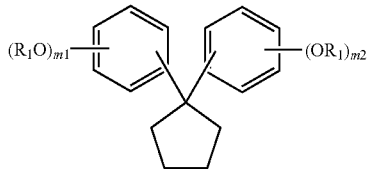
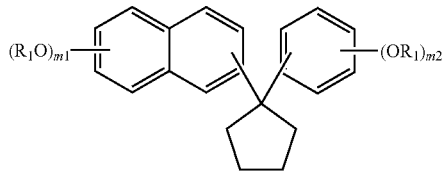
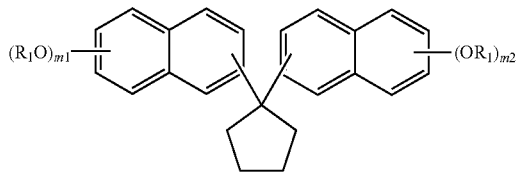
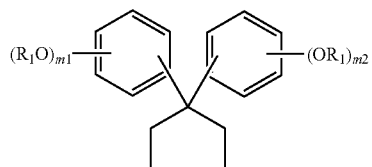
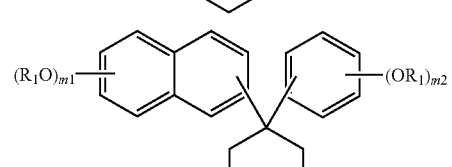
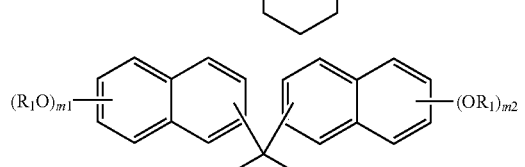
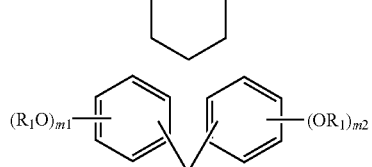
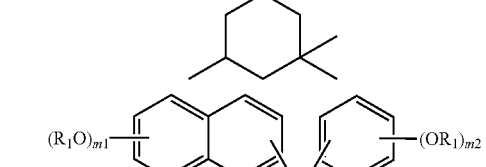
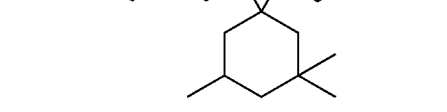
-continued
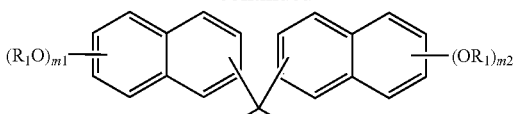
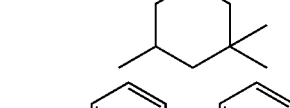
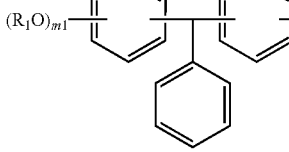
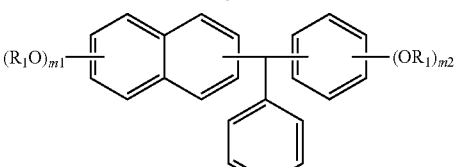
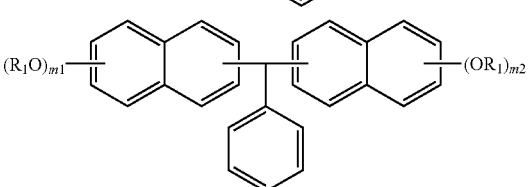
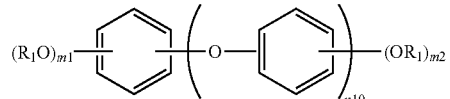
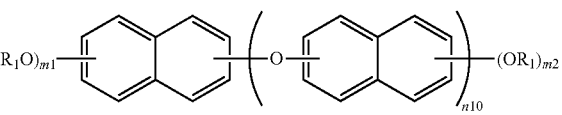
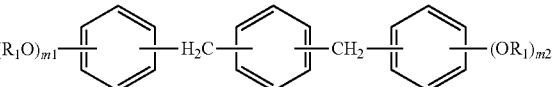
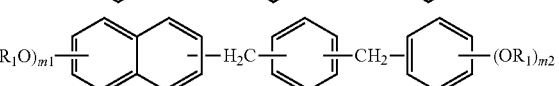
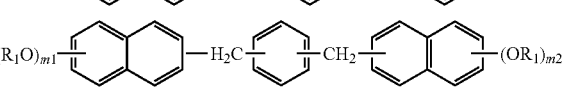
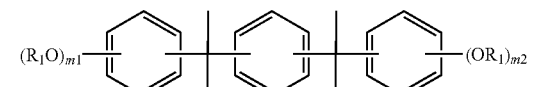
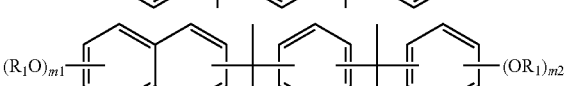
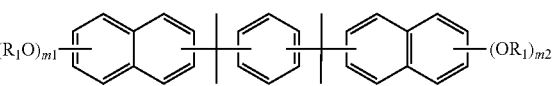
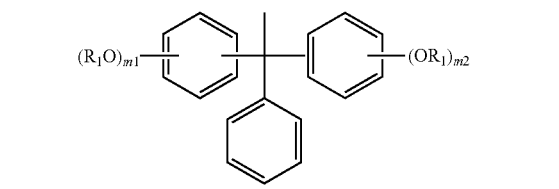

-continued
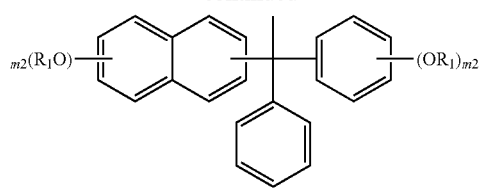
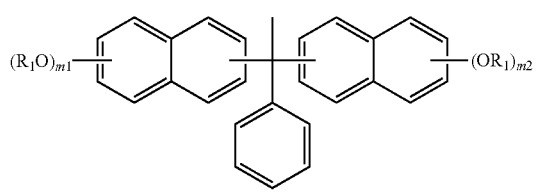
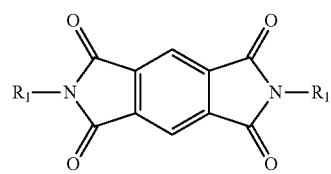
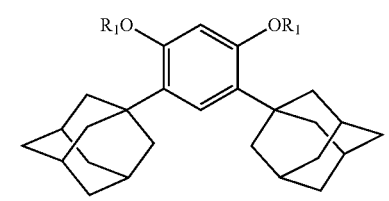
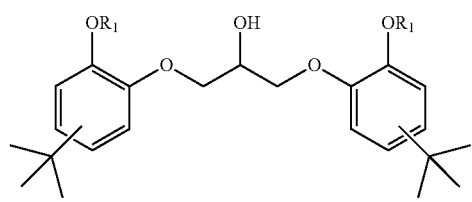
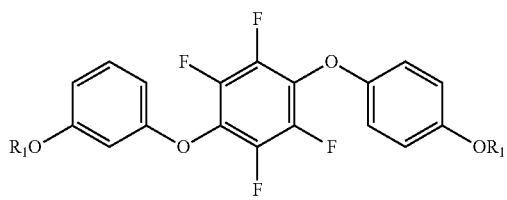
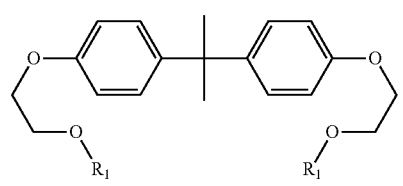
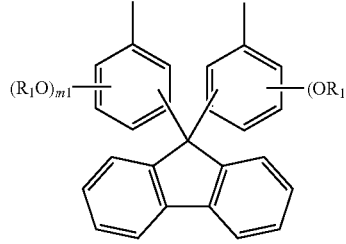
-continued
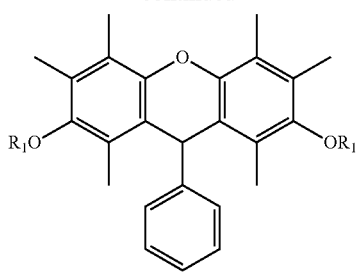
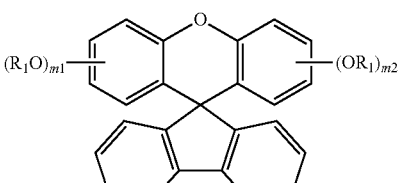
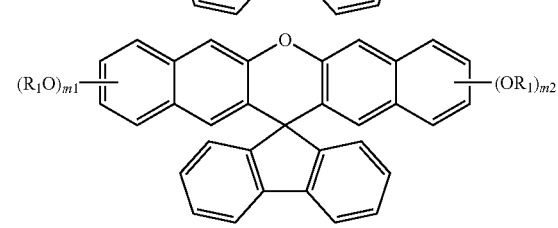
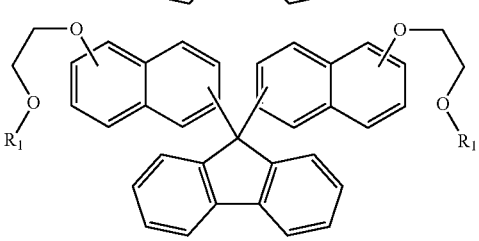
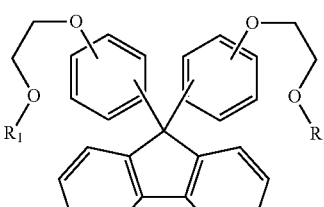
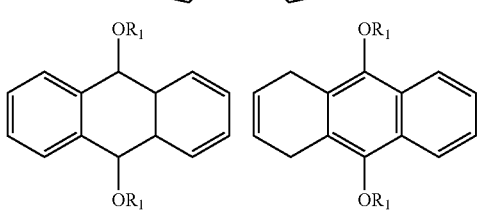
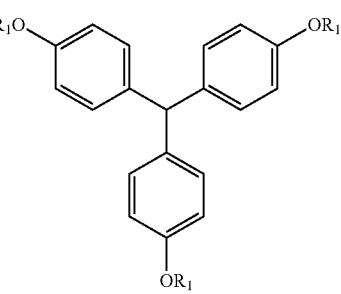

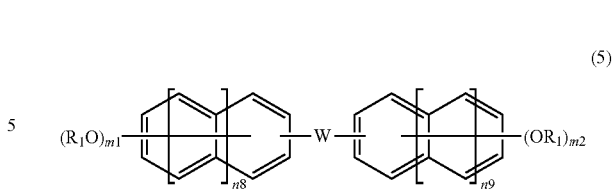

(5)

In the general formula (5), n8 and n9 each independently represent 0 or 1. W is a single bond or any of structures shown by (6) below. $R_1$ is the $R_1$ group. m1 and m2 each independently represent an integer of 0 to 4, and m1+m2 is 1 or more and 8 or less.

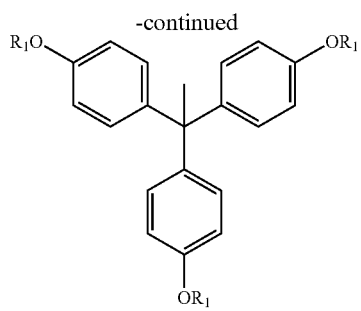

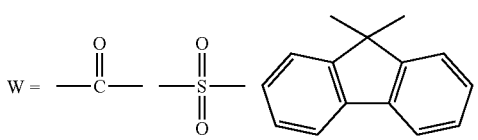

(6)

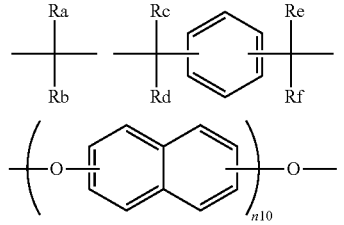

In the general formula (6), n10 represents an integer of 0 to 3. Ra, Rb, Rc, Rd, Re, and Rf each independently represent a hydrogen atom, an alkyl group having 1 to 10 carbon atoms optionally substituted with fluorine, or a phenyl group, and Ra and Rb are optionally bonded to each other to form a cyclic compound.

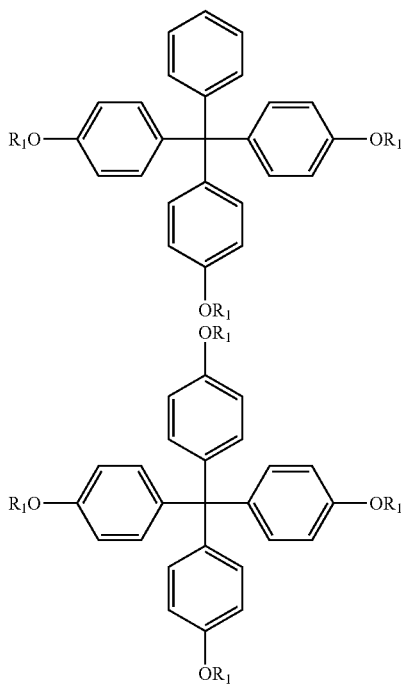

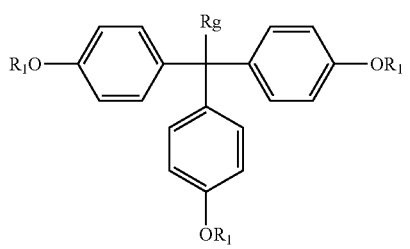

(7)

In the general formula (7), $R_1$ is the $R_1$ group. Rg represents a hydrogen atom, a methyl group, or a phenyl group.

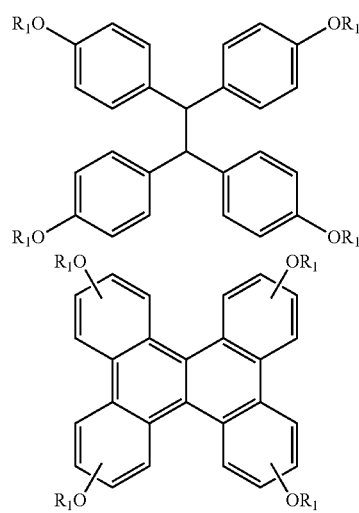

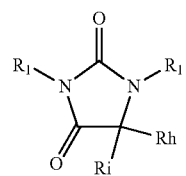

(8)

The organic group X in the general formula (1) is preferably any of the following general formulae (5), (7), (8), (9), (10), (11), (12), (13), (14), and (15).

(9) 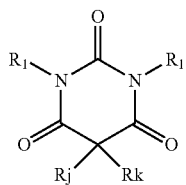

(10) 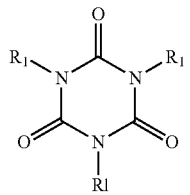

(11) 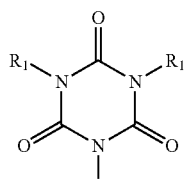

(12) 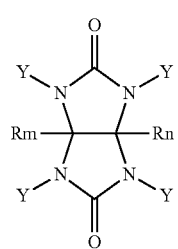

In the general formulae (8) to (12), $R_1$ is the $R_1$ group. Rh, Ri, Rj, Rk, Rl, Rm, and Rn each represent a hydrogen atom, an alkyl group having 1 to 10 carbon atoms, an alkynyl group having 2 to 10 carbon atoms, an alkenyl group having 2 to 10 carbon atoms, a benzyl group optionally having a substituent on an aromatic ring thereof, or a phenyl group. Each Y represents the $R_1$ group, a hydrogen atom, an alkyl group having 1 to 10 carbon atoms, an alkynyl group having 2 to 10 carbon atoms, or an alkenyl group having 2 to 10 carbon atoms. At least two of four Y's in the general formula (12) are the $R_1$ groups.

(13) 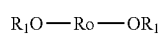

(14) 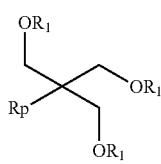

(15) 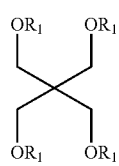

In the general formulae (13) to (15), $R_1$ is the $R_1$ group. Ro represents a linear, branched, or cyclic, saturated or unsaturated hydrocarbon group having 1 to 20 carbon atoms. Rp represents a hydrogen atom or an alkyl group having 1 to 10 carbon atoms.

X shown by the general formula (5) is particularly preferably the following from the viewpoints of heat resistance and etching resistance.

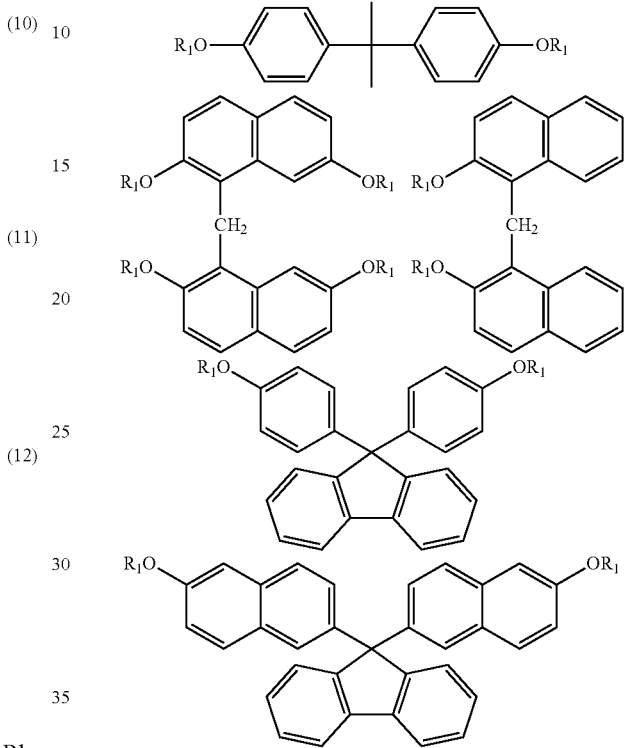

X shown by the general formula (7) is particularly preferably the following from the viewpoints of heat resistance, etching resistance, and curability.

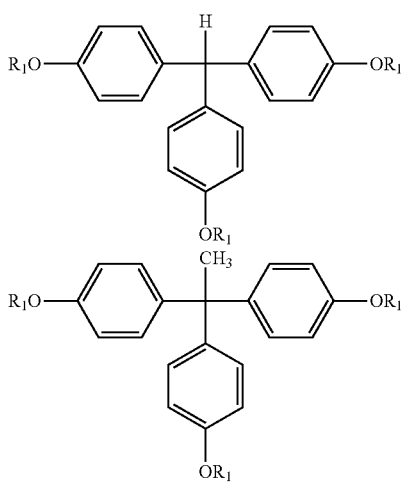

In the present invention, the following compounds are particularly preferable among the general formulae (8) to (12) from the viewpoints of etching resistance, optical properties, and adhesiveness.

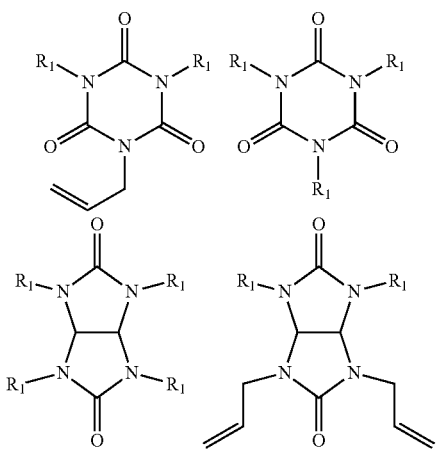

In the present invention, the following compounds are particularly preferable among the general formulae (13) to (15) from the viewpoints of planarizing property, filling property, and adhesiveness.

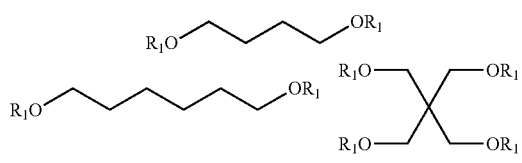

Examples of the terminal group structure shown by the general formula (2) include the following structures and other similar structures. Above all, particularly preferably from the viewpoints of planarizing and filling properties, n2 is 0 and $R_3$ is a hydrogen atom.

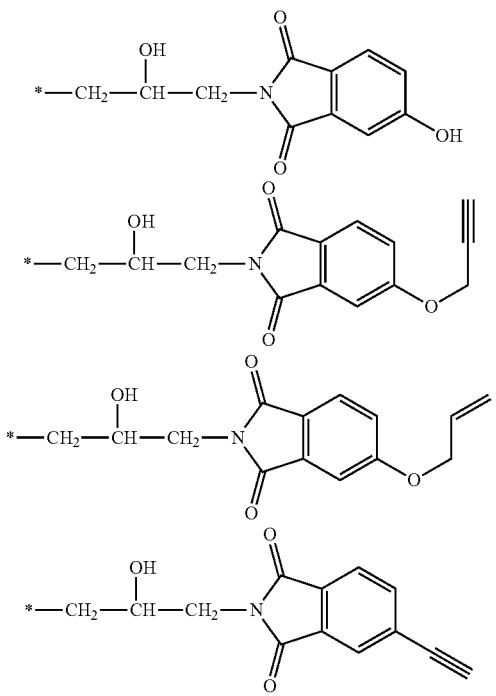

Examples of the terminal group structure shown by the general formula (3) include the following structures and other similar structures. Above all, particularly preferably from the viewpoints of planarizing and filling properties, n5 is 0 and $R_5$ is a hydrogen atom, or n5 is 1 and $R_4$ is a propargyl group.

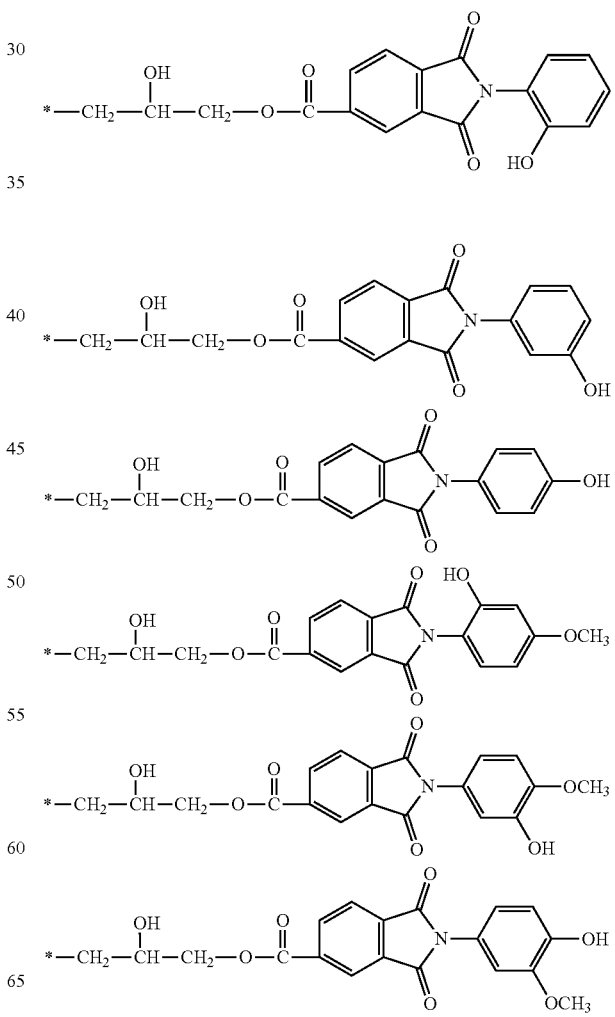

37
-continued
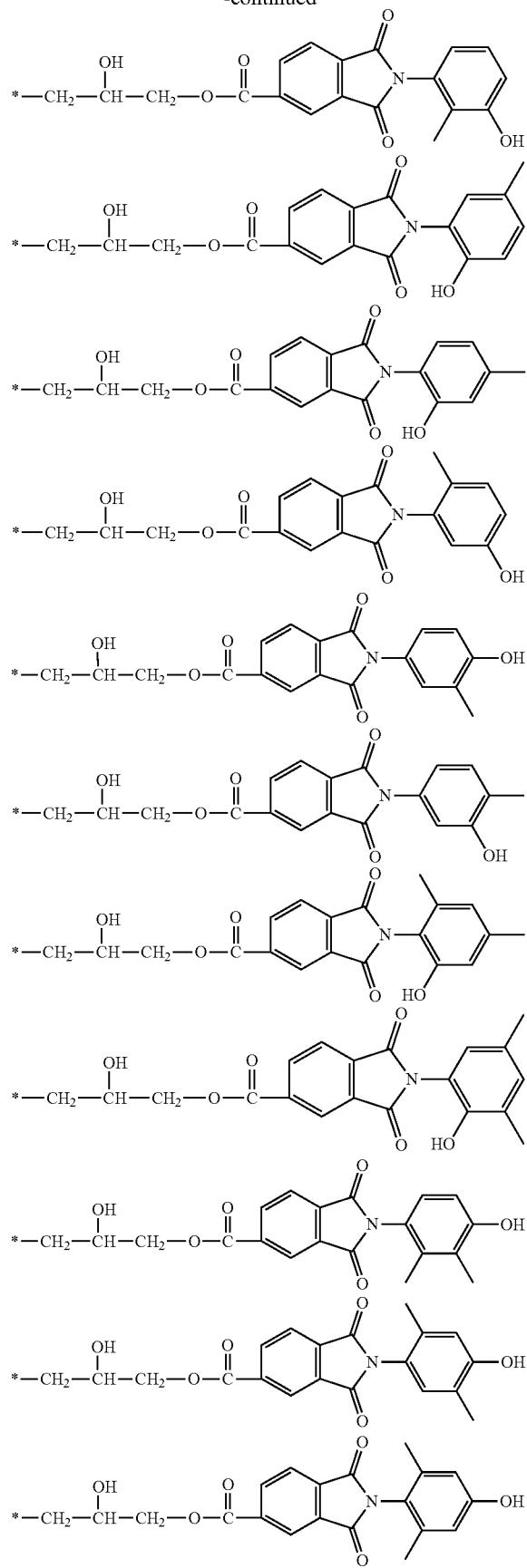
38
-continued
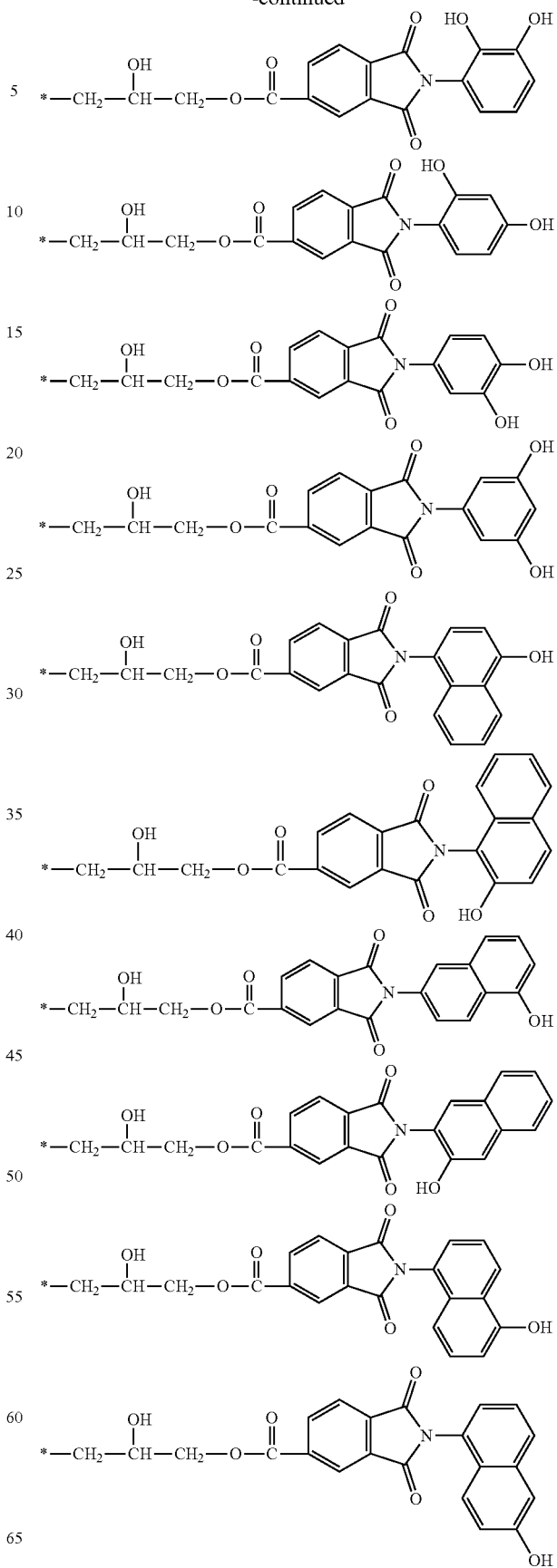

39
-continued
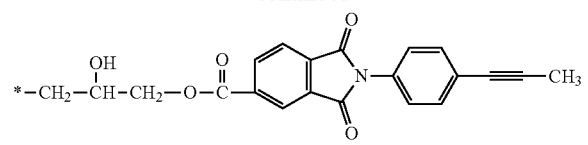
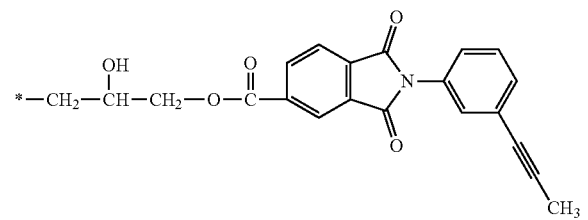
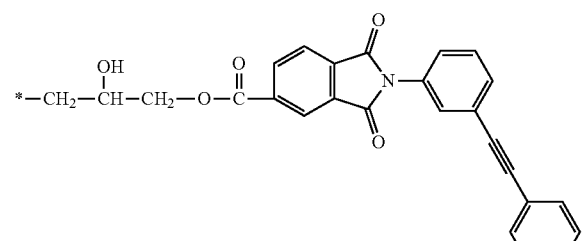
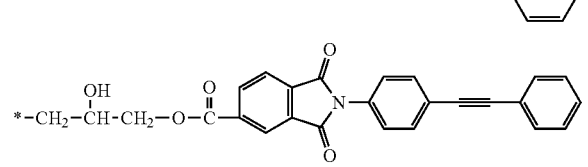
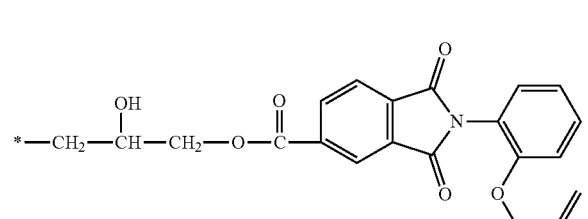
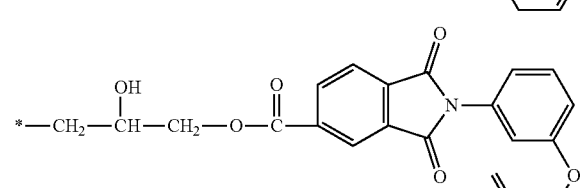
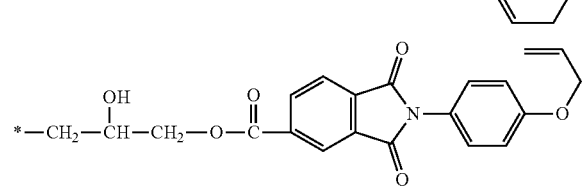
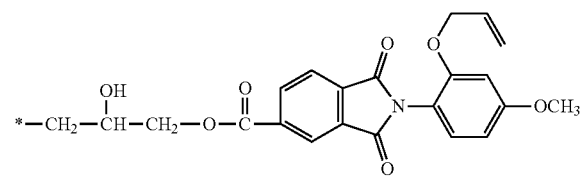
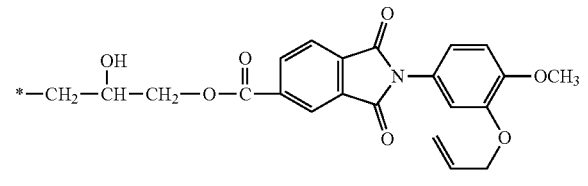
40
-continued
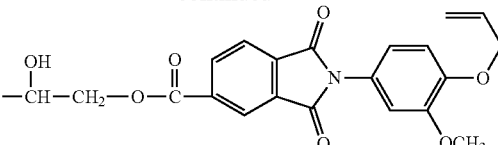
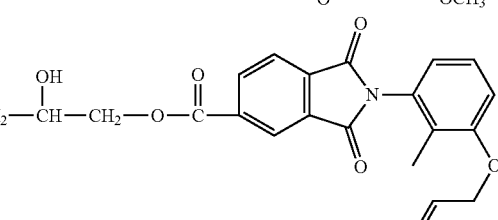
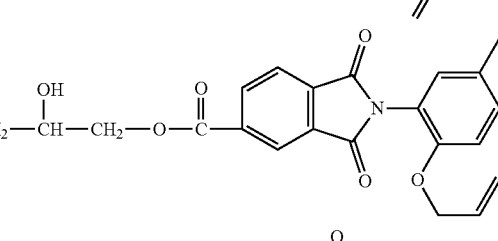
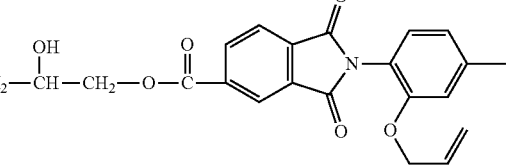
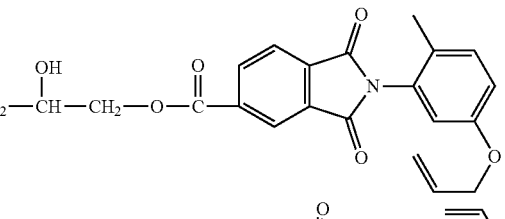
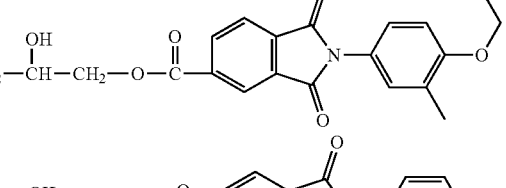
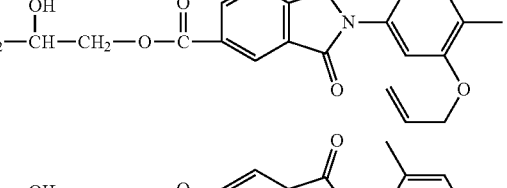
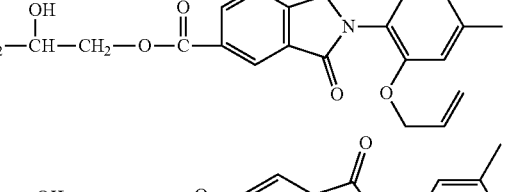
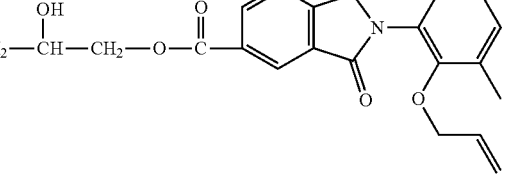

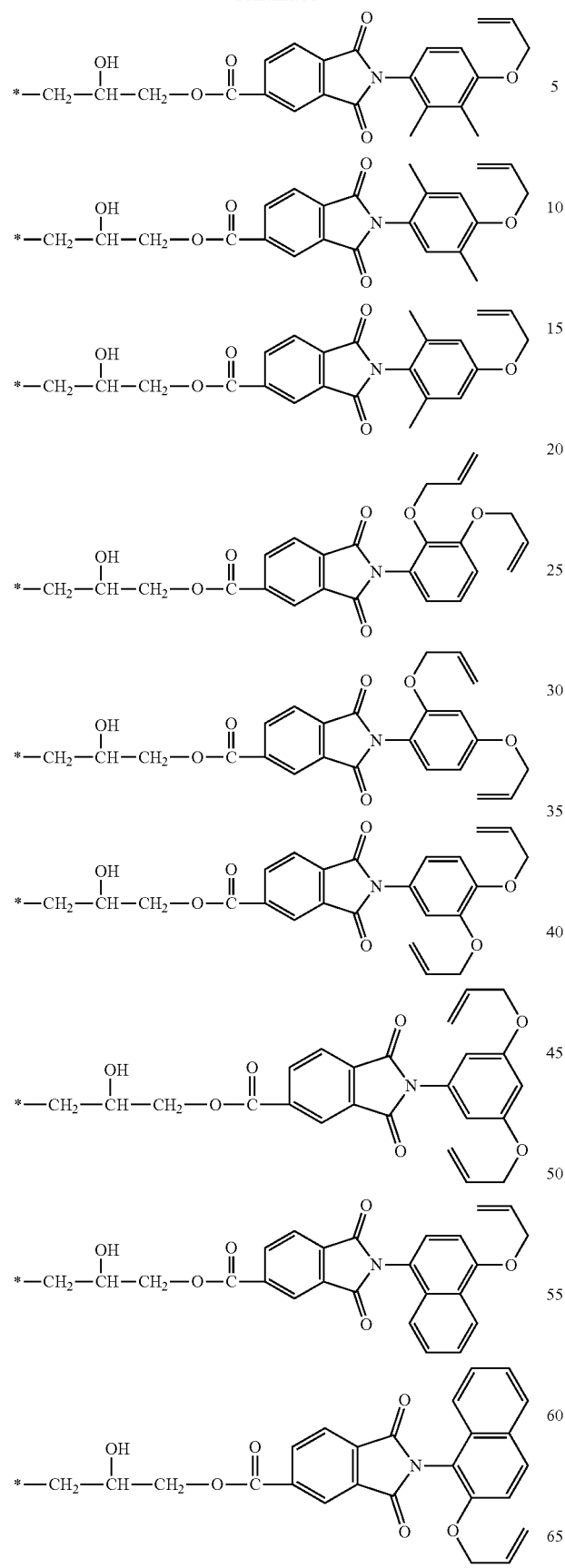
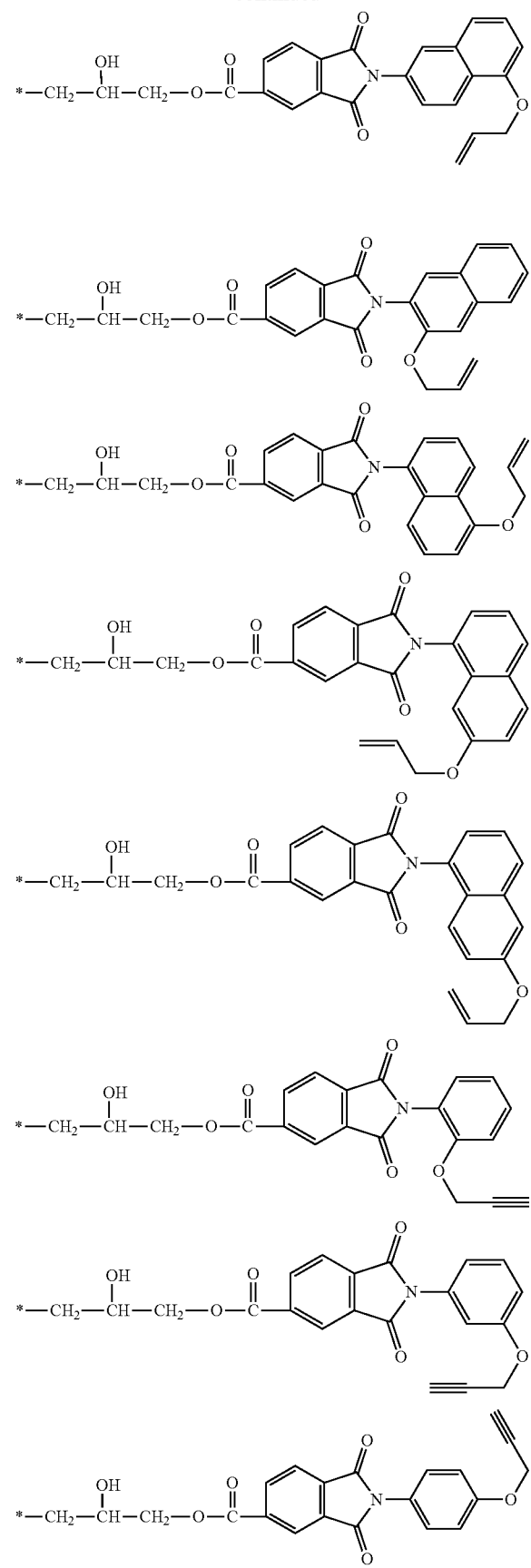

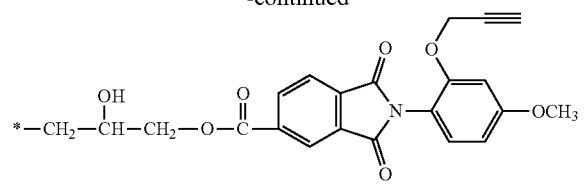
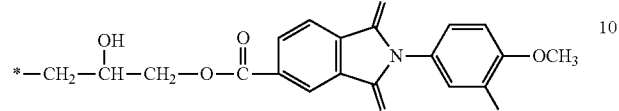
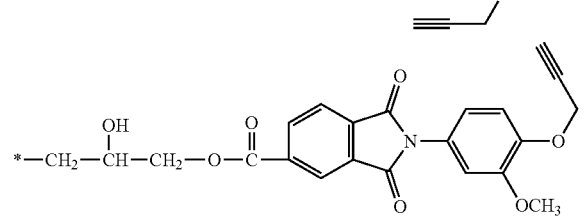
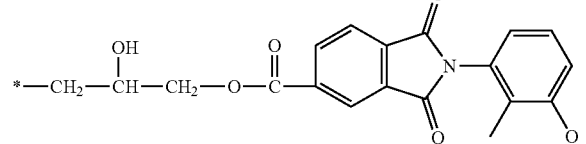
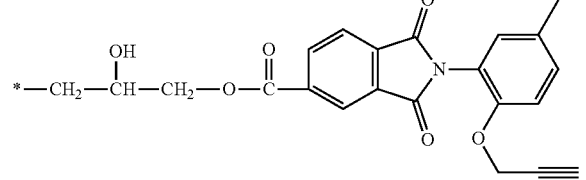
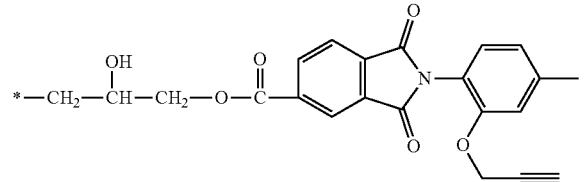
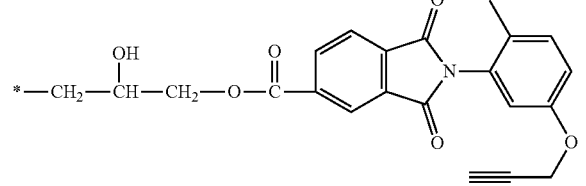
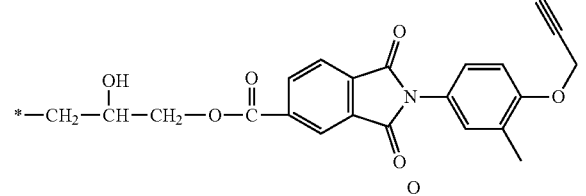
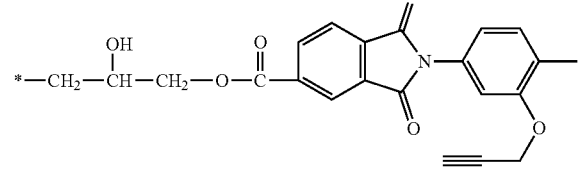
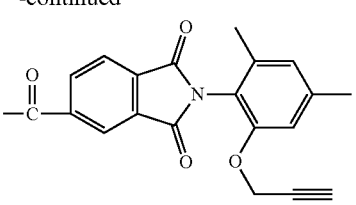

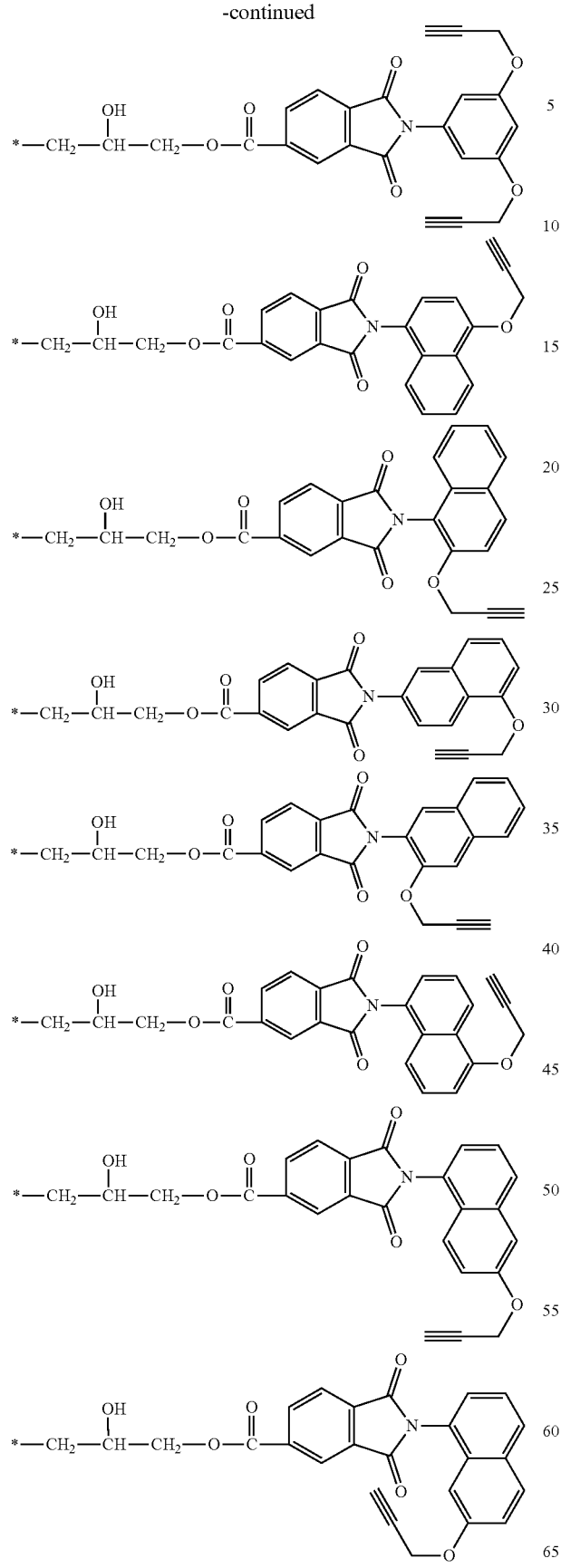
Examples of the terminal group structure shown by the general formula (4) include the following structures and other similar structures. Among the following, terminal group structures having an allyl group or a propargyl group are particularly preferable from the viewpoint of curability.
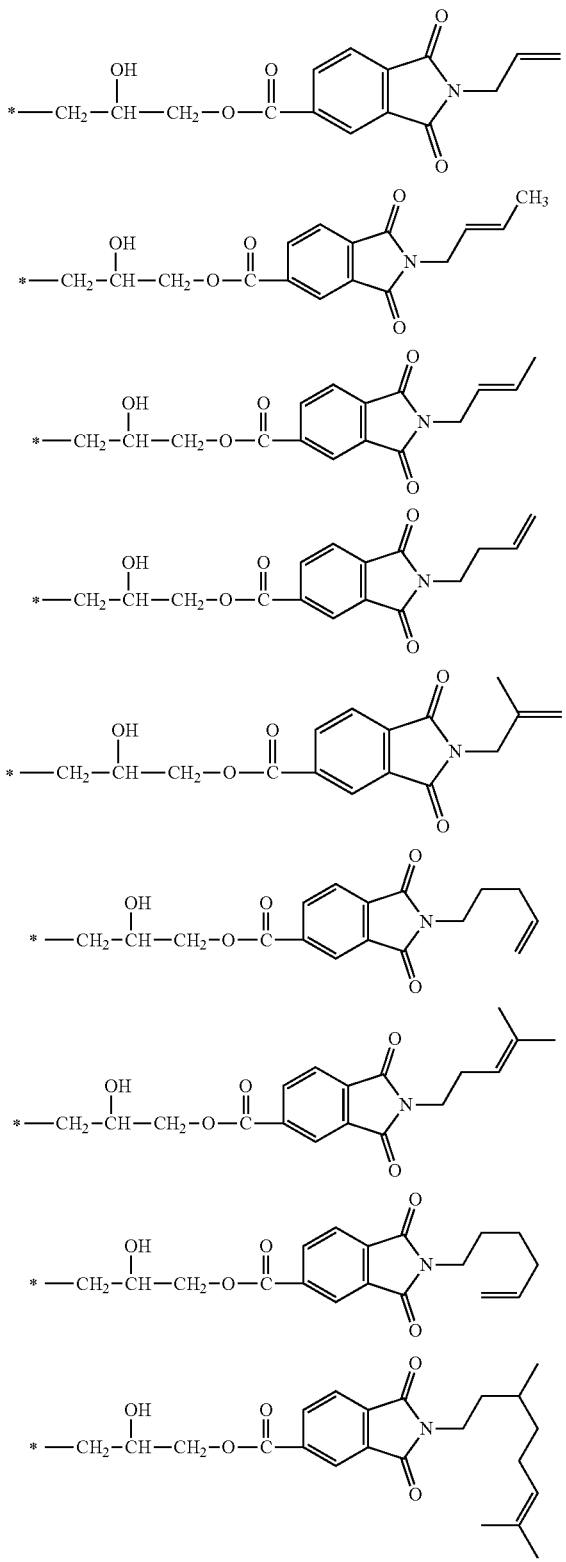

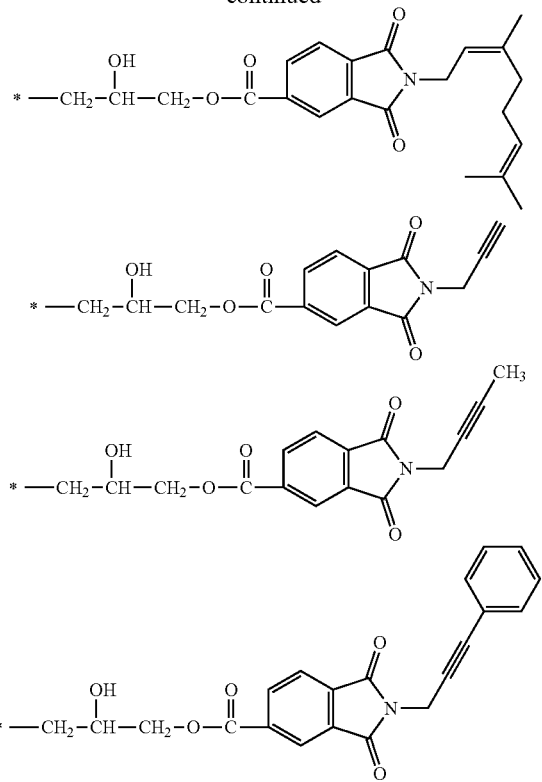

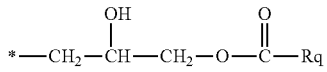

In the general formula (16), Rq represents a linear, branched, or cyclic, saturated or unsaturated hydrocarbon group having 1 to 30 carbon atoms. A methylene group constituting the Rq group is optionally substituted with an oxygen atom or a carbonyl group.

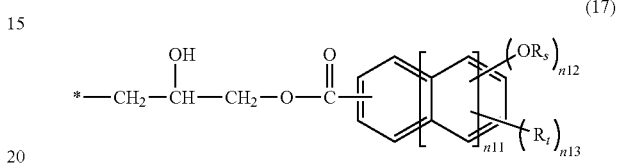

In the general formula (17), Rs represents a hydrogen atom or a linear or branched hydrocarbon group having 1 to 10 carbon atoms. Rt represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms. n11 represents any of 0 to 2. n12 and n13 each represent the number of substituents on an aromatic ring, n12 and n13 each represent an integer of 0 to 7, and n12+n13 is 0 or more and 7 or less.

Further, the $R_1$ group in the general formula (1) can include: any one or more shown by the general formulae (2) to (4); and any one or more shown by the following general formulae (16) and (17).

Examples of the terminal group structure shown by the general formula (16) include the following structures and other similar structures. In the following formulae, n14 represents an integer of 0 to 30, and n15 represents 0 to 20.

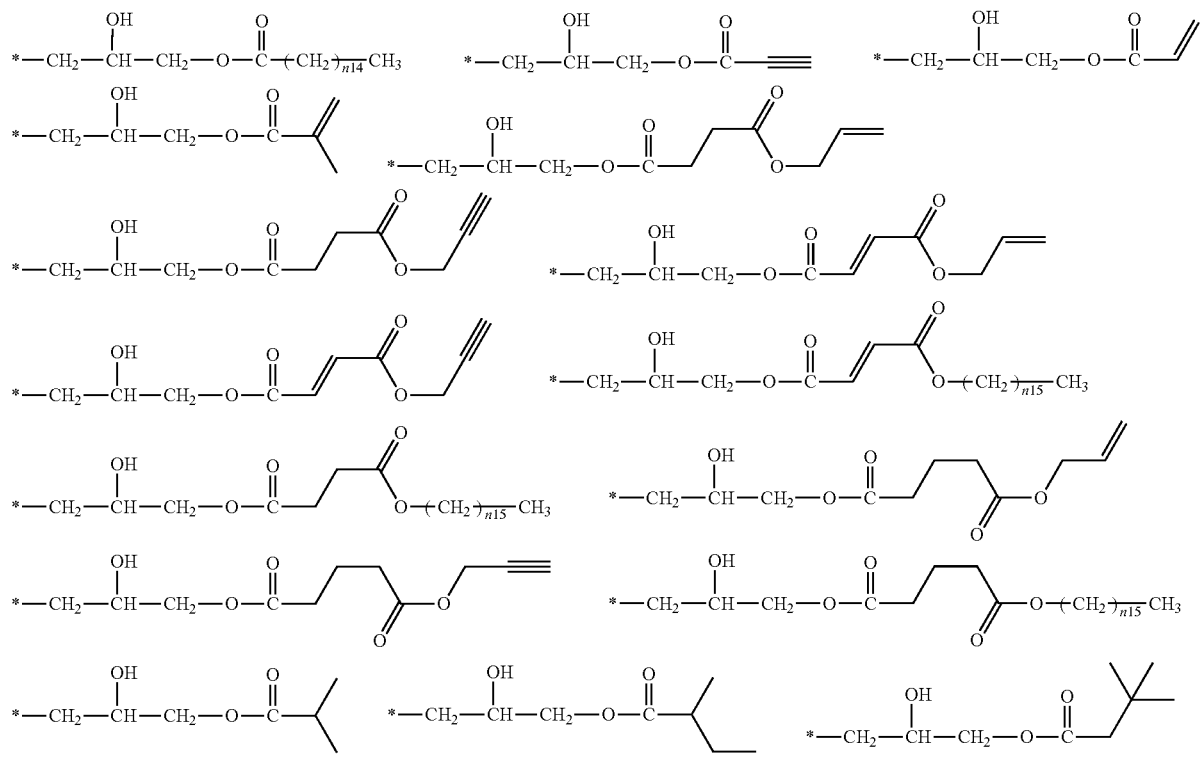

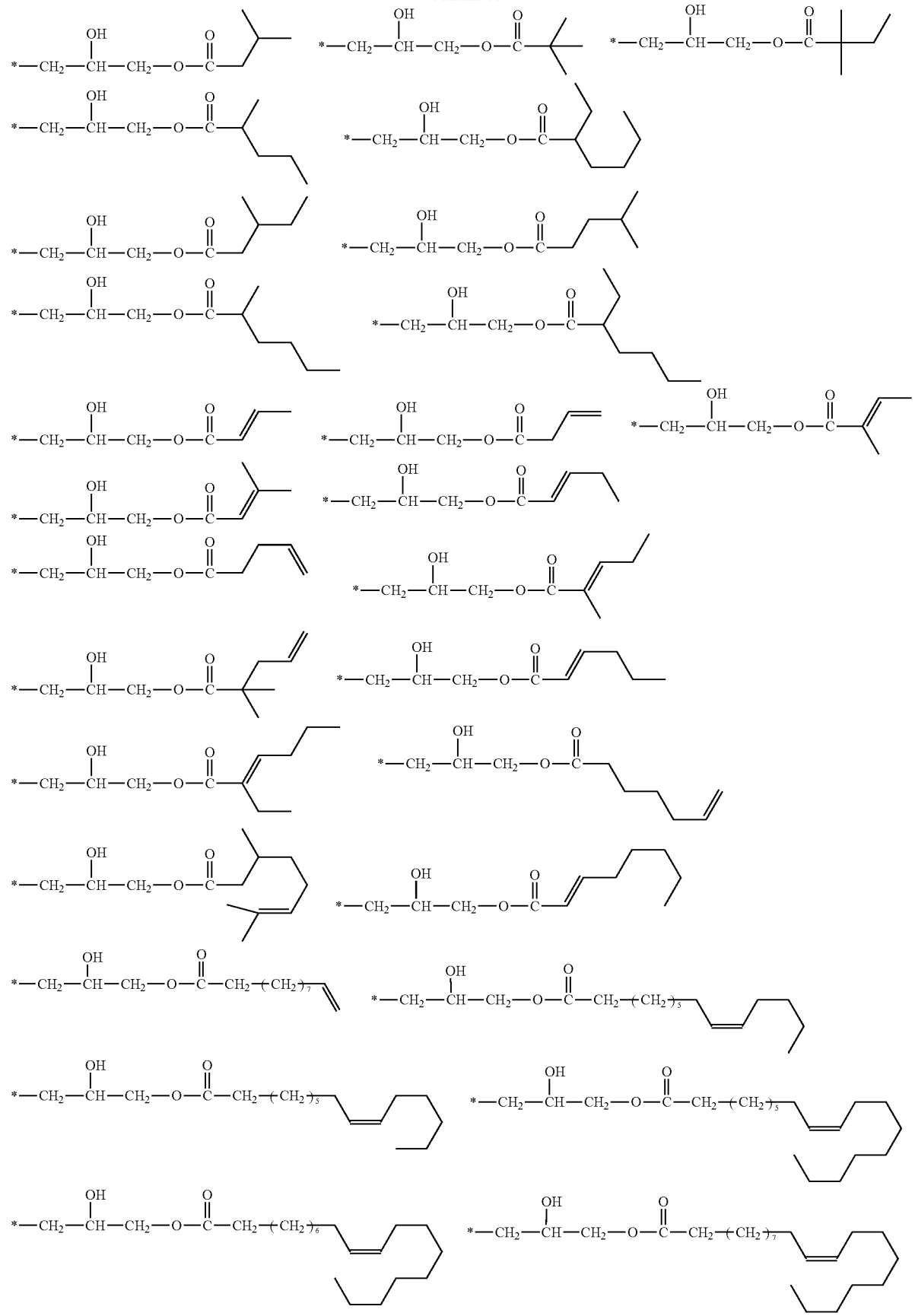

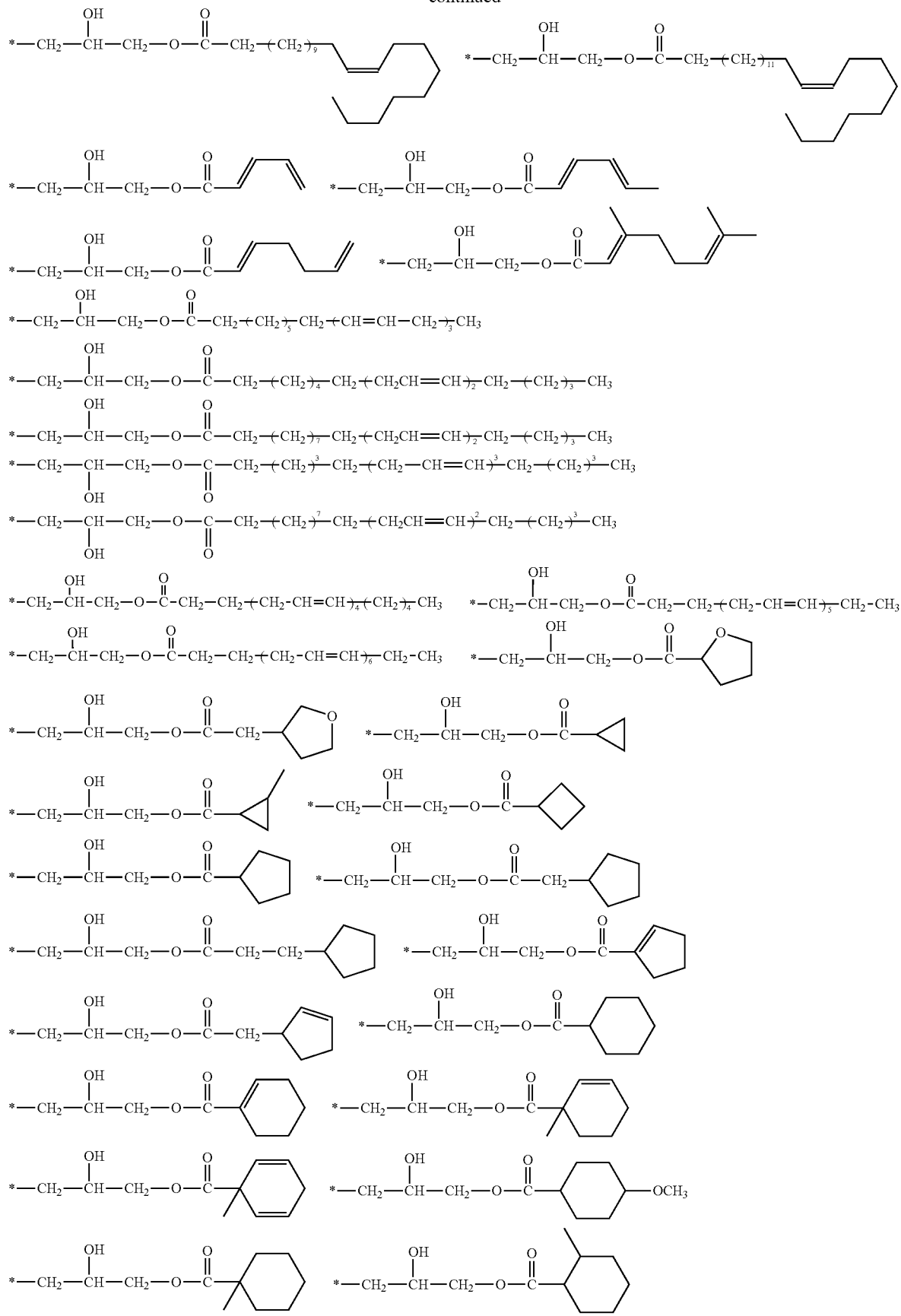

-continued
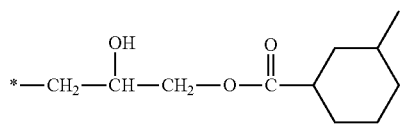 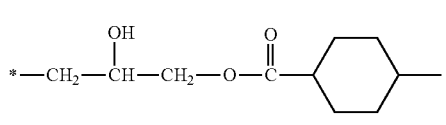
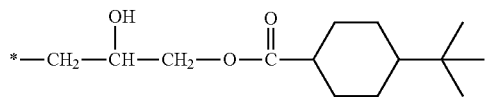 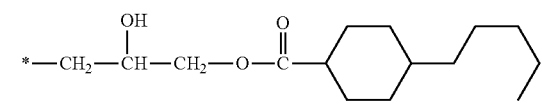
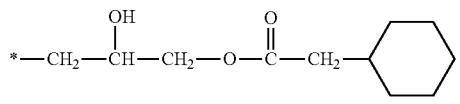 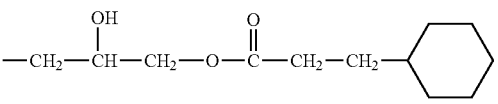
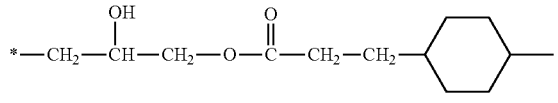 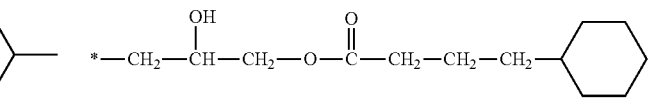
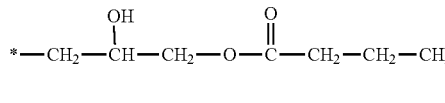 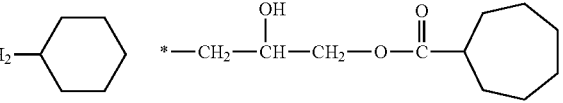
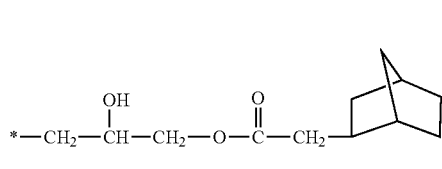 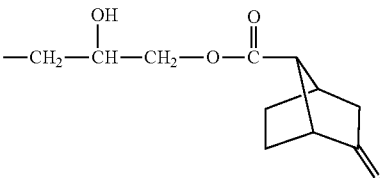
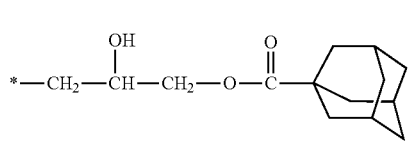 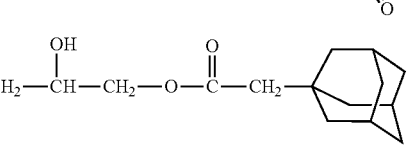
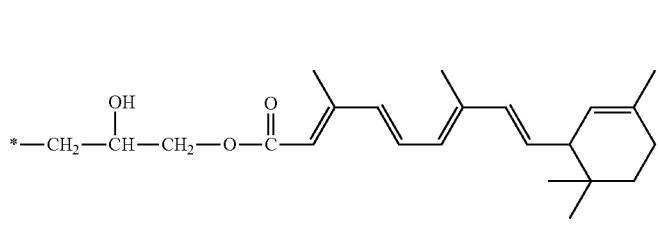 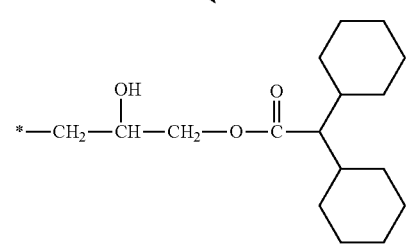
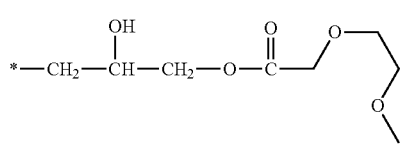 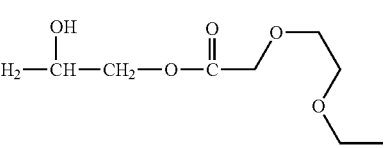
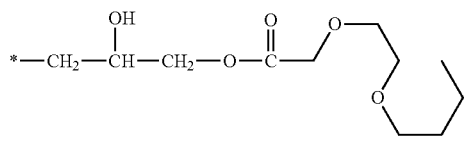 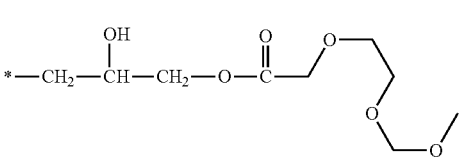
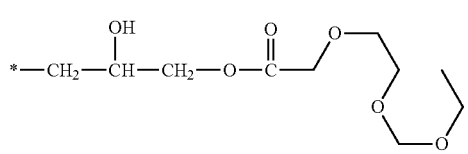 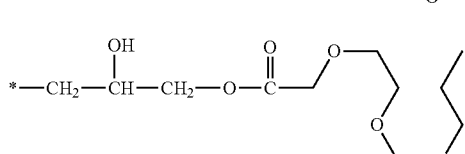

Examples of the terminal group structure shown by the general formula (17) include the following structures and other similar structures. In the following formulae, n16 represents an integer of 0 to 9.
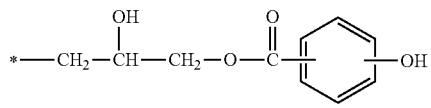
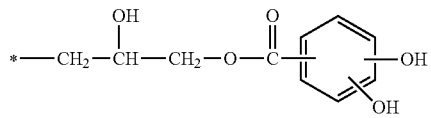
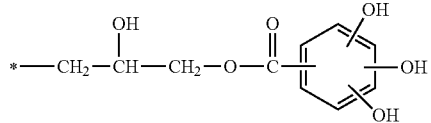
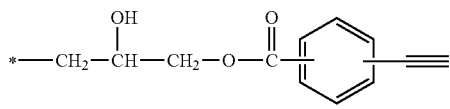
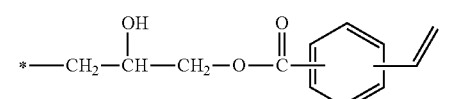
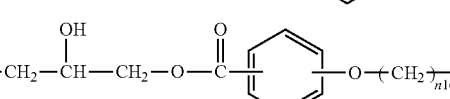
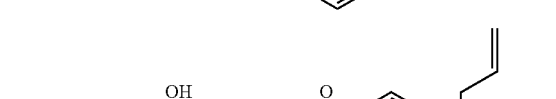
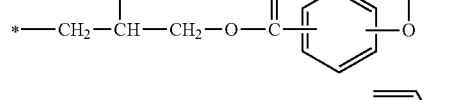
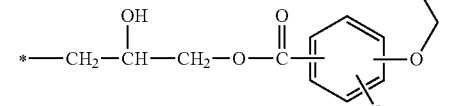
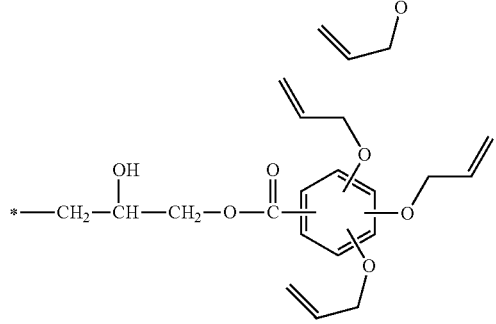
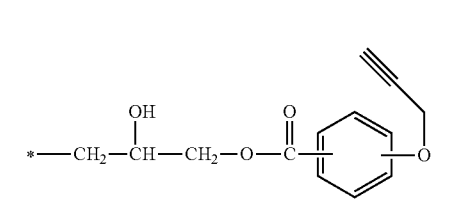
-continued
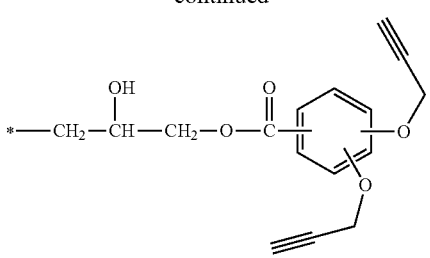
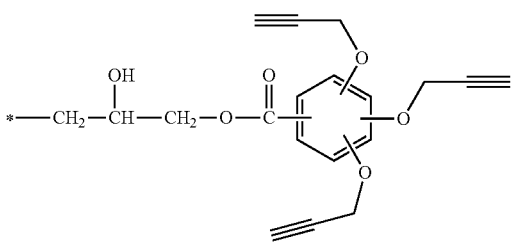
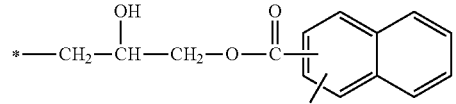
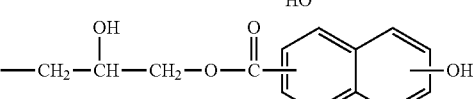
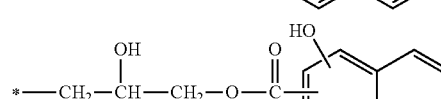
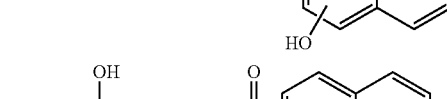
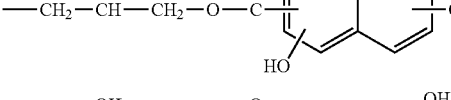
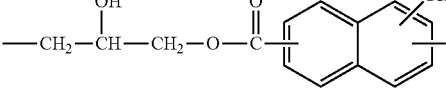
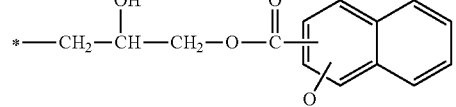
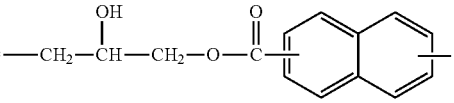
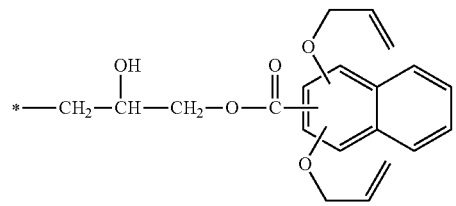

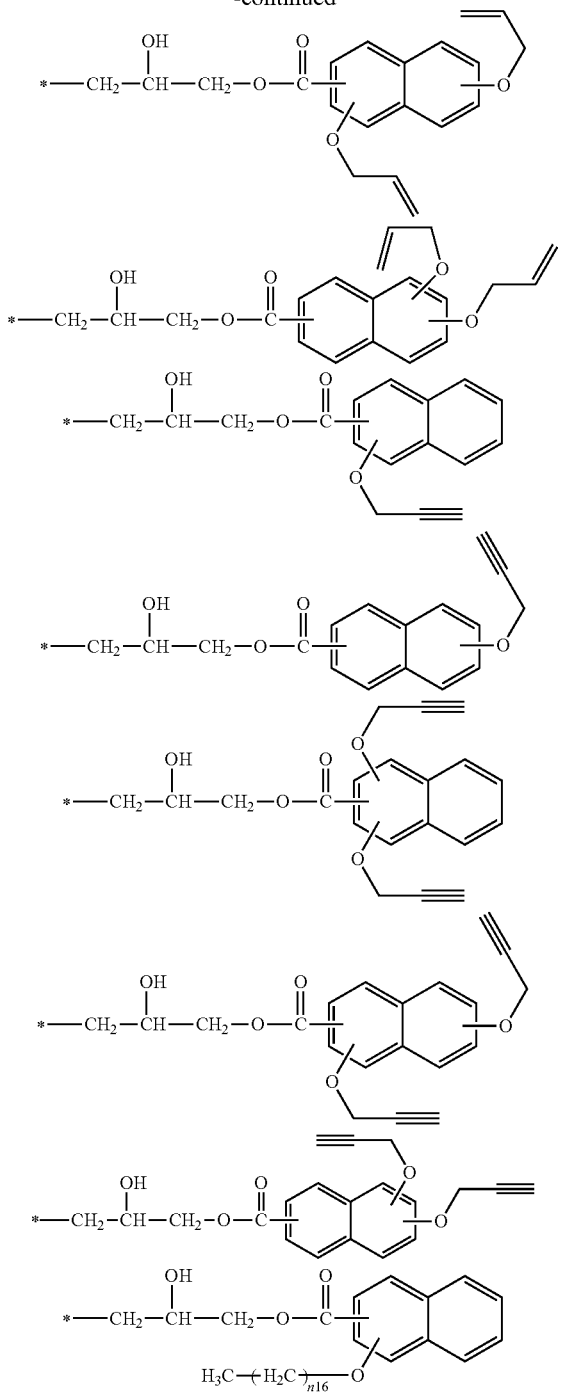

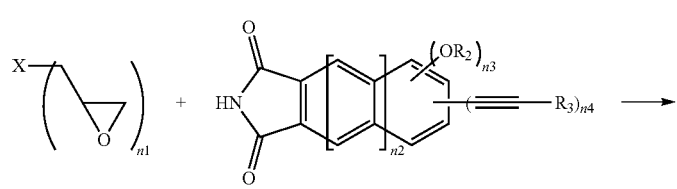

When these compounds are incorporated in materials for forming an organic film, the combination of the terminal group structures enables adjustment of various properties such as heat resistance, etching resistance, filling property, planarizing property, and adhesive force to a substrate, in accordance with the required performances. Moreover, the optical constant (n/k) can also be controlled. Thus, particularly, at exposure in multilayer ArF lithography, it is possible to impart appropriate optical constant, suppress reflection light, and attain excellent resolution.

Note that the inventive compound for forming an organic film preferably has a molecular weight of 2,500 or less. With such a molecular weight, the resulting material for forming an organic film has more favorable thermal flowability. Accordingly, the composition including the inventive compound can not only favorably fill a fine structure formed on a substrate, but also form an organic film while planarizing the entire substrate. Note that the molecular weight can be determined as a weight-average molecular weight (Mw) in terms of polystyrene by gel permeation chromatography (GPC) using tetrahydrofuran as an eluent.

When the material for forming an organic film contains such a compound and used as a resist underlayer film material to form a multilayer resist film that is applied to fine processing in processes of manufacturing semiconductor devices and the like, there can be provided: a resist underlayer film material for forming a resist underlayer film that has all of high filling property, high planarizing property, and excellent adhesive force to a substrate; a method for forming such a resist underlayer film; and a patterning process. The present invention also makes it possible to provide a planarizing material for manufacturing semiconductor devices, the planarizing material having excellent filling property, planarizing property, and adhesive force to a substrate, and being applicable to planarization in semiconductor device manufacturing processes other than multilayer resist processes.

[Compound Production Method]

The compound used in the inventive material for forming an organic film can be produced by selecting an optimum method depending on the structure. Hereinafter, an exemplary method for synthesizing the compound shown by the general formula (1) will be described in detail. Note that the method for producing the compound of the material for forming an organic film is not limited thereto.

As illustrated in (18) to (20) below, the synthesis is possible by addition reaction between an epoxy compound and a phthalimide compound or carboxylic acid compound having an imide group. In the following formulae, X, n1, n2, n3, n4, n5, n6, n7, $R_2$, $R_3$, $R_4$, $R_5$, and $R_6$ are as defined above.

(18)

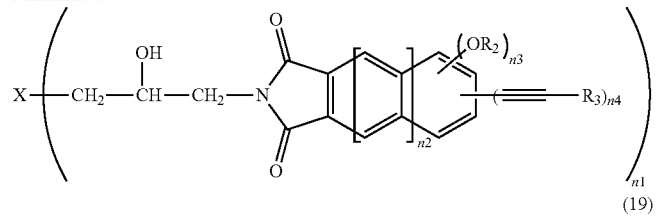

(19)

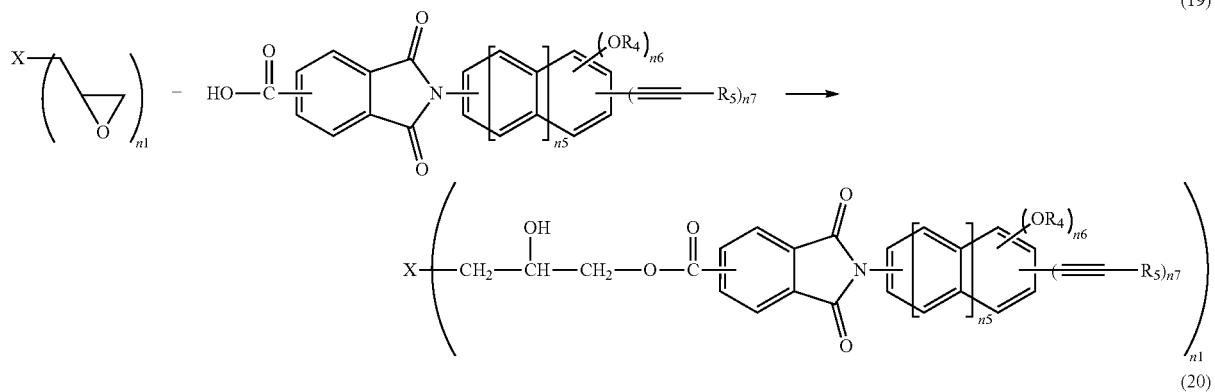

(20)

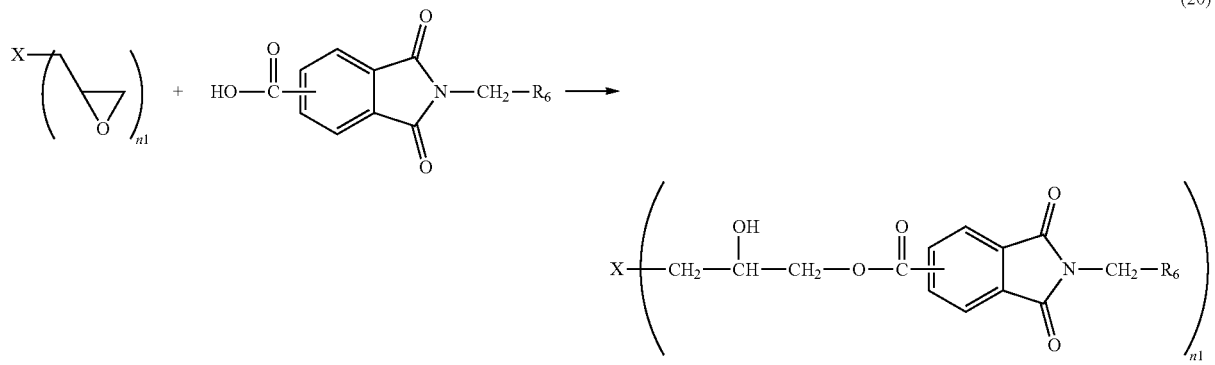

The amount ratio of the epoxy compound and the phthalimide compound or carboxylic acid compound having an imide group is preferably such that the amount of carboxyl groups in the phthalimide compound or carboxylic acid compound is preferably 0.3 to 2.0 mol, more preferably 0.5 to 1.5 mol, further preferably 0.75 to 1.25 mol, relative to 1 mol of epoxy groups in the epoxy compound. When the amount of the phthalimide compound or carboxyl groups is appropriate relative to the amount of the epoxy groups as above, the storage stability of the material for forming an organic film will not be lowered due to the residue of unreacted epoxy groups, and the residue of unreacted phthalimide compound or carboxylic acid compound having an imide group can be prevented from outgassing.

Additionally, to improve the required performances such as, for example, optical constant (n/k), thermal flowability, etching resistance, heat resistance, solvent solubility, and adhesiveness, multiple epoxy compounds or multiple phthalimide compounds or multiple carboxylic acid compounds having imide groups may be used in combination. Note that, in this case also, the amount ratio of epoxy groups and the phthalimide compound or carboxyl groups is preferably within the above-described ranges.

The compound used in the inventive material for forming an organic film can be obtained generally by reacting the epoxy compound and the phthalimide compound or carboxylic acid compound having an imide group in the presence of a reaction catalyst without a solvent or in a solvent, at room temperature or under cooling or heating as necessary.

Specific examples of the solvent used in this event include alcohols such as methanol, ethanol, isopropyl alcohol, butanol, ethylene glycol, propylene glycol, diethylene glycol, glycerol, methyl cellosolve, ethyl cellosolve, butyl cellosolve, and propylene glycol monomethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate; lactones such as γ-butyrolactone; and non-protic polar solvents such as dimethylsulfoxide, N,N-dimethylformamide, and hexamethylphosphoric triamide. One of these or a mixture of two or more thereof can be used. These solvents are preferably used in an amount ranging from 0 to 2,000 parts by mass based on 100 parts by mass of the reaction raw materials.

Specific examples of the reaction catalyst include quaternary ammonium salts such as benzyltriethylammonium chloride, benzyltriethylammonium bromide, benzyltrimethylammonium chloride, tetramethylammonium chloride, tetramethylammonium bromide, tetramethylammonium iodide, tetramethylammonium hydroxide, tetraethylammonium bromide, tetrabutylammonium chloride, tetrabutylammonium bromide, tetrabutylammonium iodide, tetrabutylammonium hydrogen sulfate, trioctylmethylammonium chloride, tributylbenzylammonium chloride, trimethylbenzylammonium chloride, trimethylbenzylammonium hydroxide, N-laurylpyridinium chloride, N-lauryl-4-picolinium chloride, N-laurylpicolinium chloride, trimethylphenylammonium bromide, and N-benzylpicolinium chloride; quaternary phosphonium salts such as tetrabutylphosphonium chloride, tetrabutylphosphonium bromide, and tetraphenylphosphonium chloride; tertiary amines such as tris[2-(2-methoxyethoxy)ethyl]amine, tris (3,6-dioxaheptyl)amine, and tris(3,6-dioxaoctyl)amine; etc. The amount of the catalyst to be used is in a range of preferably 0.001 to 100 mass %, more preferably 0.005 to 50 mass %, with respect to the raw materials. The reaction temperature is preferably about −50° C. to the boiling point of the solvent, more preferably room temperature to 150° C. The reaction time is appropriately selected within a range of 0.1 to 100 hours.

The reaction method include, for example, a method in which the epoxy compound, the phthalimide compound or carboxylic acid compound having an imide group, and a catalyst are charged at once; a method in which the epoxy compound and the phthalimide compound or carboxylic acid compound having an imide group are dispersed or dissolved in a solvent, and then a catalyst is added at once thereto or diluted with a solvent and added dropwise thereto; and a method in which a catalyst is dispersed or dissolved in a solvent, and then the epoxy compound and the phthalimide compound or carboxylic acid compound having an imide group are added at once thereto or diluted with a solvent and added dropwise thereto. After completion of the reaction, the resultant may be directly used as the material for forming an organic film, or can also be diluted with an organic solvent and then subjected to liquid separation and washing to remove unreacted raw materials, the catalyst, and so forth present in the system, and to collect the compound for forming an organic film.

The organic solvent used in this event is not particularly limited, as long as it is capable of dissolving the compound and being separated into two layers when mixed with water. Examples of the organic solvent include hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl-tert-butyl ether, and ethylcyclopentylmethyl ether; chlorinated solvents such as methylene chloride, chloroform, dichloroethane, and trichloroethylene; mixtures thereof; etc. As water used for washing in this event, generally, what is called deionized water or ultrapure water may be used. The washing may be performed once or more, preferably approximately once to five times, because washing ten times or more does not always produce the full washing effects thereof.

In the liquid separation and washing, the washing may be performed with a basic aqueous solution to remove unreacted carboxylic acid compound or acidic components in the system. Specific examples of the base include hydroxides of alkaline metals, carbonates of alkaline metals, hydroxides of alkali earth metals, carbonates of alkali earth metals, ammonia, organic ammonium, etc.

Further, in the liquid separation and washing, the washing may be performed with an acidic aqueous solution to remove metal impurities or basic components in the system. Specific examples of the acid include inorganic acids such as hydrochloric acid, hydrobromic acid, sulfuric acid, nitric acid, phosphoric acid, and heteropoly acid; organic acids such as oxalic acid, trifluoroacetic acid, methanesulfonic acid, benzenesulfonic acid, p-toluenesulfonic acid, and trifluoromethanesulfonic acid; etc.

The liquid separation and washing may be performed with any one of the basic aqueous solution and the acidic aqueous solution, or can be performed with a combination of the two. The liquid separation and washing is preferably performed with the basic aqueous solution and the acidic aqueous solution in this order from the viewpoint of removing the metal impurities.

After the liquid separation and washing with the basic aqueous solution and/or acidic aqueous solution, washing with neutral water may be successively performed. As the neutral water, deionized water, ultrapure water, or the like mentioned above may be used. The washing may be performed once or more, but the washing is preferably performed several times to sufficiently remove the basic components and the acidic components. The washing is performed preferably approximately once to five times because washing ten times or more does not always produce the full washing effects.

Further, after the liquid separation and washing, the reaction product can also be collected as a powder by concentrating and drying the solvent or crystallizing the reaction product under reduced pressure or normal pressure. Alternatively, the reaction product can be retained in a solution state with an appropriate concentration to improve the workability in preparing a material for forming an organic film. The concentration at this point is preferably 0.1 to 50 mass %, more preferably 0.5 to 30 mass %. With such a concentration, the viscosity is hardly increased, making it possible to prevent degradation of the workability; in addition, since the amount of the solvent is not excessive, the solution can be prepared economically.

The solvent used in this event is not particularly limited, as long as it is capable of dissolving the compound. Specific examples of the solvent include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. One of these or a mixture of two or more thereof can be used.

Further, in producing the compound used in the inventive material for forming an organic film, another carboxylic acid compound different from the phthalimide compound and carboxylic acid compound having an imide group can also be used in appropriate combination as the compound that reacts with the epoxy compound, depending on the required performances. Specifically, a flexible hydrocarbon structure for improving filling and planarizing properties, a rigid aromatic ring structure for improving etching resistance and heat resistance, a structure having a polar group for improving adhesiveness, and the like can be combined at a certain ratio. These enable the synthesized compound for forming an organic film to achieve all of filling and planarizing properties and heat resistance/etching resistance at high levels.

As the carboxylic acid component used in combination in this event, it is particularly preferable to use a carboxylic acid compound (21) and/or a carboxylic acid compound (22) shown by the following general formulae. It is also possible to combine multiple types of the following carboxylic acid compound (21) and carboxylic acid compound (22) simultaneously. The blending amount of the carboxylic acid compound (21) and the carboxylic acid compound (22) used in combination with the phthalimide compound and carboxylic acid compound having an imide group can be adjusted within a range of 1 to 99 mol %, given that a total amount of all the carboxylic acid and phthalimide compounds is 100 mol %. Although the blending amount varies depending on the required performances, the amount of the carboxylic acid compounds (21) and (22) used in combination is preferably adjusted within a range of 10 to 50 mol % from the viewpoints of imparting etching resistance, heat resistance, and flowability. In the following formulae, n11, n12, n13, Rq, Rs, and Rt are as defined above.

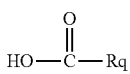

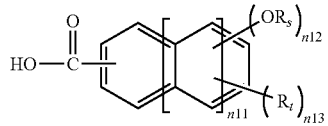

When these carboxylic acids (21), (22) are used, the reaction and collection methods are the same as those for the phthalimide compound and carboxylic acid compound having an imide group, which are the compounds that react with the epoxy compound.

As described above, the inventive compound for forming an organic film enables the resulting organic film to have high filling property, high planarizing property, and excellent adhesiveness to a substrate, as well as favorable heat resistance and dry etching resistance, by the action of the terminal group structure(s) each of which contains an imide group linked with a flexible chain having a hydroxyl group.

[Material for Forming Organic Film]

The present invention further provides a material for forming an organic film, containing: the above-described inventive compound for forming an organic film; and an organic solvent. The material for forming an organic film can also be referred to as a composition for forming an organic film. Note that, in the inventive material for forming an organic film, one kind of the inventive compound for forming an organic film can be used alone, or a combination of two or more kinds thereof can be used.

The inventive material for forming an organic film may be further blended with another polymer. The blendable compound or blendable polymer mixed with the inventive material for forming an organic film serves to improve the film formability by spin coating and the filling property for a stepped substrate. Examples of such a blendable material include novolak resins of phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene) bisphenol, 2,2'difluoro-4,4'-(9H-fluorene-9-ylidene) bisphenol, 2,2'diphenyl-4,4'-(9H-fluorene-9-ylidene) bisphenol, 2,2'dimethoxy-4,4'-(9H-fluorene-9-ylidene) bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, and 7-methoxy-2-naphthol, dihydroxynaphthalenes such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, limonene, etc.; and polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, poly(meth)acrylate, and copolymers thereof. It is also possible to blend a naphthol dicyclopentadiene copolymer disclosed in JP 2004-205685 A, a fluorene bisphenol novolak resin disclosed in JP 2005-128509 A, an acenaphthylene copolymer disclosed in JP 2005-250434 A, fullerene having a phenol group disclosed in JP 2006-227391 A, a bisphenol compound and a novolak resin thereof disclosed in JP 2006-293298 A, a novolak resin of an adamantane phenol compound disclosed in JP 2006-285095 A, a bisnaphthol compound and a novolak resin thereof disclosed in JP 2010-122656 A, a fullerene resin compound disclosed in JP 2008-158002 A, etc. The blendable compound or blendable polymer is blended in an amount of preferably 0 to 1,000 parts by mass, more preferably 0 to 500 parts by mass, based on 100 parts by mass of the inventive compound for forming an organic film.

The organic solvent usable in the inventive material for forming an organic film is not particularly limited, as long as the organic solvent is capable of dissolving the base polymer (compound for forming an organic film), as well as an acid generator, a crosslinking agent, and other additives to be described later. Specifically, a solvent having a boiling point of lower than 180° C. can be used, such as solvents disclosed in paragraphs (0091) to (0092) of JP 2007-199653 A. Above all, it is preferable to use propylene glycol monomethyl ether acetate, propylene glycol monomethyl ether, 2-heptanone, cyclopentanone, cyclohexanone, and a mixture of two or more thereof.

Such a material can be applied by spin coating. Since the inventive compound for forming an organic film as described above is incorporated, the material for forming an organic film has all of favorable dry etching resistance, heat resistance, heat resistance, high filling property, and high planarizing property.

Further, in the inventive material for forming an organic film, it is also possible to add, as a component of the organic solvent, a high-boiling-point solvent having a boiling point of 180° C. or higher to the above-described solvent having a boiling point of lower than 180° C. (a mixture of the solvent having a boiling point of lower than 180° C. and the solvent having a boiling point of 180° C. or higher). The high-boiling-point organic solvent is not particularly limited to hydrocarbons, alcohols, ketones, esters, ethers, chlorinated solvents, and so forth, as long as the high-boiling-point organic solvent is capable of dissolving the compound for forming an organic film. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, methyl benzoate, ethyl benzoate, propyl benzoate, butyl benzoate, dihexyl malonate, diethyl succinate, dipropyl succinate, dibutyl succinate, dihexyl succinate, dimethyl adipate, diethyl adipate, dibutyl adipate, etc. One of these may be used alone, or a mixture thereof may be used.

The boiling point of the high-boiling-point solvent may be appropriately selected according to the temperature at which the material for forming an organic film is heated. The boiling point of the high-boiling-point solvent to be added is preferably 180° C. to 300° C., further preferably 200° C. to 300° C. Such boiling points prevent the evaporation rate at baking (heating) from becoming excessive, which would otherwise occur if the boiling point is too low. Thus, sufficient thermal flowability can be obtained. Meanwhile, the boiling points are not too high, so that the high-boiling-point solvent evaporates after baking and does not remain in the film. Thus, the film properties such as etching resistance are not affected.

The organic solvent is preferably a mixture of one or more organic solvents each having a boiling point of lower than 180° C. and one or more organic solvents each having a boiling point of 180° C. or higher.

When the material for forming an organic film (composition for forming an organic film) contains such organic solvents, the addition of the high-boiling-point solvent(s) to the polymer imparts thermal flowability to the resulting film. Thus, the material for forming an organic film has both higher filling property and higher planarizing property.

When the high-boiling-point solvent(s) are used, the high-boiling-point solvent(s) are blended in an amount of preferably 1 to 30 parts by mass based on 100 parts by mass of the solvent(s) having a boiling point of lower than 180° C. The high-boiling-point solvent(s) in such a formulation amount prevent a failure in providing sufficient thermal flowability during baking, which would otherwise occur if the amount is too small; in addition, degradation of the film properties such as etching resistance is prevented, which would otherwise occur if the amount is so large that the high-boiling-point solvent remains in the film.

In such a material for forming an organic film, thermal flowability is imparted to the compound for forming an organic film by adding the high-boiling-point solvent, so that the material for forming an organic film has both high filling property and high planarizing property.

In the inventive material for forming an organic film, an acid generator can be added so as to further promote the curing reaction. The acid generator includes a material that generates an acid by thermal decomposition, and a material that generates an acid by light irradiation. Any acid generator can be added. Specifically, materials disclosed in paragraphs (0061) to (0085) of JP 2007-199653 A can be added, but the acid generator is not limited thereto.

One kind of the acid generator or a combination of two or more kinds thereof can be used. When the acid generator is added, the amount is preferably 0.05 to 50 parts, more preferably 0.1 to 10 parts, based on 100 parts of the compound for forming an organic film.

To the inventive material for forming an organic film, a surfactant can be added so as to improve the coating property in spin coating. As the surfactant, for example, those disclosed in (0142) to (0147) of JP 2009-269953 A can be used.

Moreover, to the inventive material for forming an organic film, a crosslinking agent can also be added so as to increase the curability and to further suppress intermixing with a film formed thereon. The crosslinking agent is not particularly limited, and known various types of crosslinking agents can be widely used. Examples thereof include methylolated- or methoxymethylated polynuclear phenol-based crosslinking agents, melamine-based crosslinking agents, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, and epoxy-based crosslinking agents.

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the methylolated- or methoxymethylated polynuclear phenol-based crosslinking agents include bisphenols such as bisphenol A and bisphenol F that are subjected to tetramethylolation or tetramethoxymethylation; trisphenols such as triphenolmethane, triphenolethane, 1,1,1-tris(4-hydroxyphenyl)ethane, and tris(4-hydroxyphenyl)-1-ethyl-4-isopropylbenzene that are subjected to hexamethoxymethylation; partial condensates thereof, etc. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidenebis(4-benzyl-2-oxazoline), 2,2'-isopropylidenebis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

Further, to the inventive material for forming an organic film, a plasticizer can be added so as to further improve the planarizing and filling properties. The plasticizer is not particularly limited, and known various types of plasticizers can be widely used. Examples thereof include low-molecular-weight compounds such as phthalic acid esters, adipic acid esters, phosphoric acid esters, trimellitic acid esters, and citric acid esters; and polymers such as polyethers, polyesters, and polyacetal-based polymers disclosed in JP 2013-253227 A.

Further, like the plasticizer, as an additive for imparting the filling and planarizing properties to the inventive material for forming an organic film, it is preferable to use, for example, liquid additives having polyethylene glycol or polypropylene glycol structure, or thermo-decomposable polymers having a weight loss ratio between 30° C. and 250° C. of 40 mass % or more and a weight-average molecular weight of 300 to 200,000. The thermo-decomposable polymers preferably contain a repeating unit having an acetal structure shown by the following general formula (DP1) or (DP1a).

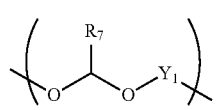

(DP1)

In the formula, $R_7$ represents a hydrogen atom or a saturated or unsaturated monovalent organic group having 1 to 30 carbon atoms which may be substituted. $Y_1$ represents a saturated or unsaturated divalent organic group having 2 to 30 carbon atoms.

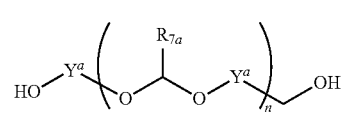

(DP1a)

In the formula, $R_{7a}$ represents an alkyl group having 1 to 4 carbon atoms. V represents a saturated or unsaturated divalent hydrocarbon group having 4 to 10 carbon atoms which may have an ether bond. "n" represents an average repeating unit number of 3 to 500.

Note that one kind of the inventive material for forming an organic film can be used, or two or more kinds thereof can be used in combination. This material for forming an organic film can be used as a resist underlayer film material or a planarizing material for manufacturing a semiconductor device.

Moreover, the inventive material for forming an organic film is quite useful as a resist underlayer film material for multilayer resist processes such as a two-layer resist process, a three-layer resist process using a silicon-containing middle layer film, and a four-layer resist process using a silicon-containing inorganic hard mask middle layer film and organic antireflective coating.

[Substrate for Manufacturing Semiconductor Device]

Additionally, according to the present invention, there can be provided a substrate for manufacturing a semiconductor device, including an organic film on the substrate, the organic film being formed by curing the above-described material for forming an organic film.

The organic film that is cured product of the inventive material for forming an organic film has all of high filling property, high planarizing property, and excellent adhesive force to a substrate. Hence, the organic film does not have fine pores due to insufficient filling or asperity in the organic film surface due to insufficient planarizing property. Moreover, the organic film will not be peeled off when an inorganic hard mask is formed immediately above the organic film. When a substrate for manufacturing a semiconductor device is planarized by such an organic film, the process margin at patterning is increased, and semiconductor devices can be manufactured with high yields.

[Method for Forming Organic Film]

The present invention provides a method for forming an organic film, which serves as a resist underlayer film in a multilayer resist film used in lithography or a planarizing film (organic flat film) for manufacturing a semiconductor, by using the above-described material for forming an organic film.

The inventive method for forming an organic film is, for example, a method for forming an organic film that serves as an organic flat film employed in a semiconductor device manufacturing process, the method including:

spin-coating a substrate to be processed with the inventive material for forming an organic film; and heating the substrate at a temperature of 100° C. or higher and 600° C. or lower for 10 seconds to 600 seconds to form a cured film.

In the inventive method for forming an organic film, a substrate to be processed is coated with the material for forming an organic film by a spin coating method etc. By employing a method like spin coating method, favorable filling property can be obtained. After the spin coating, the solvent is evaporated and baking (heating) is performed to promote the crosslinking reaction, thereby preventing the mixing with a resist upper layer film or a resist middle layer film. The baking is preferably performed at 100° C. or more and 600° C. or less within 10 to 600 seconds, more preferably at 200° C. or more and 500° C. or less within 10 to 300 seconds. In considering such influences as device damage and wafer deformation, the upper limit of the heating temperature in lithographic wafer process is preferably 600° C. or less, more preferably 500° C. or less.

Moreover, in the inventive method for forming an organic film, after a substrate to be processed is coated with the inventive material for forming an organic film by the spin coating method (spin-coating) or the like as described above, an organic film can be formed by curing the organic film material by baking in an atmosphere with an oxygen concentration of 0.1% or more and 21% or less.

A sufficiently cured film can be obtained by baking the inventive material for forming an organic film in such an oxygen atmosphere.

The atmosphere during the baking may be in air. An inert gas such as $N_2$, Ar, or He may be introduced into the atmosphere. The baking temperature and other conditions may be the same as above.

The inventive method for forming an organic film as described above makes it possible to obtain a flat cured film regardless of unevenness of the substrate to be processed, because of the excellent filling and planarizing properties. Accordingly, the method is quite useful in forming a flat cured film on a substrate to be processed which has a structure or step with a height of 30 nm or more.

[Patterning Processes]

The present invention provides a patterning process according to a three-layer resist process using the material for forming an organic film as described above. The patterning process includes:
  forming a resist underlayer film by using the inventive material for forming an organic film on a body to be processed;
  forming a resist middle layer film by using a silicon-containing resist middle layer film material on the resist underlayer film;
  forming a resist upper layer film by using a resist upper layer film material including a photoresist composition on the resist middle layer film;
  forming a circuit pattern in the resist upper layer film;
  etching the resist middle layer film while using the resist upper layer film having the formed pattern as a mask to transfer the pattern to the resist middle layer film;
  etching the resist underlayer film while using the resist middle layer film having the transferred pattern as a mask to transfer the pattern to the resist underlayer film; and
  further etching the body to be processed while using the resist underlayer film having the transferred pattern as a mask to form the pattern in the body to be processed.

This patterning process can be restated as, for example, a method for forming a pattern in a substrate to be processed, and includes at least:
  forming a resist underlayer film by using the inventive material for forming an organic film on a substrate to be processed;
  forming a resist middle layer film (silicon-containing resist middle layer film) by using a resist middle layer film material containing silicon atoms on the resist underlayer film;
  forming a resist upper layer film by using a resist upper layer film material including a photoresist composition on the resist middle layer film, so that a multilayer resist film is formed;
  exposing a pattern circuit region of the resist upper layer film to light, followed by development using a developer to form a resist pattern in the resist upper layer film;
  etching the resist middle layer film while using the obtained resist pattern as an etching mask to form a resist middle layer film pattern;
  etching the resist underlayer film while using the obtained resist middle layer film pattern as an etching mask to form a resist underlayer film pattern; and
  further etching the substrate to be processed while using the obtained resist underlayer film pattern as an etching mask to form such a pattern in the substrate to be processed.

The silicon-containing resist middle layer film in this three-layer resist process exhibits etching resistance to an oxygen gas or a hydrogen gas. Thus, when the resist underlayer film is etched while using the resist middle layer film as a mask in the three-layer resist process, the etching is preferably performed using an etching gas mainly containing an oxygen gas or a hydrogen gas.

As the silicon-containing resist middle layer film in the three-layer resist process, a polysilsesquioxane-based middle layer film is also preferably used. The middle layer film can serve as an organic antireflective coating (BARC). The resist middle layer film having antireflective effect can suppress the reflection. Particularly, for 193-nm light exposure, a material containing many aromatic groups and having high etching resistance relative to the substrate is used as a resist underlayer film, so that the k-value and thus the substrate reflection are increased; in contrast, the substrate reflection can be reduced to 0.5% or less by suppressing the reflection by resist middle layer film. As the resist middle layer film having antireflective effect, a polysilsesquioxane is preferably used which has anthracene for 248-nm and 157-nm light exposure, or a phenyl group or a light-absorbing group having a silicon-silicon bond for 193-nm light exposure in a pendant structure, and which is crosslinked by an acid or heat.

In this case, formation of the silicon-containing resist middle layer film by a spin coating method is more advantageous than by a CVD method in view of convenience and cost.

Alternatively, in a resist process of the present invention, an organic antireflective coating different from a resist middle layer film may be formed on a silicon-containing resist middle layer film to form a four-layered film structure. In other words, the present invention also provides a patterning process including:
  forming a resist underlayer film by using the inventive material for forming an organic film on a body to be processed;
  forming a resist middle layer film by using a resist middle layer film material containing silicon atoms on the resist underlayer film;
  forming an organic antireflective coating on the resist middle layer film;
  forming a resist upper layer film on the organic antireflective coating by using a resist upper layer film material including a photoresist composition, so that a four-layered film structure is constructed;
  forming a circuit pattern in the resist upper layer film;
  etching the organic antireflective coating and the resist middle layer film while using the resist upper layer film having the formed pattern as a mask to transfer the pattern to the organic antireflective coating and the resist middle layer film;

etching the resist underlayer film while using the resist middle layer film having the transferred pattern as a mask to transfer the pattern to the resist underlayer film; and further etching the body to be processed while using the resist underlayer film having the transferred pattern as a mask to form the pattern in the body to be processed.

Moreover, an inorganic hard mask middle layer film may be formed as the middle layer film. In this case, the process can include at least:

forming a resist underlayer film by using the inventive material for forming an organic film on a substrate to be processed;

forming an inorganic hard mask middle layer film selected from a silicon oxide film, a silicon nitride film, and a silicon oxynitride film on the resist underlayer film;

forming a resist upper layer film by using a resist upper layer film material including a photoresist composition on the inorganic hard mask middle layer film;

exposing a pattern circuit region of the resist upper layer film to light, followed by development using a developer to form a resist pattern in the resist upper layer film;

etching the inorganic hard mask middle layer film while using the obtained resist pattern as an etching mask to form an inorganic hard mask middle layer film pattern;

etching the resist underlayer film while using the obtained inorganic hard mask middle layer film pattern as an etching mask to form a resist underlayer film pattern; and further etching the substrate to be processed while using the obtained resist underlayer film pattern as an etching mask to form such a pattern in the substrate to be processed. In other words, the present invention also provides a patterning process including:

forming a resist underlayer film by using the inventive material for forming an organic film on a body to be processed;

forming an inorganic hard mask middle layer film selected from a silicon oxide film, a silicon nitride film, and a silicon oxynitride film on the resist underlayer film;

forming a resist upper layer film by using a resist upper layer film material including a photoresist composition on the inorganic hard mask middle layer film;

forming a circuit pattern in the resist upper layer film;

etching the inorganic hard mask middle layer film while using the resist upper layer film having the formed pattern as a mask to transfer the pattern to the inorganic hard mask middle layer film;

etching the resist underlayer film while using the inorganic hard mask middle layer film having the formed pattern as a mask to transfer the pattern to the resist underlayer film; and further etching the body to be processed while using the resist underlayer film having the formed pattern as a mask to form the pattern in the body to be processed.

In the case where an inorganic hard mask middle layer film is formed on a resist underlayer film as described above, a silicon oxide film, a silicon nitride film, and a silicon oxynitride film (SiON film) can be formed by a CVD method, an ALD method, or the like. For example, the method for forming a silicon nitride film is disclosed in JP 2002-334869 A and WO 2004/066377 A1. The film thickness of the inorganic hard mask middle layer film is preferably 5 to 200 nm, more preferably 10 to 100 nm. As the inorganic hard mask middle layer film, a SiON film is most preferably used which is effective as an antireflective film. When the SiON film is formed, the substrate temperature reaches 300 to 500° C. Hence, the underlayer film needs to withstand the temperature of 300 to 500° C. Since the material for forming an organic film used in the present invention has high heat resistance and can withstand high temperatures of 300° C. to 500° C., this enables the combination of the inorganic hard mask middle layer film formed by a CVD method or an ALD method with the resist underlayer film formed by a spin coating method.

Moreover, the present invention is also suitable for a four-layer resist process using an organic antireflective coating. In this case, the process can include at least:

forming a resist underlayer film by using the inventive organic film material on substrate to be processed;

forming an inorganic hard mask middle layer film selected from a silicon oxide film, a silicon nitride film, and a silicon oxynitride film on the resist underlayer film;

forming an organic antireflective coating on the inorganic hard mask middle layer film;

forming a resist upper layer film by using a resist upper layer film material of photoresist composition on the organic antireflective coating, so that a multilayer resist film is formed;

exposing a pattern circuit region of the resist upper layer film to light, followed by development using a developer to form a resist pattern in the resist upper layer film;

etching the organic antireflective coating and the inorganic hard mask middle layer film while using the obtained resist pattern as an etching mask to form an inorganic hard mask middle layer film pattern;

etching the resist underlayer film while using the obtained inorganic hard mask middle layer film pattern as an etching mask to form a resist underlayer film pattern; and further etching the substrate to be processed while using the obtained resist underlayer film pattern as an etching mask to form such a pattern in the substrate to be processed. In other words, the present invention provides a patterning process including:

forming a resist underlayer film by using the inventive material for forming an organic film on a body to be processed;

forming an inorganic hard mask middle layer film selected from a silicon oxide film, a silicon nitride film, and a silicon oxynitride film on the resist underlayer film;

forming an organic antireflective coating on the inorganic hard mask middle layer film;

forming a resist upper layer film on the organic antireflective coating by using a resist upper layer film material including a photoresist composition, so that a four-layered film structure is constructed;

forming a circuit pattern in the resist upper layer film;

etching the organic antireflective coating and the inorganic hard mask middle layer film while using the resist upper layer film having the formed pattern as a mask to transfer the pattern to the organic antireflective coating and the inorganic hard mask middle layer film;

etching the resist underlayer film while using the inorganic hard mask middle layer film having the formed pattern as a mask to transfer the pattern to the resist underlayer film; and further etching the body to be processed while using the resist underlayer film having the formed pattern as a mask to form the pattern in the body to be processed.

Although a photoresist film may be formed as a resist upper layer film on an inorganic hard mask middle layer film, it is also possible to form an organic antireflective coating (BARC) on the inorganic hard mask middle layer film by spin coating and then form the photoresist film on the BARC as described above. Particularly, when a SiON film is used as the inorganic hard mask middle layer film, two antireflective films including the SiON film and the BARC make it possible to suppress the reflection even in liquid immersion exposure at a high NA exceeding 1.0. Another merit of the BARC formation is having an effect of reducing footing of the photoresist pattern immediately above the SiON film.

The resist upper layer film in the three-layer and four-layer resist processes may be a positive type or a negative type, and any generally-used photoresist composition can be employed. After spin coating of the photoresist composition, pre-baking is preferably performed within ranges of 60 to 180° C. and 10 to 300 seconds. Then, light exposure, post-exposure bake (PEB), and development are performed according to conventional methods to obtain a resist pattern. Note that the thickness of the resist upper layer film is not particularly limited, but is preferably 30 to 500 nm, particularly preferably 50 to 400 nm.

In the resist upper layer film, a circuit pattern (resist upper layer film pattern) is formed. The circuit pattern is preferably formed by a lithography using light with a wavelength of 10 nm or more and 300 nm or less, direct lithography with electron beam, nanoimprinting, or a combination thereof.

Note that the exposure light includes high energy beam with a wavelength of 300 nm or less; specifically, deep ultraviolet ray, KrF excimer laser beam (248 nm), ArF excimer laser beam (193 nm), $F_2$ laser beam (157 nm), $Kr_2$ laser beam (146 nm), $Ar_2$ laser beam (126 nm), soft X-ray (EUV) of 3 to 20 nm, electron beam (EB), ion beam, X-ray, etc.

Additionally, in forming the circuit pattern, the circuit pattern is preferably developed with an alkali or organic solvent.

Next, using the resulting resist pattern as a mask, etching is performed. In the three-layer and four-layer resist processes, the resist middle layer film, the inorganic hard mask middle layer film, and the organic antireflective coating are etched while using a fluorocarbon-based gas and the resist pattern as the mask. Thereby, a resist middle layer film pattern, an inorganic hard mask middle layer film pattern, and an organic antireflective coating pattern are formed Next, by using the obtained resist middle layer film pattern, inorganic hard mask middle layer film pattern, or organic antireflective coating pattern as a mask, the resist underlayer film is processed by etching.

The subsequent etching of the substrate to be processed can be performed according to a conventional method. For example, the substrate to be processed made of $SiO_2$, SiN, or silica-based low-dielectric insulating film is etched mainly with a fluorocarbon-based gas; and p-Si, Al, or W is etched mainly with a chlorine- or bromine-based gas. When the substrate is processed by etching with a fluorocarbon-based gas, the silicon-containing middle layer film pattern in the three-layer and four-layer resist processes is removed when the substrate is processed. Meanwhile, when the substrate is processed by etching with a chlorine- or bromine-based gas, the silicon-containing middle layer film pattern needs to be removed by additional dry etching with a fluorocarbon-based gas after the substrate processing.

The resist underlayer film obtained from the inventive organic film material is characterized by excellent etching resistance when the substrate to be processed is etched as described above.

Note that the substrate to be processed is not particularly limited, and examples thereof include substrates made of Si, α-Si, p-Si, $SiO_2$, SiN, SiON, W, TiN, Al, or the like; these substrates coated with a layer to be processed; etc. Examples of the layer to be processed include various Low-k films made of Si, $SiO_2$, SiON, SiN, p-Si, α-Si, W, W—Si, Al, Cu, Al—Si, or the like; and stopper films thereof. The layer can be formed to have a thickness of generally 50 to 10,000 nm, particularly 100 to 5,000 nm. Note that when the layer to be processed is formed, the substrate and the layer to be processed are formed from different materials.

In the inventive patterning processes, as the body to be processed, it is preferable to use a semiconductor device substrate or, for example, the semiconductor device substrate coated with any of a metal film, a metal carbide film, a metal oxide film, a metal nitride film, a metal oxycarbide film, and a metal oxynitride film. In other words, the body to be processed is preferably a semiconductor device substrate, a metal film, a metal carbide film, a metal oxide film, a metal nitride film, a metal oxycarbide film, or a metal oxynitride film.

Further, as the body to be processed, it is preferable to use a body to be processed which contain silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

Hereinbelow, an example of the three-layer resist process will be specifically described with reference to FIG. 1.

As shown in FIG. 1(A), in the three-layer resist process, a resist underlayer film 3 is formed by using the inventive organic film material on a layer 2 to be processed which has been stacked on a substrate 1. Then, a resist middle layer film 4 is formed, and a resist upper layer film 5 is formed thereon.

Next, as shown in FIG. 1(B), a predetermined portion 6 of the resist upper layer film is exposed to light, followed by PEB and development to form a resist pattern 5a (FIG. 1(C)). Using the resulting resist pattern 5a as a mask, the resist middle layer film 4 is etched with a CF-based gas. Thereby, a resist middle layer film pattern 4a is formed (FIG. 1(D)). After the resist pattern 5a is removed, the resist underlayer film 3 is etched with oxygen plasma while using the resulting resist middle layer film pattern 4a as a mask. Thereby, a resist underlayer film pattern 3a is formed (FIG. 1(E)). Further, after the resist middle layer film pattern 4a is removed, the layer 2 to be processed is etched while using the resist underlayer film pattern 3a as a mask. Thus, a pattern 2a is formed (FIG. 1(F)).

When an inorganic hard mask middle layer film is used, the inorganic hard mask middle layer film is formed in place of the resist middle layer film 4. When an organic antireflective coating (BARC) is formed, the BARC layer is provided between the resist middle layer film 4 and the resist upper layer film 5. The etching of the BARC may be performed before the etching of the resist middle layer film 4, but these etchings may be performed continuously. Alternatively, after the BARC is etched alone, for example, the etching apparatus is changed, and then the etching of the resist middle layer film 4 may be performed.

As described above, according to the inventive patterning processes, a fine pattern can be precisely formed in a substrate to be processed in the multilayer resist processes.

EXAMPLE

Hereinafter, the present invention will be further specifically described by referring to Synthesis Examples, Comparative Synthesis Examples, Examples, and Comparative Examples. However, the present invention is not limited thereto. Note that, regarding molecular weight and dispersity, gel permeation chromatography (GPC) was performed using tetrahydrofuran as an eluent to determine weight-average molecular weight (Mw) and number-average molecular weight (Mn) in terms of polystyrene, and dispersity (Mw/Mn) was obtained therefrom.

Synthesis Examples: Synthesis of Compounds Used in Organic Film Materials

Polymers (A1) to (A29) used in organic film materials were synthesized using epoxy compounds (Compounds B: (B1) to (B14)) and phthalimide or carboxylic acid compounds (Compounds C: (C1) to (C9)) shown below.

Compounds B:

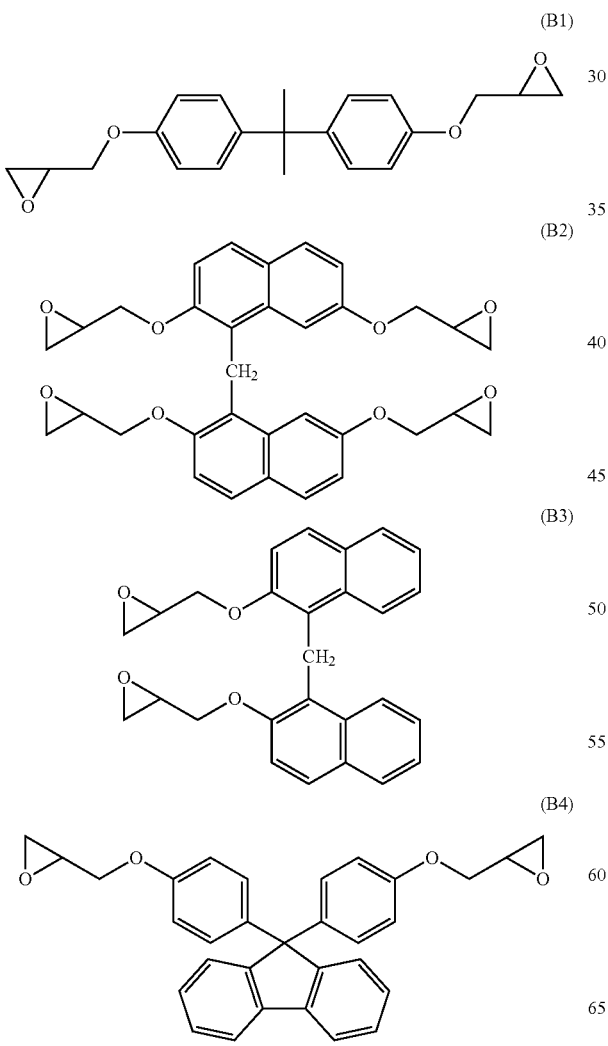

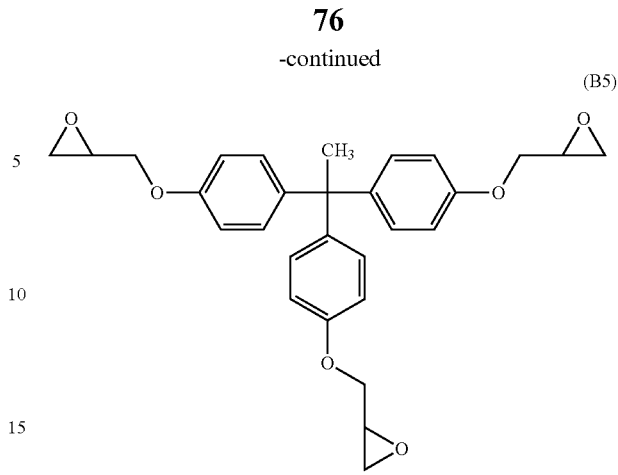

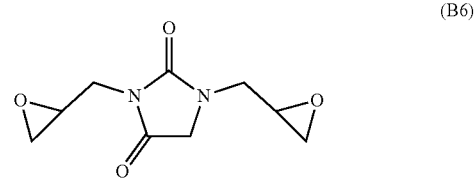

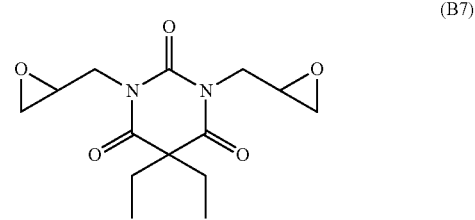

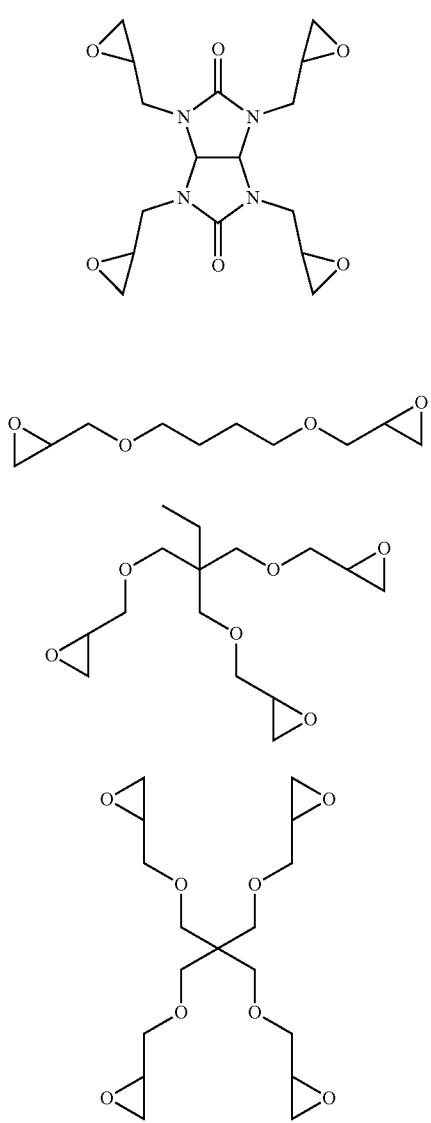

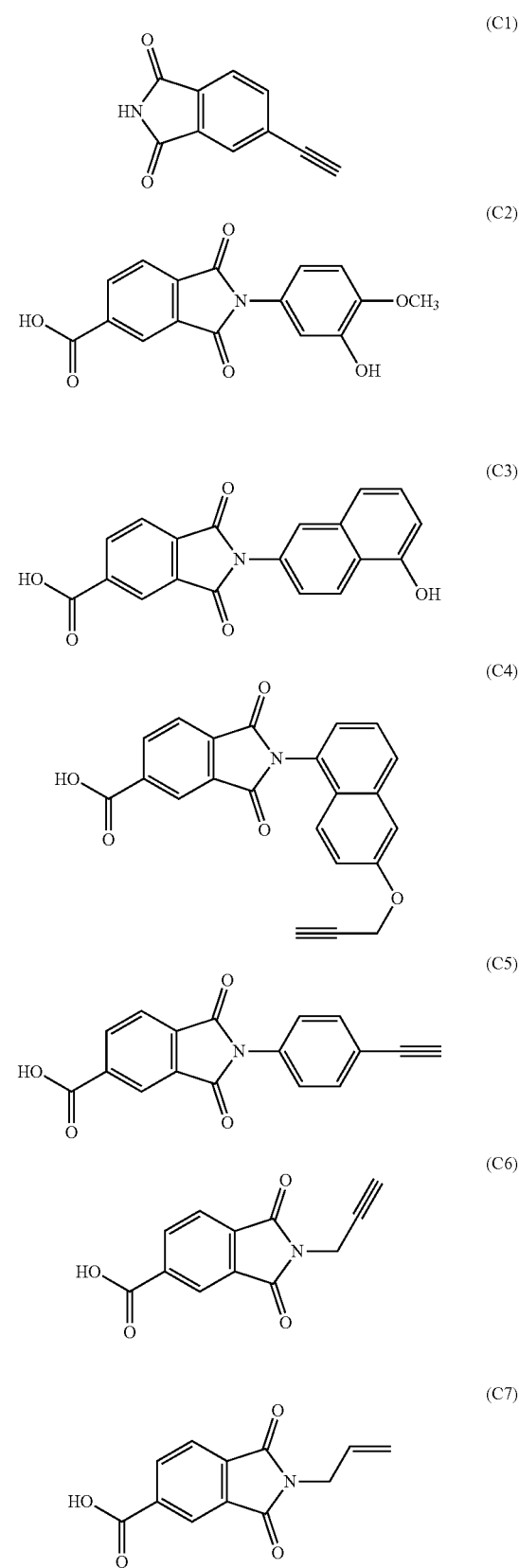

As the reagents other than the followings, commercially-available reagents were used.

(B1) EXA-850CRP (manufactured by DIC Corporation), epoxy equivalent: 172
(B2) HP-4700 (manufactured by DIC Corporation), epoxy equivalent: 165
(B3) HP-4770 (manufactured by DIC Corporation), epoxy equivalent: 205
(B5) 1032H60 (manufactured by Mitsubishi Chemical Corporation), epoxy equivalent: 167
(B10) DAG-G (manufactured by Shikoku Chemicals Corporation), epoxy equivalent: 168
(B11) TG-G (manufactured by Shikoku Chemicals Corporation), epoxy equivalent: 92
(B13) Epolight MF (manufactured by Kyoei Kagaku Kogyo Co., Ltd.), epoxy equivalent: 140
(B14) PETG (manufactured by Showa Denko K.K.), epoxy equivalent: 90

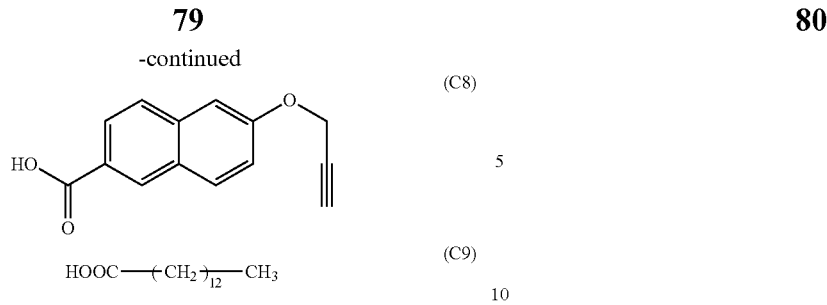

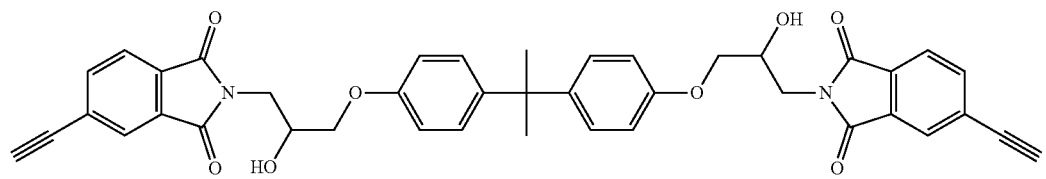 [SMILES: C#Cc1ccc2c(c1)C(=O)N(CC(O)COc1ccc(C(C)(C)c3ccc(OCC(O)CN4C(=O)c5ccc(C#C)cc5C4=O)cc3)cc1)C2=O]

[Synthesis Example 1] Synthesis of Compound (A1)

Under a nitrogen atmosphere, a homogeneous solution with an inner temperature of 100° C. was prepared from 20.0 g of Epoxy Compound (B1), 19.9 g of Phthalimide Compound (C1), and 200 g of 2-methoxy-1-propanol. Then, 1.00 g of benzyltriethylammonium chloride was added thereto and stirred for 12 hours with the inner temperature of 120° C. After cooling to room temperature, 300 ml of methyl isobutyl ketone was added, and washing was performed twice with 100 g of a 2% NaHCO$_3$ aqueous solution and 100 g of a 3% nitric acid aqueous solution, and five times with 100 g of ultrapure water. The organic layer was evaporated under reduced pressure to dryness. Thus, Compound (A1) was obtained. The weight-average molecular weight (Mw) and dispersity (Mw/Mn) thereof was determined by GPC. The results were Mw=780 and Mw/Mn=1.02.

[Synthesis Examples 2 to 29] Synthesis of Compounds (A2) to (A29)

Compounds (A2) to (A29) as shown in Tables 2-1 to 2-6 were obtained as products under the same reaction conditions as those in Synthesis Example 1, except that the epoxy compounds and phthalimide compound or carboxylic acid compounds shown in Table 1 were used. The weight-average molecular weight (Mw) and dispersity (Mw/Mn) of the resulting compounds were obtained and shown in Tables 2-1 to 2-6.

TABLE 1

| Synthesis Example | Compounds B | Compounds C | Product |
|---|---|---|---|
| 1 | [B1]: 20.0 g | [C1]: 19.9 g | A-1 |
| 2 | [B1]: 15.0 g | [C7]: 20.2 g | A-2 |
| 3 | [B2]: 20.0 g | [C1]: 20.8 g | A-3 |
| 4 | [B2]: 15.0 g | [C6]: 20.8 g | A-4 |
| 5 | [B3]: 15.0 g | [C2]: 22.9 g | A-5 |
| 6 | [B3]: 15.0 g | [C5]: 21.3 g | A-6 |
| 7 | [B4]: 15.0 g | [C3]: 21.3 g | A-7 |
| 8 | [B4]: 15.0 g | [C4]: 21.6 g | A-8 |
| 9 | [B5]: 20.0 g | [C1]: 20.5 g | A-9 |
| 10 | [B5]: 15.0 g | [C7]: 20.8 g | A-10 |
| 11 | [B6]: 10.0 g | [C6]: 21.6 g | A-11 |
| 12 | [B7]: 10.0 g | [C4]: 25.1 g | A-12 |
| 13 | [B8]: 15.0 g | [C1]: 18.3 g | A-13 |
| 14 | [B8]: 10.0 g | [C5]: 20.7 g | A-14 |
| 15 | [B9]: 15.0 g | [C1]: 25.9 g | A-15 |
| 16 | [B9]: 10.0 g | [C7]: 23.3 g | A-16 |
| 17 | [B10]: 10.0 g | [C4]: 22.1 g | A-17 |
| 18 | [B10]: 15.0 g | [C5]: 26.0 g | A-18 |
| 19 | [B11]: 15.0 g | [C1]: 27.9 g | A-19 |
| 20 | [B11]: 10.0 g | [C2]: 34.1 g | A-20 |
| 21 | [B12]: 8.0 g | [C3]: 26.4 g | A-21 |
| 22 | [B12]: 8.0 g | [C4]: 29.4 g | A-22 |
| 23 | [B13]: 15.0 g | [C6]: 24.6 g | A-23 |
| 24 | [B13]: 15.0 g | [C7]: 24.8 g | A-24 |
| 25 | [B14]: 15.0 g | [C1]: 28.5 g | A-25 |
| 26 | [B14]: 10.0 g | [C5]: 32.4 g | A-26 |
| 27 | [B2]: 15.0 g | [C5]: 19.9 g [C8]: 5.1 g | A-27 |
| 28 | [B9]: 15.0 g | [C1]: 20.7 g [C9]: 6.9 g | A-28 |
| 29 | [B14]: 10.0 g | [C1]: 14.3 g [C2]: 8.7 g | A-29 |

TABLE 2-1

| Synthesis Example | Product | Mw | Mw/Mn |
|---|---|---|---|
| 1 | (A1) | 780 | 1.02 |
| 2 | (A2) | 890 | 1.04 |
| 3 | (A3) | 1800 | 1.31 |
| 4 | (A4) | 2170 | 1.34 |
| 5 | (A5) | 1300 | 1.27 |

TABLE 2-2

| Synthesis Example | Product | Mw | Mw/Mn |
|---|---|---|---|
| 6 | (A6) | 1250 | 1.25 |
| 7 | (A7) | 1240 | 1.03 |
| 8 | (A8) | 1330 | 1.04 |
| 9 | (A9) | 1430 | 1.33 |
| 10 | (A10) | 1710 | 1.36 |

TABLE 2-3
| Synthesis Example | Product | Mw | Mw/Mn |
|---|---|---|---|
| 11 | 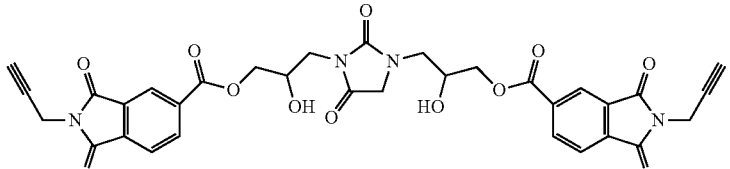<br>(A11) | 740 | 1.04 |
| 12 | 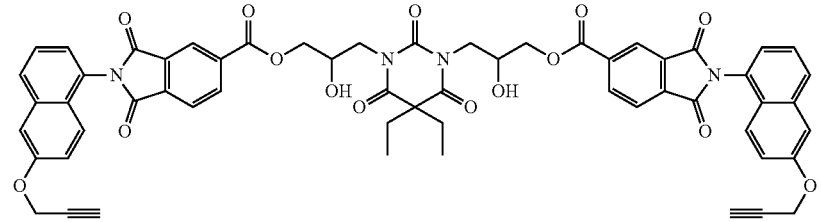 [SMILES: C#CCOc1ccc2c(N3C(=O)c4ccc(C(=O)OCC(O)CN5C(=O)N(CC(O)COC(=O)c6ccc7c(c6)C(=O)N(c6cccc8cc(OCC#C)ccc68)C7=O)C(=O)C(CC)(CC)C5=O)cc4C3=O)cccc2c1]<br>(A12) | 1150 | 1.05 |
| 13 | 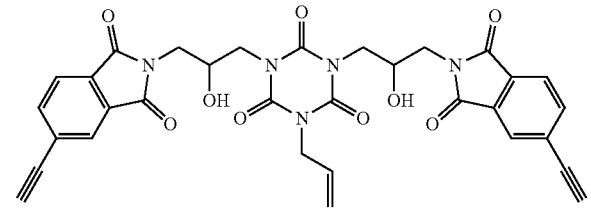 [SMILES: C#Cc1ccc2c(c1)C(=O)N(CC(O)Cn1c(=O)n(CC=C)c(=O)n(CC(O)CN3C(=O)c4ccc(C#C)cc4C3=O)c1=O)C2=O]<br>(A13) | 720 | 1.03 |
| 14 | 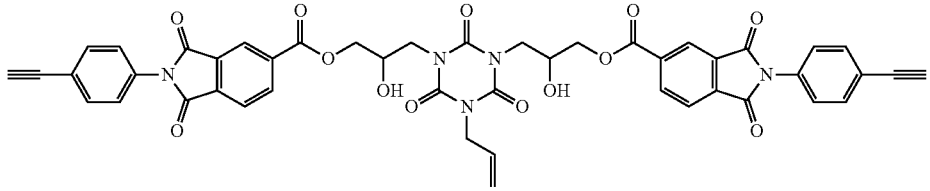 [SMILES: C#Cc1ccc(N2C(=O)c3ccc(C(=O)OCC(O)Cn4c(=O)n(CC=C)c(=O)n(CC(O)COC(=O)c5ccc6c(c5)C(=O)N(c5ccc(C#C)cc5)C6=O)c4=O)cc3C2=O)cc1]<br>(A14) | 970 | 1.02 |
| 15 | 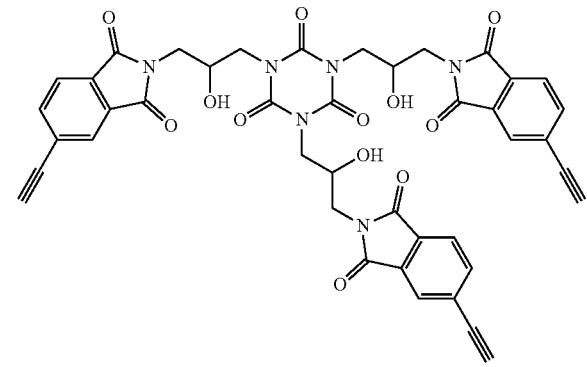 [SMILES: C#Cc1ccc2c(c1)C(=O)N(CC(O)Cn1c(=O)n(CC(O)CN3C(=O)c4ccc(C#C)cc4C3=O)c(=O)n(CC(O)CN3C(=O)c4ccc(C#C)cc4C3=O)c1=O)C2=O]<br>(A15) | 900 | 1.02 |

TABLE 2-4

| Synthesis Example | Product | Mw | Mw/Mn |
|---|---|---|---|
| 16 | (A16) | 1090 | 1.03 |
| 17 | (A17) | 1290 | 1.05 |
| 18 | (A18) | 1100 | 1.06 |
| 19 | (A19) | 1260 | 1.05 |

TABLE 2-4-continued
| Synthesis Example | Product | Mw | Mw/Mn |
|---|---|---|---|
| 20 | 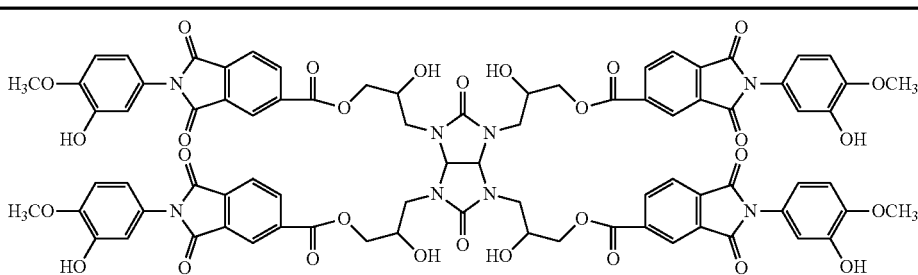 (A20) | 1860 | 1.06 |
TABLE 2-5
| Synthesis Example | Product | Mw | Mw/Mn |
|---|---|---|---|
| 21 | (A21) | 920 | 1.02 |
| 22 | (A22) | 990 | 1.03 |
| 23 | (A23) | 1150 | 1.25 |
| 24 | (A24) | 1120 | 1.21 |

TABLE 2-5-continued
| Synthesis Example | Product | Mw | Mw/Mn |
|---|---|---|---|
| 25 | (A25) | 1200 | 1.08 |
TABLE 2-6
| Synthesis Example | Product | Mw | Mw/Mn |
|---|---|---|---|
| 26 | (A26) | 1680 | 1.07 |
| 27 | (A27) | 2320 | 1.35 |
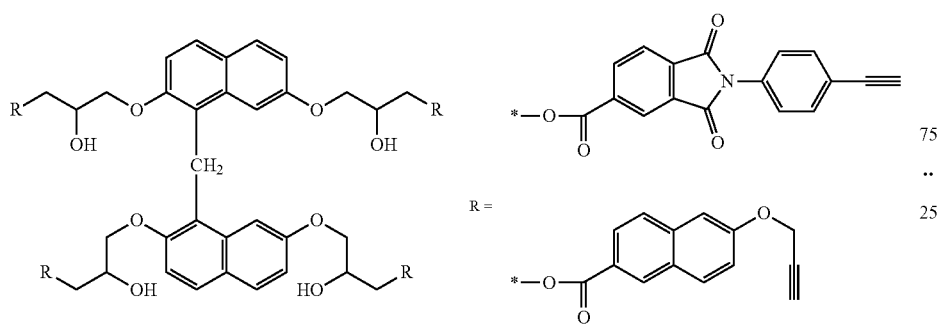

TABLE 2-6-continued

| Synthesis Example | Product | Mw | Mw/Mn |
|---|---|---|---|
| 28 | 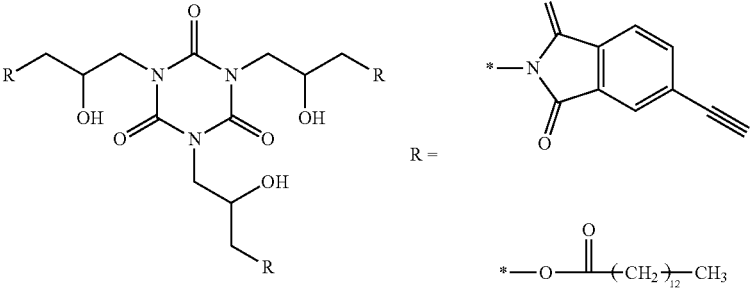 (A28) | 950 | 1.08 |
| 29 | 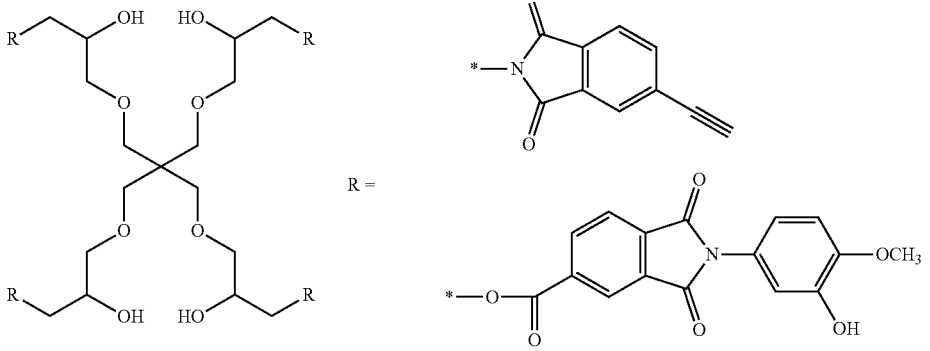 (A29) | 1840 | 1.09 |

[Comparative Synthesis Example 1] Synthesis of Compound (R1)

Under a nitrogen atmosphere, a homogeneous solution with an inner temperature of 100° C. was prepared from 20.0 g of Epoxy Compound (B2), 17.7 g of 4-ethynylbenzoate, and 200 g of 2-methoxy-1-propanol. Then, 1.00 g of benzyltriethylammonium chloride was added thereto and stirred for 12 hours with the inner temperature of 120° C. After cooling to room temperature, 300 ml of methyl isobutyl ketone was added, and washing was performed twice with 100 g of a 2% NaHCO₃ aqueous solution and 100 g of a 3% nitric acid aqueous solution, and five times with 100 g of ultrapure water. The organic layer was evaporated under reduced pressure to dryness. Thus, Compound (R1) was obtained. The weight-average molecular weight (Mw) and dispersity (Mw/Mn) thereof was determined by GPC. The results were Mw=1740 and Mw/Mn=1.33.

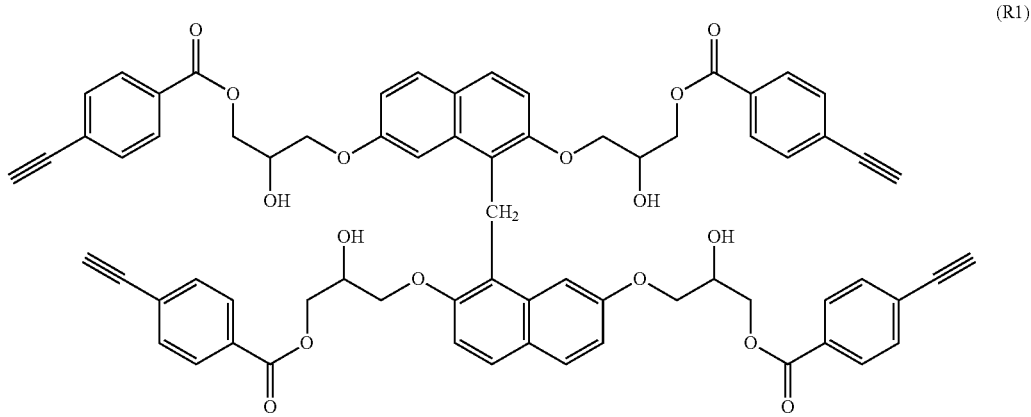 [SMILES: C#Cc1ccc(C(=O)OCC(O)COc2ccc3ccc(OCC(O)COC(=O)c4ccc(C#C)cc4)c(Cc4c(OCC(O)COC(=O)c5ccc(C#C)cc5)ccc5ccc(OCC(O)COC(=O)c6ccc(C#C)cc6)cc45)c3c2)cc1]

(R1)

[Comparative Synthesis Example 2] Synthesis of Compound (R2)

Under a nitrogen atmosphere, a homogeneous solution with an inner temperature of 100° C. was prepared from 20.0 g of Epoxy Compound (B2), 23.3 g of butoxybenzoate, and 200 g of 2-methoxy-1-propanol. Then, 1.00 g of benzyltriethylammonium chloride was added thereto and stirred for 12 hours with the inner temperature of 120° C. After cooling to room temperature, 300 ml of methyl isobutyl ketone was added, and washing was performed twice with 100 g of a 2% NaHCO$_3$ aqueous solution and 100 g of a 3% nitric acid aqueous solution, and five times with 100 g of ultrapure water. The organic layer was evaporated under reduced pressure to dryness. Thus, Compound (R2) was obtained. The weight-average molecular weight (Mw) and dispersity (Mw/Mn) thereof was determined by GPC. The results were Mw=1930 and Mw/Mn=1.32.

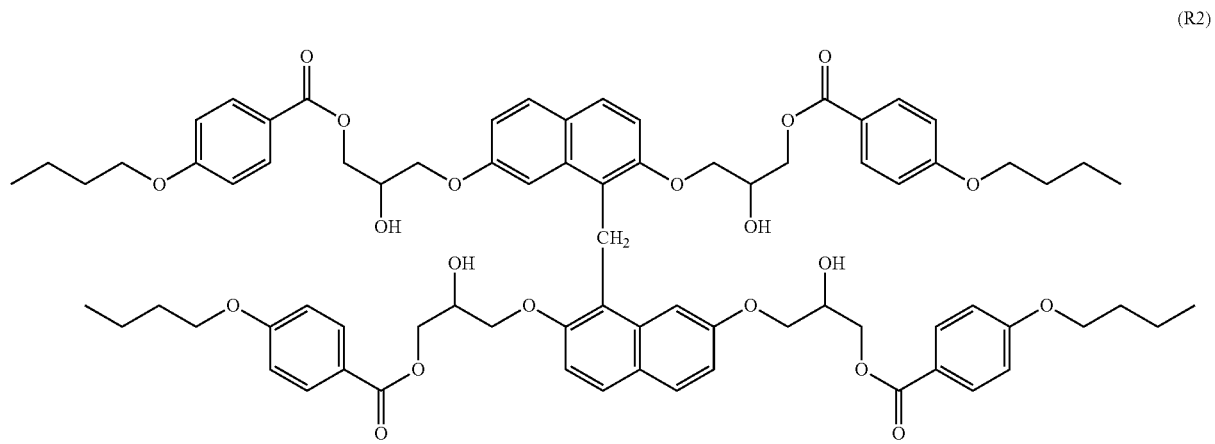 [SMILES: CCCCOc1ccc(C(=O)OCC(O)COc2ccc3ccc(OCC(O)COC(=O)c4ccc(OCCCC)cc4)c(Cc4c(OCC(O)COC(=O)c5ccc(OCCCC)cc5)ccc5ccc(OCC(O)COC(=O)c6ccc(OCCCC)cc6)cc45)c3c2)cc1]

(R2)

[Comparative Synthesis Example 3] Synthesis of Compound (R3)

Under a nitrogen atmosphere, a homogeneous solution with an inner temperature of 100° C. was prepared from 20.0 g of Epoxy Compound (B2), 16.7 g of 4-hydroxybenzoate, and 200 g of 2-methoxy-1-propanol. Then, 1.00 g of benzyltriethylammonium chloride was added thereto and stirred for 12 hours with the inner temperature of 120° C. After cooling to room temperature, 300 ml of methyl isobutyl ketone was added, and washing was performed twice with 100 g of a 2% NaHCO$_3$ aqueous solution and 100 g of a 3% nitric acid aqueous solution, and five times with 100 g of ultrapure water. The organic layer was evaporated under reduced pressure to dryness. Thus, Compound (R3) was obtained. The weight-average molecular weight (Mw) and dispersity (Mw/Mn) thereof was determined by GPC. The results were Mw=1610 and Mw/Mn=1.35.

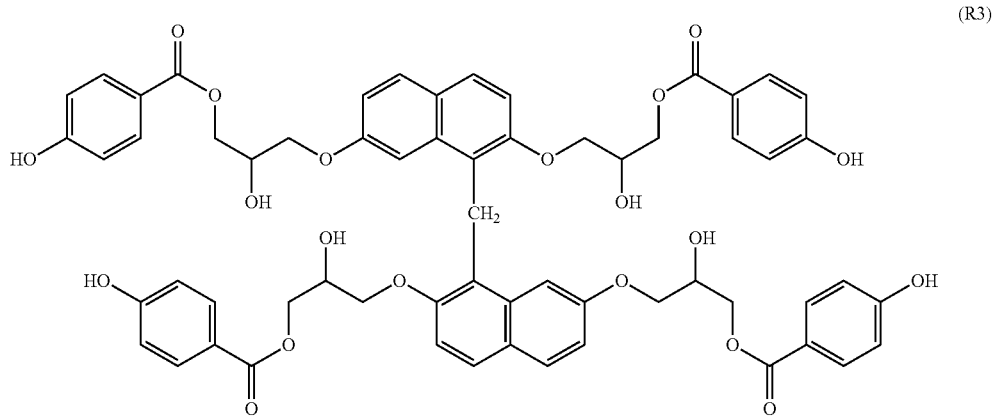 [SMILES: O=C(OCC(O)COc1ccc2ccc(OCC(O)COC(=O)c3ccc(O)cc3)c(Cc3c(OCC(O)COC(=O)c4ccc(O)cc4)ccc4ccc(OCC(O)COC(=O)c5ccc(O)cc5)cc34)c2c1)c1ccc(O)cc1]

(R3)

[Comparative Synthesis Example 4] Synthesis of Compound (R4)

Under a nitrogen atmosphere, a homogeneous solution with an inner temperature of 40° C. was prepared by adding 100 g of N-methyl-2-pyrrolidone to 26.02 g of 4,4'-(4,4'-isopropylidenediphenoxy)diphthalic anhydride. Then, 11.72 g of m-ethynylaniline having been dissolved in advance in 30 g of N-methyl-2-pyrrolidone was slowly added dropwise for the reaction with the inner temperature of 40° C. for 3 hours. Thereby, an amic acid solution was obtained. To the obtained amic acid solution, 3.96 g of pyridine was added, and further 12.25 g of acetic anhydride was slowly added dropwise. Then, the reaction was allowed to proceed at an inner temperature of 60° C. for 4 hours for imidization. After completion of the reaction, the resultant was cooled to room temperature, 300 g of methyl isobutyl ketone was added, and the organic layer was washed with 100 g of a 3% nitric acid aqueous solution. Subsequently, the organic layer was further washed six times with 100 g of pure water, and dried under reduced pressure. To the residue, 100 g of THF (tetrahydrofuran) was added, and a homogeneous solution was prepared. Thereafter, a crystal was precipitated with 500 g of methanol. The precipitated crystal was separated by filtration, washed twice with 300 g of methanol, and collected. The collected crystal was vacuum dried at 70° C. Thus, (R4) was obtained.

The weight-average molecular weight (Mw) and dispersity (Mw/Mn) thereof was determined by GPC. The results were Mw=850 and Mw/Mn=1.01.

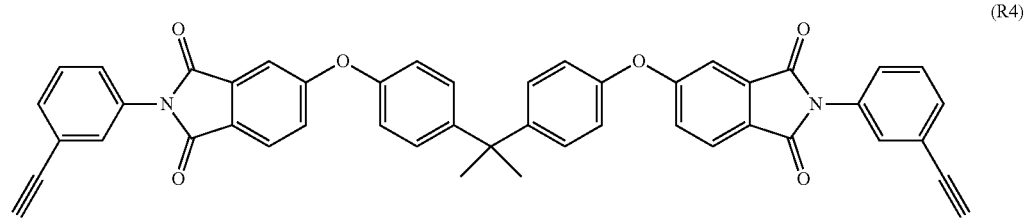 [SMILES: C#Cc1cccc(N2C(=O)c3ccc(Oc4ccc(C(C)(C)c5ccc(Oc6ccc7c(c6)C(=O)N(c6cccc(C#C)c6)C7=O)cc5)cc4)cc3C2=O)c1]

(R4)

Preparation of Materials (UDL-1 to -32, Comparative Example UDL-1 to -4) for Forming Organic Film Compounds (A-1) to (A-29) and Comparative Compounds (R-1) to (R-4) described above were dissolved in proportions shown in Table 3-1 and Table 3-2 using at least one of propylene glycol monomethyl ether acetate (PGMEA) and 2-methoxy-1-propanol (PGME) both of which contained 0.1 mass % PF636 (manufactured by OMNOVA Solutions Inc.), and optionally using (S1) 1,6-diacetoxyhexane (boiling point: 260° C.) or (S2) tripropylene glycol monomethyl ether (boiling point: 242° C.) as a high-boiling-point solvent, a crosslinking agent XL1 or XL2, and a thermal acid generator AG1. The solutions were filtered through a 0.1-μm filter made of a fluorinated resin to prepare materials (UDL-1 to -32, Comparative Example UDL-1 to -4) for forming an organic film.

TABLE 3-1

| Material for forming organic film | Polymer or Compound (parts by mass) | Cross-linking agent (parts by mass) | Acid generator (parts by mass) | High-boiling-point solvent (parts by mass) | PGME (parts by mass) | PGMEA (parts by mass) |
|---|---|---|---|---|---|---|
| UDL-1 | A1 (10) | — | — | — | 90 | — |
| UDL-2 | A2 (10) | — | — | — | 90 | — |
| UDL-3 | A3 (10) | — | — | — | 90 | — |
| UDL-4 | A4 (10) | — | — | — | 90 | — |
| UDL-5 | A5 (10) | XL1 (2) | — | — | 90 | — |
| UDL-6 | A6 (10) | — | — | — | 90 | — |
| UDL-7 | A7 (10) | XL1 (2) | — | — | — | 90 |
| UDL-8 | A8 (10) | — | — | — | — | 90 |
| UDL-9 | A9 (10) | — | — | — | 90 | — |
| UDL-10 | A10 (10) | — | — | — | 90 | — |
| UDL-11 | A11 (10) | — | — | — | 90 | — |
| UDL-12 | A12 (10) | — | — | — | 90 | — |
| UDL-13 | A13 (10) | — | — | — | 90 | — |
| UDL-14 | A14 (10) | — | — | — | 90 | — |
| UDL-15 | A15 (10) | — | — | — | 90 | — |
| UDL-16 | A16 (10) | — | — | — | 90 | — |
| UDL-17 | A17 (10) | — | — | — | 90 | — |
| UDL-18 | A18 (10) | — | — | — | 90 | — |
| UDL-19 | A19 (10) | — | — | — | 90 | — |
| UDL-20 | A20 (10) | XL1 (2) | — | — | 90 | — |

TABLE 3-2

| Material for forming organic film | Polymer or Compound (parts by mass) | Cross-linking agent (parts by mass) | Acid generator (parts by mass) | High-boiling-point solvent (parts by mass) | PGME (parts by mass) | PGMEA (parts by mass) |
|---|---|---|---|---|---|---|
| UDL-21 | A21 (10) | XL1 (2) | — | — | — | 90 |
| UDL-22 | A22 (10) | — | — | — | — | 90 |
| UDL-23 | A23 (10) | — | — | — | — | 90 |
| UDL-24 | A24 (10) | — | — | — | — | 90 |
| UDL-25 | A25 (10) | — | — | — | 90 | — |
| UDL-26 | A26 (10) | — | — | — | 90 | — |
| UDL-27 | A27 (10) | — | — | — | 90 | — |
| UDL-28 | A28 (10) | — | — | — | 90 | — |
| UDL-29 | A29 (10) | — | — | — | 90 | — |
| UDL-30 | A3 (5) A21 (5) | — | — | — | 90 | — |
| UDL-31 | A3 (10) | — | — | S1 (10) | 80 | — |
| UDL-32 | A3 (10) | — | — | S2 (10) | 80 | — |

TABLE 3-2-continued

| Material for forming organic film | Polymer or Compound (parts by mass) | Cross-linking agent (parts by mass) | Acid generator (parts by mass) | High-boiling-point solvent (parts by mass) | PGME (parts by mass) | PGMEA (parts by mass) |
|---|---|---|---|---|---|---|
| Comparative Example UDL-1 | R1 (10) | — | — | — | — | 90 |
| Comparative Example UDL-2 | R2 (10) | XL2 (2) | AG1 (0.1) | — | 70 | 30 |
| Comparative Example UDL-3 | R3 (10) | XL2 (2) | AG1 (0.1) | — | — | 90 |
| Comparative Example UDL-4 | R4 (10) | — | — | — | — | 90 |

The structural formulae of the crosslinking agents (XL1, XL2) and the thermal acid generator (AG1) used in Comparative UDLs are shown below.

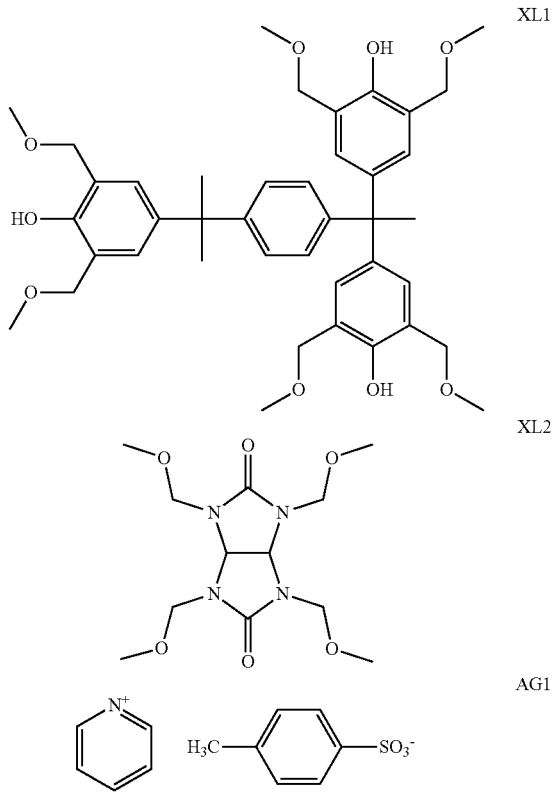

Example 1: Adhesiveness and Filling Property Evaluations (Examples 1-1 to 1-32, Comparative Examples 1-1 to 1-4)

As shown in FIG. 2, the materials (UDL-1 to -32, Comparative Example UDL-1 to -4) for forming an organic film were each applied onto a SiO₂ wafer substrate having a dense hole pattern (hole diameter: 0.16 μm, hole depth: 2.0 μm, distance between the centers of adjacent two holes: 0.32 μm), the SiO₂ wafer substrate having been treated with hexamethyldisilazane (HMDS). The resultant was baked with a hot plate in the atmosphere under conditions shown in Tables 4-1 and 4-2. Thereby, an organic film 8 was formed. The substrate used was a base substrate 7 (SiO₂ wafer substrate) having a dense hole pattern as shown in FIG. 2 (G) (top view) and (H) (sectional view). The sectional shapes of the resulting wafer substrates were observed with a scanning electron microscope (SEM) to check whether or not the holes were filled with the organic film without voids (space). Tables 4-1 and 4-2 show the results. If a material for forming an organic film has poor filling property, voids occur inside the holes in this evaluation. Moreover, if the adhesiveness is insufficient, peeling from the substrate is observed when viewed in the cross section. If a material for forming an organic film has favorable adhesiveness and filling property, the holes are filled with the organic film without voids in this evaluation as shown in FIG. 2 (I).

TABLE 4-1

| | Material for forming organic film | Presence/absence of voids or peeling | Baking conditions |
|---|---|---|---|
| Example 1-1 | UDL-1 | absence | 250° C. × 60 sec. |
| Example 1-2 | UDL-2 | absence | 300° C. × 60 sec. |
| Example 1-3 | UDL-3 | absence | 250° C. × 60 sec. |
| Example 1-4 | UDL-4 | absence | 300° C. × 60 sec. |
| Example 1-5 | UDL-5 | absence | 250° C. × 60 sec. |
| Example 1-6 | UDL-6 | absence | 300° C. × 60 sec. |
| Example 1-7 | UDL-7 | absence | 250° C. × 60 sec. |
| Example 1-8 | UDL-8 | absence | 250° C. × 60 sec. |
| Example 1-9 | UDL-9 | absence | 250° C. × 60 sec. |
| Example 1-10 | UDL-10 | absence | 300° C. × 60 sec. |
| Example 1-11 | UDL-11 | absence | 300° C. × 60 sec. |
| Example 1-12 | UDL-12 | absence | 250° C. × 60 sec. |
| Example 1-13 | UDL-13 | absence | 250° C. × 60 sec. |
| Example 1-14 | UDL-14 | absence | 250° C. × 60 sec. |
| Example 1-15 | UDL-15 | absence | 250° C. × 60 sec. |
| Example 1-16 | UDL-16 | absence | 300° C. × 60 sec. |
| Example 1-17 | UDL-17 | absence | 250° C. × 60 sec. |
| Example 1-18 | UDL-18 | absence | 250° C. × 60 sec. |

TABLE 4-2

| | Material for forming organic film | Presence/absence of voids or peeling | Baking conditions |
|---|---|---|---|
| Example 1-19 | UDL-19 | absence | 250° C. × 60 sec. |
| Example 1-20 | UDL-20 | absence | 250° C. × 60 sec. |
| Example 1-21 | UDL-21 | absence | 250° C. × 60 sec. |
| Example 1-22 | UDL-22 | absence | 250° C. × 60 sec. |
| Example 1-23 | UDL-23 | absence | 300° C. × 60 sec. |
| Example 1-24 | UDL-24 | absence | 300° C. × 60 sec. |
| Example 1-25 | UDL-25 | absence | 250° C. × 60 sec. |
| Example 1-26 | UDL-26 | absence | 250° C. × 60 sec. |
| Example 1-27 | UDL-27 | absence | 250° C. × 60 sec. |
| Example 1-28 | UDL-28 | absence | 250° C. × 60 sec. |
| Example 1-29 | UDL-29 | absence | 250° C. × 60 sec. |
| Example 1-30 | UDL-30 | absence | 250° C. × 60 sec. |
| Example 1-31 | UDL-31 | absence | 250° C. × 60 sec. |
| Example 1-32 | UDL-32 | absence | 250° C. × 60 sec. |
| Comparative Example 1-1 | Comparative Example UDL-1 | peeled | 250° C. × 60 sec. |
| Comparative Example 1-2 | Comparative Example UDL-2 | peeled | 250° C. × 60 sec. |
| Comparative Example 1-3 | Comparative Example UDL-3 | with voids | 250° C. × 60 sec. |
| Comparative Example 1-4 | Comparative Example UDL-4 | peeled | 350° C. × 60 sec. |

As shown in Tables 4-1 and 4-2, Examples 1-1 to 1-32 using the inventive materials (UDL-1 to UDL-32) for forming an organic film enable the hole pattern to be filled without peeling and voids. This verifies that the adhesiveness to the substrate and the filling property were favorable. Meanwhile, in Comparative Examples 1-1, 1-2, and 1-4, the adhesiveness was insufficient, and peeling on the patterned substrate was observed. Moreover, in Comparative Example 1-3, peeling due to insufficient adhesiveness was not observed, but void formation due to insufficient filling property was observed. Compounds (R1), (R2), and (R3) respectively incorporated in the materials for forming an organic film (Comparative Example UDL-1, UDL-2, and UDL-3) used in Comparative Examples 1-1, 1-2, and 1-3 do not contain an imide group. Compound (R4) incorporated in the material for forming an organic film (Comparative Example UDL-4) used in Comparative Example 1-4 does not contain a hydroxyl group. These results indicated that the imide group introduced to a terminal group and linked with a flexible chain having a hydroxyl group has favorable actions on filling property and adhesiveness to a substrate.

Example 2: Planarizing Property Evaluation (Examples 2-1 to 2-32, Comparative Examples 2-1 to 2-4)

The materials (UDL-1 to -32, Comparative Example UDL-1 to -4) for forming an organic film were each applied onto a base substrate 9 (SiO$_2$ wafer substrate) having a giant isolated trench pattern (FIG. 3 (J), trench width: 10 μm, trench depth: 0.10 μm), and baked with a hot plate in the atmosphere under conditions shown in Tables 5-1 and 5-2. Then, a step (delta 10 in FIG. 3 (K)) between the trench portion and the non-trench portion of an organic film 10 was observed with an atomic force microscope (AFM) NX10 manufactured by Park systems Corp. Tables 5-1 and 5-2 show the results. In this evaluation, the smaller the step, the better the planarizing property. Note that, in this evaluation, a trench pattern having a depth of 0.10 μm was generally planarized using an organic film material having a film thickness of 200 nm. This is a severe evaluation condition to evaluate the planarizing property.

TABLE 5-1

| | Material for forming organic film | Step (nm) | Baking conditions |
|---|---|---|---|
| Example 2-2 | UDL-2 | 25 | 300° C. × 60 sec. |
| Example 2-3 | UDL-3 | 30 | 250° C. × 60 sec. |
| Example 2-4 | UDL-4 | 40 | 300° C. × 60 sec. |
| Example 2-5 | UDL-5 | 35 | 250° C. × 60 sec. |
| Example 2-6 | UDL-6 | 30 | 300° C. × 60 sec. |
| Example 2-7 | UDL-7 | 35 | 250° C. × 60 sec. |
| Example 2-8 | UDL-8 | 25 | 250° C. × 60 sec. |
| Example 2-9 | UDL-9 | 30 | 250° C. × 60 sec. |
| Example 2-10 | UDL-10 | 35 | 300° C. × 60 sec. |
| Example 2-11 | UDL-11 | 25 | 300° C. × 60 sec. |
| Example 2-12 | UDL-12 | 30 | 250° C. × 60 sec. |
| Example 2-13 | UDL-13 | 20 | 250° C. × 60 sec. |
| Example 2-14 | UDL-14 | 25 | 250° C. × 60 sec. |
| Example 2-15 | UDL-15 | 20 | 250° C. × 60 sec. |
| Example 2-16 | UDL-16 | 30 | 300° C. × 60 sec. |
| Example 2-17 | UDL-17 | 30 | 250° C. × 60 sec. |
| Example 2-18 | UDL-18 | 25 | 250° C. × 60 sec. |

TABLE 5-2

| | Material for forming organic film | Step (nm) | Baking conditions |
|---|---|---|---|
| Example 2-20 | UDL-20 | 35 | 250° C. × 60 sec. |
| Example 2-21 | UDL-21 | 30 | 250° C. × 60 sec. |
| Example 2-22 | UDL-22 | 20 | 250° C. × 60 sec. |
| Example 2-23 | UDL-23 | 25 | 300° C. × 60 sec. |
| Example 2-24 | UDL-24 | 20 | 300° C. × 60 sec. |
| Example 2-25 | UDL-25 | 20 | 250° C. × 60 sec. |
| Example 2-26 | UDL-26 | 30 | 250° C. × 60 sec. |
| Example 2-27 | UDL-27 | 30 | 250° C. × 60 sec. |
| Example 2-28 | UDL-28 | 15 | 250° C. × 60 sec. |
| Example 2-29 | UDL-29 | 25 | 250° C. × 60 sec. |
| Example 2-30 | UDL-30 | 30 | 250° C. × 60 sec. |
| Example 2-31 | UDL-31 | 20 | 250° C. × 60 sec. |
| Example 2-32 | UDL-32 | 20 | 250° C. × 60 sec. |
| Comparative Example 2-1 | Comparative Example UDL-1 | 50 | 250° C. × 60 sec. |
| Comparative Example 2-2 | Comparative Example UDL-2 | 90 | 250° C. × 60 sec. |
| Comparative Example 2-3 | Comparative Example UDL-3 | 90 | 250° C. × 60 sec. |
| Comparative Example 2-4 | Comparative Example UDL-4 | 35 | 350° C. × 60 sec. |

As shown in Tables 5-1 and 5-2, in Examples 2-1 to 2-32 using the inventive materials for forming an organic film, the organic films had smaller steps between the trench and non-trench portions than those in Comparative Examples 2-1 to 2-3 using no compound containing an imide group. This verifies that the planarizing property was excellent. Furthermore, the comparison between Examples 2-31, 2-32 in which the high-boiling-point solvents were added and Example 2-3 without the high-boiling-point solvents shows that adding the high-boiling-point solvents further improved the planarizing property.

Example 3: Adhesiveness Test (Examples 3-1 to 3-32, Comparative Examples 3-1 to 3-4)

The materials (UDL-1 to -32, Comparative Example UDL-1 to -4) for forming an organic film were each applied onto a SiO$_2$ wafer substrate, and baked with a hot plate in the atmosphere under conditions shown in Tables 6-1 and 6-2. Thereby, an organic film having a film thickness of 200 nm was formed. The wafer with this organic film was cut out into a 1×1 cm square, and an aluminum pin with epoxy adhesive was fastened to the cut wafer by using a dedicated jig. Then, the assembly was heated using an oven at 150° C. for 1 hour to bond the aluminum pin to the substrate. After cooling to room temperature, initial adhesiveness was evaluated based on the resistance force by using a thin-film adhesion strength measurement apparatus (Sebastian Five-A).

FIG. 4 shows an explanatory view for illustrating the method for measuring the adhesiveness. In FIG. 4, reference number 11 denotes a silicon wafer (substrate), 12 denotes a cured film, 13 denotes an aluminum pin with adhesive, 14 denotes a support, 15 denotes a grip, and 16 denotes a tensile direction. Each adhesive force is an average value of 12 measurement points. The larger the numerical value, the higher the adhesiveness of the organic film to the substrate. The obtained numerical values were compared to evaluate the adhesivenesses. Tables 6-1 and 6-2 show the results.

TABLE 6-1

| | Material for forming organic film | Adhesive force (mN) | Baking conditions |
|---|---|---|---|
| Example 3-1 | UDL-1 | 350 | 250° C. × 60 sec. |
| Example 3-2 | UDL-2 | 380 | 300° C. × 60 sec. |
| Example 3-3 | UDL-3 | 410 | 250° C. × 60 sec. |
| Example 3-4 | UDL-4 | 450 | 300° C. × 60 sec. |
| Example 3-5 | UDL-5 | 480 | 250° C. × 60 sec. |
| Example 3-6 | UDL-6 | 410 | 300° C. × 60 sec. |
| Example 3-7 | UDL-7 | 390 | 250° C. × 60 sec. |
| Example 3-8 | UDL-8 | 360 | 250° C. × 60 sec. |
| Example 3-9 | UDL-9 | 410 | 250° C. × 60 sec. |
| Example 3-10 | UDL-10 | 430 | 300° C. × 60 sec. |
| Example 3-11 | UDL-11 | 500 | 300° C. × 60 sec. |
| Example 3-12 | UDL-12 | 470 | 250° C. × 60 sec. |
| Example 3-13 | UDL-13 | 520 | 250° C. × 60 sec. |
| Example 3-14 | UDL-14 | 450 | 250° C. × 60 sec. |
| Example 3-15 | UDL-15 | 540 | 250° C. × 60 sec. |
| Example 3-16 | UDL-16 | 550 | 300° C. × 60 sec. |
| Example 3-17 | UDL-17 | 480 | 250° C. × 60 sec. |
| Example 3-18 | UDL-18 | 500 | 250° C. × 60 sec. |

TABLE 6-2

| | Material for forming organic film | Adhesive force (mN) | Baking conditions |
|---|---|---|---|
| Example 3-19 | UDL-19 | 500 | 250° C. × 60 sec. |
| Example 3-20 | UDL-20 | 490 | 250° C. × 60 sec. |
| Example 3-21 | UDL-21 | 420 | 250° C. × 60 sec. |
| Example 3-22 | UDL-22 | 390 | 250° C. × 60 sec. |
| Example 3-23 | UDL-23 | 440 | 300° C. × 60 sec. |
| Example 3-24 | UDL-24 | 460 | 300° C. × 60 sec. |
| Example 3-25 | UDL-25 | 510 | 250° C. × 60 sec. |
| Example 3-26 | UDL-26 | 430 | 250° C. × 60 sec. |
| Example 3-27 | UDL-27 | 470 | 250° C. × 60 sec. |
| Example 3-28 | UDL-28 | 380 | 250° C. × 60 sec. |
| Example 3-29 | UDL-29 | 450 | 250° C. × 60 sec. |
| Example 3-30 | UDL-30 | 460 | 250° C. × 60 sec. |
| Example 3-31 | UDL-31 | 400 | 250° C. × 60 sec. |
| Example 3-32 | UDL-32 | 410 | 250° C. × 60 sec. |
| Comparative Example 3-1 | Comparative UDL-1 | 200 | 250° C. × 60 sec. |
| Comparative Example 3-2 | Comparative UDL-2 | 240 | 250° C. × 60 sec. |
| Comparative Example 3-3 | Comparative UDL-3 | 300 | 250° C. × 60 sec. |
| Comparative Example 3-4 | Comparative UDL-4 | 220 | 350° C. × 60 sec. |

As shown in Tables 6-1 and 6-2, it was verified that Examples 3-1 to 3-32 using the inventive materials for forming an organic film were excellent in adhesive force in comparison with Comparative Examples 3-1 to 3-4 not using the compound having the imide group introduced to a terminal group and linked with a flexible chain having a hydroxyl group. It can be seen that the adhesive forces in Examples 3-1 to 3-32 using the inventive materials for forming an organic film are approximately twice as much as those of Comparative UDL-1, -2, and -4 which caused peeling in Adhesiveness and Filling Property Evaluations. This result also indicates that the imide group introduced to a terminal group and linked with a flexible chain having a hydroxyl group contributes to the expression of the favorable adhesiveness.

Example 4: Pattern Etching Test (Examples 4-1 to 4-32, Comparative Examples 4-1 to 4-4)

UDL-1 to -32 and Comparative Example UDL-1 to -4 prepared above were each applied onto a SiO$_2$ substrate having a trench pattern (trench width: 10 μm, trench depth: 0.10 μm) on which an HMDS-treated SiO$_2$ film with a film thickness of 200 nm had been formed. The resultant was baked in the atmosphere under conditions shown in Tables 10-1 and 10-2 to form a resist underlayer film with a film thickness of 200 nm on the Bare Si substrate. A silicon-containing resist middle layer film material (SOG-1) was applied on the resist underlayer film and baked at 220° C. for 60 seconds to form a resist middle layer film having a film thickness of 35 nm. A resist upper layer film material (SL resist for ArF) was applied thereon and baked at 105° C. for 60 seconds to form a resist upper layer film having a film thickness of 100 nm. A liquid immersion top coat material (TC-1) was applied on the resist upper layer film and baked at 90° C. for 60 seconds to form a top coat having a film thickness of 50 nm.

The resist upper layer film material (SL resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 7; and filtering the solution through a 0.1-μm filter made of a fluorinated resin.

TABLE 7

| | Polymer (parts by mass) | Acid generator (parts by mass) | Basic compound (parts by mass) | Solvent (parts by mass) |
|---|---|---|---|---|
| Monolayer resist for ArF | RP1 (100) | PAG1 (6.6) | Amine1 (0.8) | PGMEA (2500) |

The structural formulae of the polymer (RP1), acid generator (PAG1), and basic compound (Amine1) used are shown below.

RP1

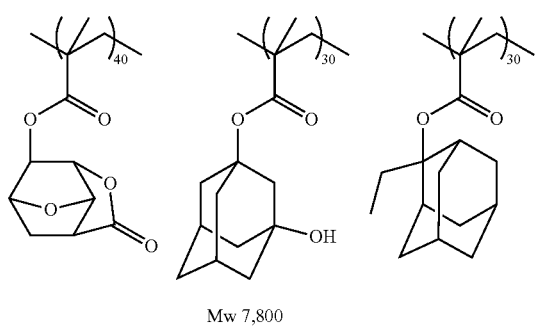

Mw 7,800

PAG1

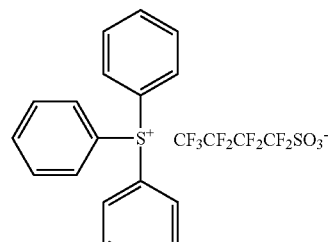

Amine1

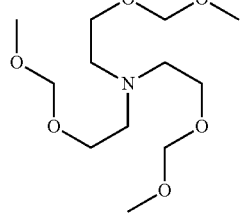

The liquid immersion top coat material (TC-1) was prepared by: dissolving a top coat polymer (PP1) into organic solvents in proportions shown in Table 8; and filtering the solution through a 0.1-μm filter made of a fluorinated resin.

TABLE 8

| | Polymer (parts by mass) | Organic solvent (parts by mass) |
|---|---|---|
| TC-1 | PP1 (100) | diisoamyl ether (2700) 2-methyl-1-butanol (270) |

The structural formula of the polymer (PP1) used is shown below.

PP1

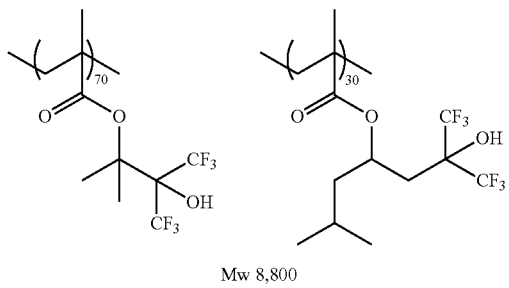

Mw 8,800

The silicon-containing resist middle layer film material (SOG-1) was prepared by: dissolving an ArF silicon-containing middle layer film polymer shown by (SiP1) and a crosslinking catalyst (CAT1) into an organic solvent containing 0.1 mass % FC-4430 (manufactured by Sumitomo 3M Ltd.) in proportions shown in Table 9; and filtering the solution through a filter having a pore size of 0.1 μm and made of a fluorinated resin.

TABLE 9

| | Polymer (parts by mass) | Thermal crosslinking catalyst (parts by mass) | organic solvent (parts by mass) |
|---|---|---|---|
| SOG1 | SiP1 (100) | CAT1 (1) | propylene glycol monoethyl ether (4000) |

The structural formulae of the ArF silicon-containing middle layer film polymer (SiP1) and crosslinking catalyst (CAT1) used are shown below.

SiP1

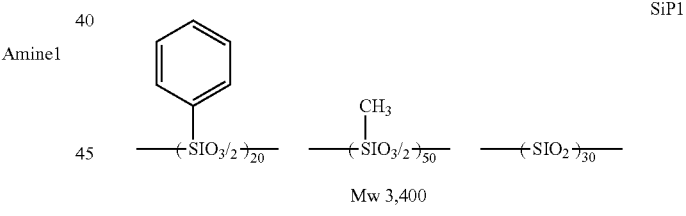

Mw 3,400

CAT1

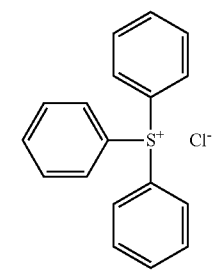

Next, the resulting substrate was exposed to light at various exposure levels with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked at 100° C. for 60 seconds (PEB), and developed with a 2.38 mass % tetramethylammonium hydroxide (TMAH) aqueous solution for 30 seconds. Thus, a positive line and space pattern was obtained with the resist line width ranging from 50 nm to 30 nm at a pitch of 100 nm.

Then, dry-etching processing with an etching apparatus Telius manufactured by Tokyo Electron Limited was performed successively as follows. The silicon-containing middle layer film was processed while using the resist pattern as a mask; the underlayer film was processed while using the silicon-containing middle layer film as a mask; and the $SiO_2$ film was processed while using the underlayer film as a mask.

The etching conditions were as follows.

Conditions for transferring the resist pattern to the SOG film:

| | |
|---|---|
| Chamber pressure | 10.0 Pa |
| RF power | 1,500 W |
| $CF_4$ gas flow rate | 15 sccm |
| $O_2$ gas flow rate | 75 sccm |
| Time | 15 sec |

Transferring conditions from the SOG film to the underlayer film:

| | |
|---|---|
| Chamber pressure | 2.0 Pa |
| RF power | 500 W |
| Ar gas flow rate | 75 sccm |
| $O_2$ gas flow rate | 45 sccm |
| Time | 120 sec |

Transferring conditions to the $SiO_2$ film:

| | |
|---|---|
| Chamber pressure | 2.0 Pa |
| RF power | 2,200 W |
| $C_5F_{12}$ gas flow rate | 20 sccm |
| $C_2F_6$ gas flow rate | 10 sccm |
| Ar gas flow rate | 300 sccm |
| $O_2$ | 60 sccm |
| Time | 90 sec |

The pattern cross sections were observed with an electron microscope (S-4700) manufactured by Hitachi, Ltd. The profiles were compared and summarized in Tables 10-1 and 10-2.

TABLE 10-1

| | Material for forming organic film | Pattern profile after etching for transferring to substrate | Baking conditions |
|---|---|---|---|
| Example 4-1 | UDL-1 | vertical profile | 250° C. × 60 sec. |
| Example 4-2 | UDL-2 | vertical profile | 300° C. × 60 sec. |
| Example 4-3 | UDL-3 | vertical profile | 250° C. × 60 sec. |
| Example 4-4 | UDL-4 | vertical profile | 300° C. × 60 sec. |
| Example 4-5 | UDL-5 | vertical profile | 250° C. × 60 sec. |
| Example 4-6 | UDL-6 | vertical profile | 300° C. × 60 sec. |
| Example 4-7 | UDL-7 | vertical profile | 250° C. × 60 sec. |
| Example 4-8 | UDL-8 | vertical profile | 250° C. × 60 sec. |
| Example 4-9 | UDL-9 | vertical profile | 250° C. × 60 sec. |
| Example 4-10 | UDL-10 | vertical profile | 300° C. × 60 sec. |
| Example 4-11 | UDL-11 | vertical profile | 300° C. × 60 sec. |
| Example 4-12 | UDL-12 | vertical profile | 250° C. × 60 sec. |
| Example 4-13 | UDL-13 | vertical profile | 250° C. × 60 sec. |
| Example 4-14 | UDL-14 | vertical profile | 250° C. × 60 sec. |
| Example 4-15 | UDL-15 | vertical profile | 250° C. × 60 sec. |
| Example 4-16 | UDL-16 | vertical profile | 300° C. × 60 sec. |
| Example 4-17 | UDL-17 | vertical profile | 250° C. × 60 sec. |
| Example 4-18 | UDL-18 | vertical profile | 250° C. × 60 sec. |

TABLE 10-2

| | Material for forming organic film | Pattern profile after etching for transferring to substrate | Baking conditions |
|---|---|---|---|
| Example 4-19 | UDL-19 | vertical profile | 250° C. × 60 sec. |
| Example 4-20 | UDL-20 | vertical profile | 250° C. × 60 sec. |
| Example 4-21 | UDL-21 | vertical profile | 250° C. × 60 sec. |
| Example 4-22 | UDL-22 | vertical profile | 250° C. × 60 sec. |
| Example 4-23 | UDL-23 | vertical profile | 300° C. × 60 sec. |
| Example 4-24 | UDL-24 | vertical profile | 300° C. × 60 sec. |
| Example 4-25 | UDL-25 | vertical profile | 250° C. × 60 sec. |
| Example 4-26 | UDL-26 | vertical profile | 250° C. × 60 sec. |
| Example 4-27 | UDL-27 | vertical profile | 250° C. × 60 sec. |
| Example 4-28 | UDL-28 | vertical profile | 250° C. × 60 sec. |
| Example 4-29 | UDL-29 | vertical profile | 250° C. × 60 sec. |
| Example 4-30 | UDL-30 | vertical profile | 250° C. × 60 sec. |
| Example 4-31 | UDL-31 | vertical profile | 250° C. × 60 sec. |
| Example 4-32 | UDL-32 | vertical profile | 250° C. × 60 sec. |
| Comparative Example 4-1 | Comparative UDL-1 | pattern collapsed | 250° C. × 60 sec. |
| Comparative Example 4-2 | Comparative UDL-2 | pattern collapsed | 250° C. × 60 sec. |
| Comparative Example 4-3 | Comparative UDL-3 | pattern collapsed | 250° C. × 60 sec. |
| Comparative Example 4-4 | Comparative UDL-4 | pattern collapsed | 350° C. × 60 sec. |

As shown in Tables 10-1 and 10-2, all the results of the inventive materials for forming an organic film (Examples 4-1 to 4-32) showed that the resist upper layer film pattern was favorably transferred to the final substrate. This confirms that the inventive materials for forming an organic film are suitably used in fine processing according to the multi-layer resist method. Meanwhile, in Comparative Examples 4-1 to 4-3 not using the compound containing an imide group, since the filling property and the adhesiveness were insufficient as demonstrated from the results of Adhesiveness and Filling Property Evaluations, pattern collapse occurred at the patterning, and no pattern was formed. Particularly, in Comparative Example 4-4 using the compound having an imide group but not a hydroxyl group, the planarizing property was favorable, but no pattern was formed due to insufficient adhesiveness to a substrate. These results also suggest that the imide group introduced to a terminal group and linked with a flexible chain having a hydroxyl group has favorable actions.

From the above, it was revealed that the inventive material for forming an organic film has all of high filling property, high planarizing property, and excellent adhesive force to a substrate. Thus, the inventive material for forming an organic film is quite useful as an organic film material used in multilayer resist methods. Moreover, the inventive patterning processes using such a material make it possible to precisely form a fine pattern even when a body to be processed is an uneven substrate.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A material for forming an organic film, comprising: a compound shown by the following general formula (1); and

(1)

wherein X represents an organic group having a valency of n1 and 2 to 50 carbon atoms; n1 represents an integer of 1 to 10; and $R_1$ represents at least one or more of the following general formulae (2) to (4),

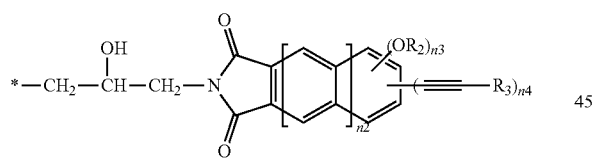
(2)

wherein an asterisk represents a bonding site to the organic group X; n2 represents 0 or 1; n3 and n4 represent integers satisfying relations of $0 \le n3 \le 2$, $0 \le n4 \le 2$, and $1 \le n3+n4 \le 2$; $R_2$ represents any of a hydrogen atom, an allyl group, and a propargyl group; and $R_3$ represents any of a hydrogen atom, a methyl group, and a phenyl group,

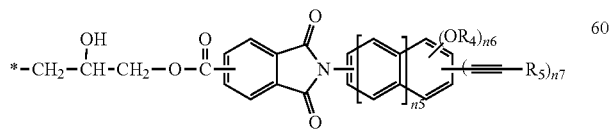
(3)

wherein an asterisk represents a bonding site to the organic group X; n5 represents 0 or 1; n6 and n7 represent integers satisfying relations of $0 \le n6 \le 2$, $0 \le n7 \le 2$, and $1 \le n6+n7 \le 2$; $R_4$ represents any of a hydrogen atom, an allyl group, and a propargyl group; and $R_5$ represents any of a hydrogen atom, a methyl group, and a phenyl group, and

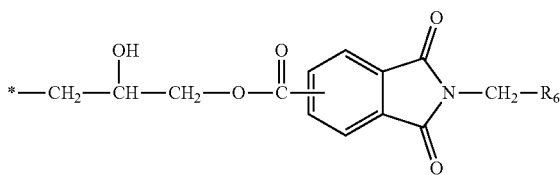
(4)

wherein an asterisk represents a bonding site to the organic group X; and $R_6$ represents a monovalent organic group having an unsaturated bond and 1 to 10 carbon atoms.

2. The material for forming an organic film according to claim 1, wherein the organic group X in the general formula (1) is shown by any of the following general formulae (5), (7), (8), (9), (10), (11), (12), (13), (14), and (15),

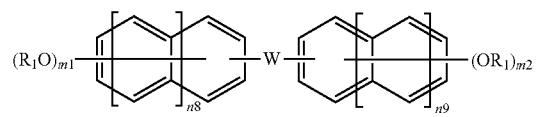
(5)

wherein n8 and n9 each independently represent 0 or 1; W represents a single bond or any of structures shown by (6) below; $R_1$ represents the $R_1$ group; and m1 and m2 each independently represent an integer of 0 to 4, and m1+m2 is 1 or more and 8 or less,

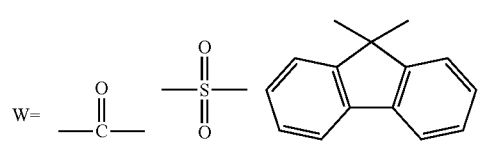
(6)

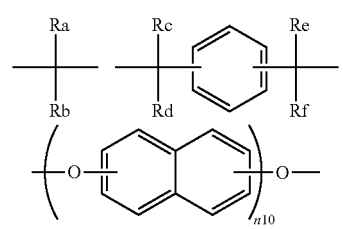

wherein n10 represents an integer of 0 to 3; and Ra, Rb, Rc, Rd, Re, and Rf each independently represent a hydrogen atom, an alkyl group having 1 to 10 carbon atoms optionally substituted with fluorine, or a phenyl group, and Ra and Rb are optionally bonded to each other to form a cyclic compound, (7)

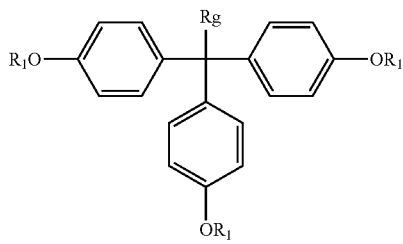

wherein $R_1$ represents the $R_1$ group; and Rg represents a hydrogen atom, a methyl group, or a phenyl group, (8)

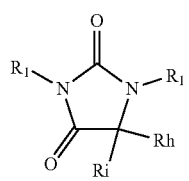

(9)

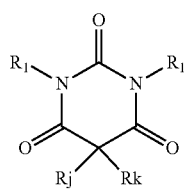

(10)

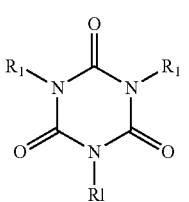

(11)

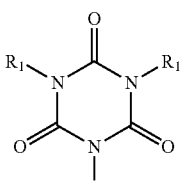

(12)

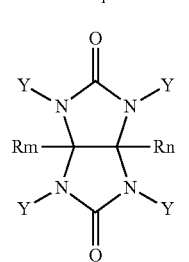

wherein $R_1$ represents the $R_1$ group; Rh, Ri, Rj, Rk, Rl, Rm, and Rn each represent a hydrogen atom, an alkyl group having 1 to 10 carbon atoms, an alkynyl group having 2 to 10 carbon atoms, an alkenyl group having 2 to 10 carbon atoms, a benzyl group optionally having a substituent on an aromatic ring thereof, or a phenyl group; and each Y represents the $R_1$ group, a hydrogen atom, an alkyl group having 1 to 10 carbon atoms, an alkynyl group having 2 to 10 carbon atoms, or an alkenyl group having 2 to 10 carbon atoms, and at least two of four Y's in the general formula (12) are the $R_1$ groups, and (13)

(14)

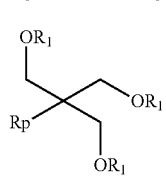

(15)

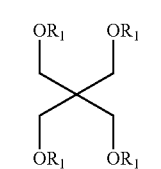

wherein $R_1$ represents the $R_1$ group; Ro represents a linear, branched, or cyclic, saturated or unsaturated hydrocarbon group having 1 to 20 carbon atoms; and Rp represents a hydrogen atom or an alkyl group having 1 to 10 carbon atoms.

3. The material for forming an organic film according to claim 1, wherein the $R_1$ group in the general formula (1) comprises:

any one or more shown by the general formulae (2) to (4); and any one or more shown by the following general formulae (16) and (17), (16)

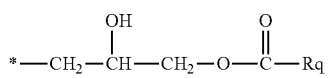

wherein Rq represents a linear, branched, or cyclic, saturated or unsaturated hydrocarbon group having 1 to 30 carbon atoms; and a methylene group constituting the Rq group is optionally substituted with an oxygen atom or a carbonyl group, and (17)

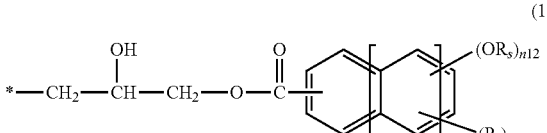

wherein Rs represents a hydrogen atom or a linear or branched hydrocarbon group having 1 to 10 carbon atoms; Rt represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n11 represents any of 0 to 2; and n12 and n13 each represent the number of substituents on an aromatic ring, n12 and n13 each represent an integer of 0 to 7, and n12+n13 is 0 or more and 7 or less.

4. The material for forming an organic film according to claim 1, further comprising one or more of an acid generator, a surfactant, a crosslinking agent, and a plasticizer.

5. The material for forming an organic film according to claim 1, wherein the organic solvent is a mixture of one or more organic solvents each having a boiling point of lower than 180° C. and one or more organic solvents each having a boiling point of 180° C. or higher.

6. A method for forming an organic film that serves as an organic flat film employed in a semiconductor device manufacturing process, the method comprising:
spin-coating a substrate to be processed with the material for forming an organic film according to claim 1; and
heating the substrate at a temperature of 100° C. or higher and 600° C. or lower for 10 seconds to 600 seconds to form a cured film.

7. A method for forming an organic film that serves as an organic flat film employed in a semiconductor device manufacturing process, the method comprising:
spin-coating a substrate to be processed with the material for forming an organic film according to claim 1; and
heating the substrate under an atmosphere with an oxygen concentration of 0.1% or more and 21% or less to form a cured film.

8. The method for forming an organic film according to claim 6, wherein the substrate to be processed has a structure or step with a height of 30 nm or more.

9. A patterning process comprising:
forming a resist underlayer film by using the material for forming an organic film according to claim 1 on a body to be processed;
forming a resist middle layer film by using a silicon-containing resist middle layer film material on the resist underlayer film;
forming a resist upper layer film by using a resist upper layer film material including a photoresist composition on the resist middle layer film;
forming a circuit pattern in the resist upper layer film;
etching the resist middle layer film while using the resist upper layer film having the formed pattern as a mask to transfer the pattern to the resist middle layer film;
etching the resist underlayer film while using the resist middle layer film having the transferred pattern as a mask to transfer the pattern to the resist underlayer film; and
further etching the body to be processed while using the resist underlayer film having the transferred pattern as a mask to form the pattern in the body to be processed.

10. A patterning process comprising:
forming a resist underlayer film by using the material for forming an organic film according to claim 1 on a body to be processed;
forming a resist middle layer film by using a resist middle layer film material containing silicon atoms on the resist underlayer film;
forming an organic antireflective coating on the resist middle layer film;
forming a resist upper layer film on the organic antireflective coating by using a resist upper layer film material including a photoresist composition, so that a four-layered film structure is constructed;
forming a circuit pattern in the resist upper layer film;
etching the organic antireflective coating and the resist middle layer film while using the resist upper layer film having the formed pattern as a mask to transfer the pattern to the organic antireflective coating and the resist middle layer film;
etching the resist underlayer film while using the resist middle layer film having the transferred pattern as a mask to transfer the pattern to the resist underlayer film; and
further etching the body to be processed while using the resist underlayer film having the transferred pattern as a mask to form the pattern in the body to be processed.

11. A patterning process comprising:
forming a resist underlayer film by using the material for forming an organic film according to claim 1 on a body to be processed;
forming an inorganic hard mask middle layer film selected from a silicon oxide film, a silicon nitride film, and a silicon oxynitride film on the resist underlayer film;
forming a resist upper layer film by using a resist upper layer film material including a photoresist composition on the inorganic hard mask middle layer film;
forming a circuit pattern in the resist upper layer film;
etching the inorganic hard mask middle layer film while using the resist upper layer film having the formed pattern as a mask to transfer the pattern to the inorganic hard mask middle layer film;
etching the resist underlayer film while using the inorganic hard mask middle layer film having the formed pattern as a mask to transfer the pattern to the resist underlayer film; and
further etching the body to be processed while using the resist underlayer film having the formed pattern as a mask to form the pattern in the body to be processed.

12. A patterning process comprising:
forming a resist underlayer film by using the material for forming an organic film according to claim 1 on a body to be processed;
forming an inorganic hard mask middle layer film selected from a silicon oxide film, a silicon nitride film, and a silicon oxynitride film on the resist underlayer film;
forming an organic antireflective coating on the inorganic hard mask middle layer film;
forming a resist upper layer film on the organic antireflective coating by using a resist upper layer film material including a photoresist composition, so that a four-layered film structure is constructed;
forming a circuit pattern in the resist upper layer film;
etching the organic antireflective coating and the inorganic hard mask middle layer film while using the resist upper layer film having the formed pattern as a mask to transfer the pattern to the organic antireflective coating and the inorganic hard mask middle layer film;
etching the resist underlayer film while using the inorganic hard mask middle layer film having the formed pattern as a mask to transfer the pattern to the resist underlayer film; and
further etching the body to be processed while using the resist underlayer film having the formed pattern as a mask to form the pattern in the body to be processed.

13. The patterning process according to claim 11, wherein the inorganic hard mask middle layer film is formed by a CVD method or an ALD method.

14. The patterning process according to claim 9, wherein the pattern is formed in the resist upper layer film by a photolithography using light with a wavelength of 10 nm or more and 300 nm or less, direct lithography with electron beam, nanoimprinting, or a combination thereof.

15. The patterning process according to claim 9, wherein the pattern formation in the resist upper layer film involves alkali development or organic solvent development.

16. The patterning process according to claim 9, wherein the body to be processed is a semiconductor device substrate, a metal film, a metal carbide film, a metal oxide film, a metal nitride film, a metal oxycarbide film, or a metal oxynitride film.

17. The patterning process according to claim 9, wherein the body to be processed comprises silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

18. A compound shown by the following general formula (1),

 (1)

wherein X represents an organic group having a valency of n1 and 2 to 50 carbon atoms; n1 represents an integer of 1 to 10; and $R_1$ represents at least one or more of the following general formulae (2) to (4),

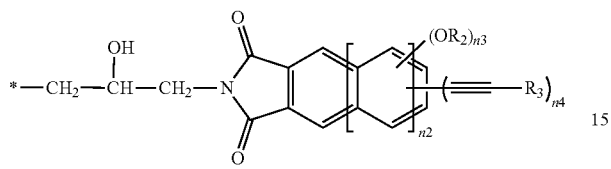 (2)

wherein an asterisk represents a bonding site to the organic group X; n2 represents 0 or 1; n3 and n4 represent integers satisfying relations of $0 \leq n3 \leq 2$, $0 \leq n4 \leq 2$, and $1 \leq n3+n4 \leq 2$; $R_2$ represents any of a hydrogen atom, an allyl group, and a propargyl group; and $R_3$ represents any of a hydrogen atom, a methyl group, and a phenyl group,

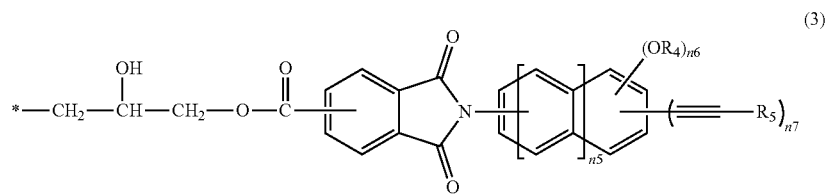 (3)

wherein an asterisk represents a bonding site to the organic group X; n5 represents 0 or 1; n6 and n7 represent integers satisfying relations of $0 \leq n6 \leq 2$, $0 \leq n7 \leq 2$, and $1 \leq n6+n7 \leq 2$; $R_4$ represents any of a hydrogen atom, an allyl group, and a propargyl group; and $R_5$ represents any of a hydrogen atom, a methyl group, and a phenyl group, and

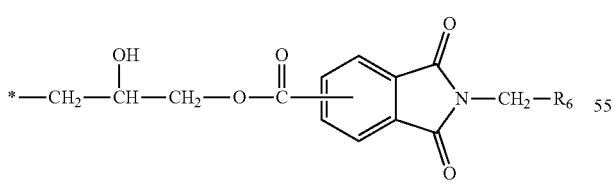 (4)

wherein an asterisk represents a bonding site to the organic group X; and $R_6$ represents a monovalent organic group having an unsaturated bond and 1 to 10 carbon atoms.

19. The compound according to claim 18, wherein the organic group X in the general formula (1) is shown by any of the following general formulae (5), (7), (8), (9), (10), (11), (12), (13), (14), and (15),

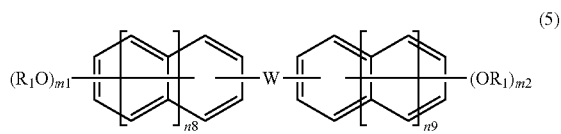 (5)

wherein n8 and n9 each independently represent 0 or 1; W represents a single bond or any of structures shown by (6) below; $R_1$ represents the $R_1$ group; and m1 and m2 each independently represent an integer of 0 to 4, and m1+m2 is 1 or more and 8 or less,

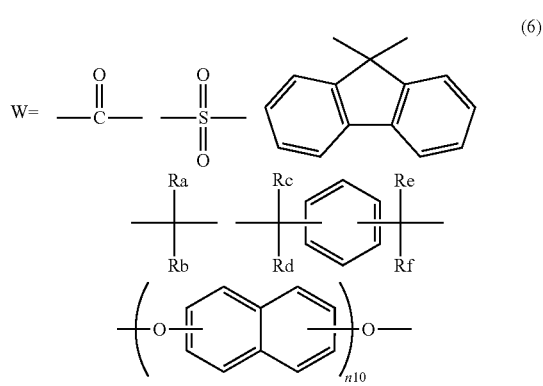 (6)

wherein n10 represents an integer of 0 to 3; and Ra, Rb, Rc, Rd, Re, and Rf each independently represent a hydrogen atom, an alkyl group having 1 to 10 carbon atoms optionally substituted with fluorine, or a phenyl group, and Ra and Rb are optionally bonded to each other to form a cyclic compound,

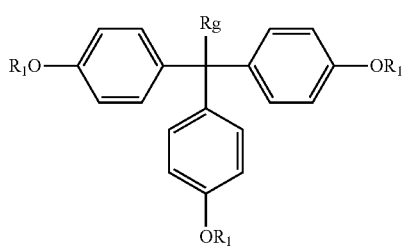
(7)

wherein $R_1$ represents the $R_1$ group; and Rg represents a hydrogen atom, a methyl group, or a phenyl group,

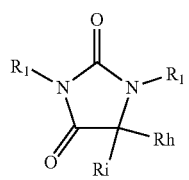
(8)

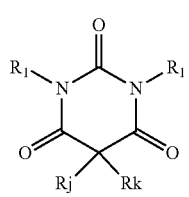
(9)

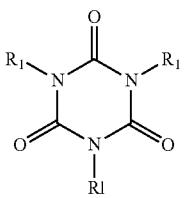
(10)

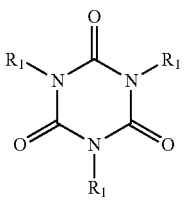
(11)

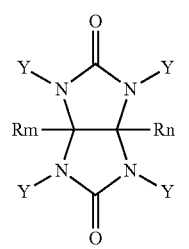
(12)

wherein $R_1$ represents the $R_1$ group; Rh, Ri, Rj, Rk, Rl, Rm, and Rn each represent a hydrogen atom, an alkyl group having 1 to 10 carbon atoms, an alkynyl group having 2 to 10 carbon atoms, an alkenyl group having 2 to 10 carbon atoms, a benzyl group optionally having a substituent on an aromatic ring thereof, or a phenyl group; and each Y represents the $R_1$ group, a hydrogen atom, an alkyl group having 1 to 10 carbon atoms, an alkynyl group having 2 to 10 carbon atoms, or an alkenyl group having 2 to 10 carbon atoms, and at least two of four Y's in the general formula (12) are the $R_1$ groups, and

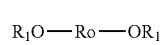
(13)

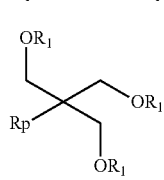
(14)

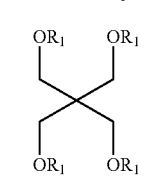
(15)

wherein $R_1$ represents the $R_1$ group; Ro represents a linear, branched, or cyclic, saturated or unsaturated hydrocarbon group having 1 to 20 carbon atoms; and Rp represents a hydrogen atom or an alkyl group having 1 to 10 carbon atoms.

20. The compound according to claim 18, wherein the $R_1$ group in the general formula (1) comprises:
any one or more shown by the general formulae (2) to (4); and
any one or more shown by the following general formulae (16) and (17),

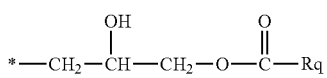
(16)

wherein Rq represents a linear, branched, or cyclic, saturated or unsaturated hydrocarbon group having 1 to 30 carbon atoms; and a methylene group constituting the Rq group is optionally substituted with an oxygen atom or a carbonyl group, and

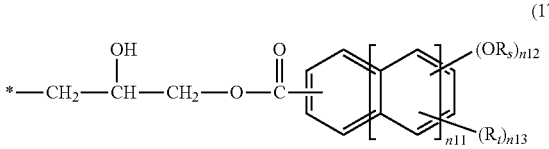
(17)

wherein Rs represents a hydrogen atom or a linear or branched hydrocarbon group having 1 to 10 carbon atoms; Rt represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n11 represents any of 0 to 2; and n12 and n13 each represent the number of substituents on an aromatic ring, n12 and n13 each represent an integer of 0 to 7, and n12+n13 is 0 or more and 7 or less.

* * * * *